(12) United States Patent
Taylor et al.

(10) Patent No.: US 11,179,231 B2
(45) Date of Patent: Nov. 23, 2021

(54) ORAL IRRIGATOR HANDLE FOR USE WITH ORAL AGENT

(71) Applicant: WATER PIK, INC., Fort Collins, CO (US)

(72) Inventors: Kurt M. Taylor, Fort Collins, CO (US); Clifford J. Snyder, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 354 days.

(21) Appl. No.: 15/923,744

(22) Filed: Mar. 16, 2018

(65) Prior Publication Data

US 2018/0263742 A1    Sep. 20, 2018

Related U.S. Application Data

(60) Provisional application No. 62/516,227, filed on Jun. 7, 2017, provisional application No. 62/472,438, filed on Mar. 16, 2017.

(51) Int. Cl.
*A61C 17/02* (2006.01)
*A61M 3/00* (2006.01)
(Continued)

(52) U.S. Cl.
CPC ........ *A61C 17/0202* (2013.01); *A61K 8/0204* (2013.01); *A61M 3/005* (2013.01);
(Continued)

(58) Field of Classification Search
CPC ..... A61C 17/00; A61C 17/02; A61C 17/0202; A61C 17/0214; A61M 3/0279;
(Continued)

(56) References Cited

U.S. PATENT DOCUMENTS 2,813,529 A * 11/1957 Janis-Indrikis ...... A46B 11/063
433/80
3,578,884 A    5/1971 Jacobson
(Continued)

FOREIGN PATENT DOCUMENTS

AU          513194 B2    11/1980
AU         201815406     12/2018
(Continued)

OTHER PUBLICATIONS

International Search Report and Written Opinion dated Jun. 20, 2018 in PCT Application No. PCT/US2018/022893, 12 pages.
(Continued)

*Primary Examiner* — Timothy A Stanis
*Assistant Examiner* — Matthew R Moon
(74) *Attorney, Agent, or Firm* — Dorsey & Whitney LLP

(57) ABSTRACT

An oral irrigator handle for receiving an oral hygiene agent is described. The handle may be connected to a countertop oral irrigator or may be a portion of a handheld oral irrigator. The handle includes a chamber for receiving the oral hygiene agent, where the chamber body positioned within the fluid path of the handle. Fluid flowing into the handle, flows into the chamber, allowing the fluid to intermix with the agent, and then flows from the chamber to a tip connected to the handle.

24 Claims, 31 Drawing Sheets

(51) Int. Cl.
*A61K 8/02* (2006.01)
*A61Q 11/00* (2006.01)
*A61M 3/02* (2006.01)

(52) U.S. Cl.
CPC ........... *A61M 3/0279* (2013.01); *A61Q 11/00* (2013.01); *A61M 2205/7545* (2013.01)

(58) Field of Classification Search
CPC .......... A61M 3/005; A61M 2205/7545; A61Q 11/00; A61K 8/0204
See application file for complete search history.

(56) References Cited

U.S. PATENT DOCUMENTS

| | | | |
|---|---|---|---|
| D304,231 S | 10/1989 | Stream | |
| 5,100,319 A | 3/1992 | Baum | |
| 5,554,025 A * | 9/1996 | Kinsel | A61C 1/0076 |
| | | | 210/321.64 |
| 5,857,851 A | 1/1999 | Chavanne | |
| 6,183,254 B1 * | 2/2001 | Cohen | A61C 17/065 |
| | | | 433/92 |
| D438,954 S | 3/2001 | Orsing | |
| D450,382 S | 11/2001 | Nestenborg | |
| 6,485,304 B2 | 11/2002 | Beerstecher et al. | |
| D468,422 S | 1/2003 | McCurrach | |
| 6,607,711 B2 | 8/2003 | Pedersen et al. | |
| 6,648,644 B1 | 11/2003 | Flemmig et al. | |
| 6,837,709 B2 | 1/2005 | Sierro et al. | |
| 7,083,411 B2 | 8/2006 | Flemmig et al. | |
| D533,270 S | 12/2006 | Kierce et al. | |
| D563,674 S | 3/2008 | Beedham | |
| D625,105 S | 10/2010 | Winkler | |
| 7,980,923 B2 | 7/2011 | Olmo et al. | |
| D648,941 S | 11/2011 | Leung | |
| D651,805 S | 1/2012 | Hay et al. | |
| 8,652,495 B2 | 2/2014 | Porter et al. | |
| 8,858,921 B2 | 10/2014 | Schmid et al. | |
| D717,547 S | 11/2014 | Adriaenssen et al. | |
| D719,737 S | 12/2014 | Adriaenssen et al. | |
| 9,259,301 B2 | 2/2016 | Zhadanov et al. | |
| 9,339,350 B2 | 5/2016 | Olmo et al. | |
| 9,358,185 B2 | 6/2016 | Haeberlein et al. | |
| 9,493,731 B2 | 11/2016 | Mueller | |
| 9,498,416 B2 | 11/2016 | Li et al. | |
| D773,822 S | 12/2016 | Sikora et al. | |
| 9,532,932 B2 | 1/2017 | Prencipe et al. | |
| 9,566,397 B2 * | 2/2017 | Faram | A61M 15/004 |
| D782,657 S | 3/2017 | Williams | |
| D790,859 S | 7/2017 | McGarry et al. | |
| D799,217 S | 10/2017 | Massee | |
| D800,896 S | 10/2017 | Roberts et al. | |
| D802,120 S | 11/2017 | Boyd et al. | |
| D812,219 S | 3/2018 | Wang | |
| D851,239 S | 6/2019 | Chen | |
| D859,645 S | 9/2019 | Uchida | |
| D866,750 S | 11/2019 | Fan et al. | |
| D868,243 S | 11/2019 | Taylor et al. | |
| D870,268 S | 12/2019 | Massie et al. | |
| 10,524,889 B1 | 1/2020 | Bordas | |
| D877,324 S | 3/2020 | Massie et al. | |
| 2004/0202980 A1 | 10/2004 | Policicchio | |
| 2006/0222600 A1 | 10/2006 | Pinyayev | |
| 2007/0080240 A1 | 4/2007 | Schuetz | |
| 2007/0202459 A1 | 8/2007 | Boyd et al. | |
| 2007/0203439 A1 * | 8/2007 | Boyd | F04B 49/24 |
| | | | 601/162 |
| 2008/0245795 A1 * | 10/2008 | Berge | B65D 47/0814 |
| | | | 220/264 |
| 2010/0012193 A1 * | 1/2010 | Anson | B65D 47/243 |
| | | | 137/1 |
| 2010/0239998 A1 | 9/2010 | Snyder et al. | |
| 2010/0297577 A1 * | 11/2010 | Cohen | A61M 1/0056 |
| | | | 433/92 |
| 2011/0027328 A1 | 2/2011 | Baig et al. | |
| 2013/0337413 A1 | 12/2013 | Donnet et al. | |
| 2014/0106296 A1 | 4/2014 | Woodard et al. | |
| 2014/0272769 A1 | 9/2014 | Luettgen et al. | |
| 2015/0182319 A1 * | 7/2015 | Wagner | A61C 17/0202 |
| | | | 132/308 |
| 2015/0232511 A1 | 8/2015 | Hug et al. | |
| 2015/0282909 A1 * | 10/2015 | Roberts | A61C 17/0202 |
| | | | 433/88 |
| 2016/0022931 A1 * | 1/2016 | Althorpe | A61M 15/003 |
| | | | 128/203.12 |
| 2016/0220452 A1 | 8/2016 | Donnet | |
| 2017/0000592 A1 | 1/2017 | Shalev et al. | |
| 2017/0027848 A1 | 2/2017 | Li et al. | |
| 2017/0071711 A1 | 3/2017 | Shalev | |
| 2017/0087065 A1 | 3/2017 | Berglund et al. | |
| 2017/0209246 A1 | 7/2017 | Williams et al. | |
| 2018/0153666 A1 | 6/2018 | Snyder et al. | |
| 2018/0168785 A1 | 6/2018 | Wagner et al. | |
| 2018/0221260 A1 | 8/2018 | Snyder | |
| 2018/0263742 A1 | 9/2018 | Taylor et al. | |
| 2019/0358006 A1 | 11/2019 | Arias Haber et al. | |

FOREIGN PATENT DOCUMENTS

| | | |
|---|---|---|
| CA | 174897 | 1/2019 |
| CA | 183395 | 10/2019 |
| CA | 190032 | 10/2019 |
| CN | ZL201830517877.7 | 4/2019 |
| DE | 3322716 A1 | 1/1985 |
| DE | 29714212 U1 | 12/1997 |
| EP | 1243226 A2 | 9/2002 |
| EP | 1919435 B1 | 7/2011 |
| EP | 2515784 A1 | 10/2012 |
| EP | 2753292 A2 | 7/2014 |
| EP | 2863835 A1 | 4/2015 |
| EP | 3146933 A1 | 3/2017 |
| JP | 2009125124 A | 6/2009 |
| WO | 2008046580 A1 | 4/2008 |
| WO | 2013080762 A1 | 6/2013 |
| WO | 2016052572 A1 | 4/2016 |
| WO | 2016062742 A1 | 4/2016 |
| WO | 2016124381 A1 | 8/2016 |
| WO | 2018046580 A1 | 3/2018 |

OTHER PUBLICATIONS

International Preliminary Report on Patentability dated Sep. 24, 2013, in PCT Application No. PCT/IB2011/000576, 6 pages.
Waterpik Complete Care 5.0 Toothbrush, posted at amazon.com, earliest date reviewed on Mar. 14, 2016, [online], acquired on Feb. 23, 2018, available from Internet, <URL: https//www.amazon.com/Waterpik-Complete-Toothbrush-Water-Flosser/dp/B01CRZ939Y/ref=cm_cr_arp_d_product_top?ie=UTF8> (Year: 2016).
"How to Use the Waterpik Whitening Water Flosser (WF-06)", video on YouTube.com, posted by Waterpik on Jan. 29, 2018.
Communication pursuant to Article 94(3) EPC dated Dec. 7, 2020, in European Application No. 18715436.4, 6 pages.

* cited by examiner

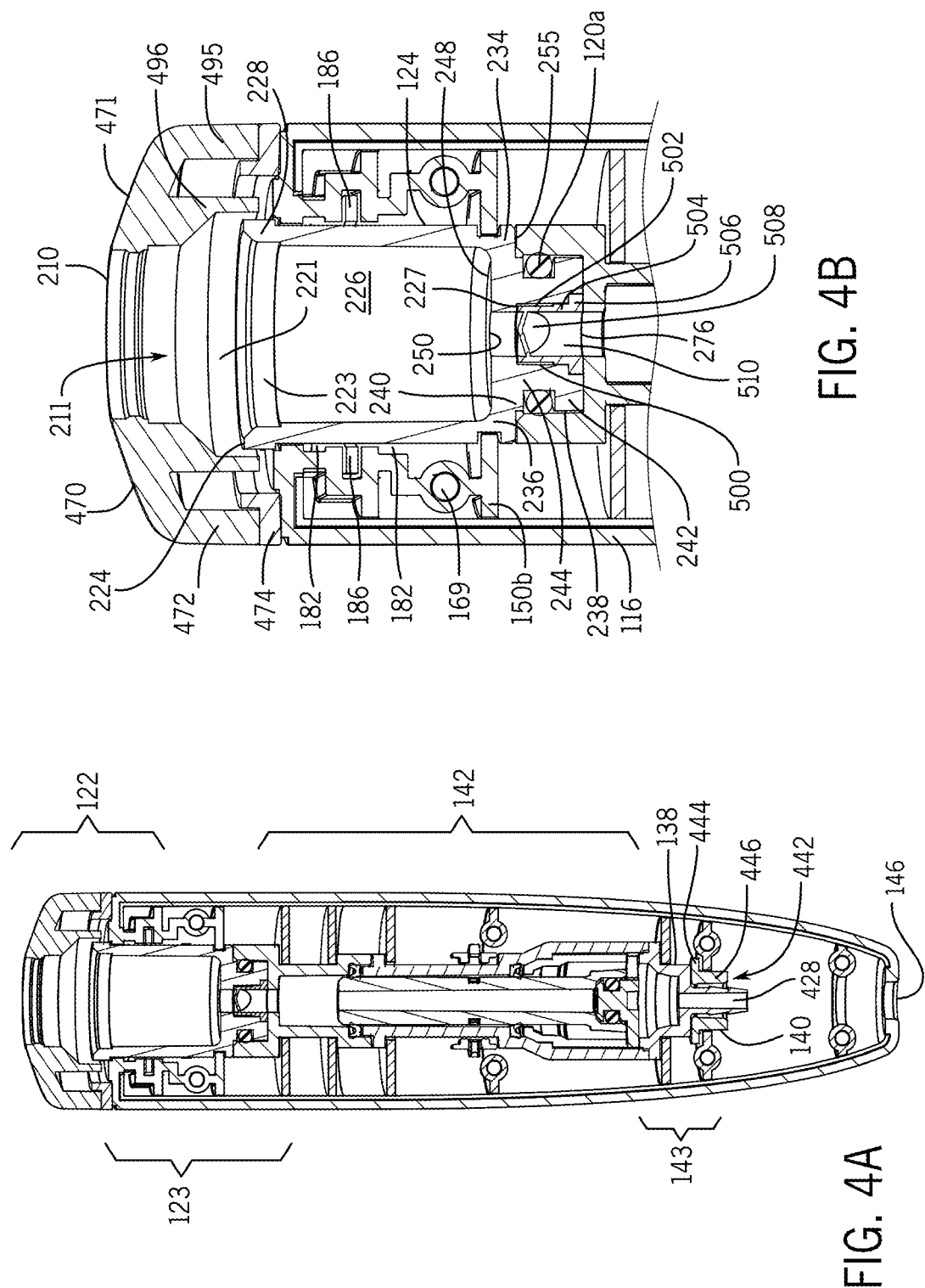

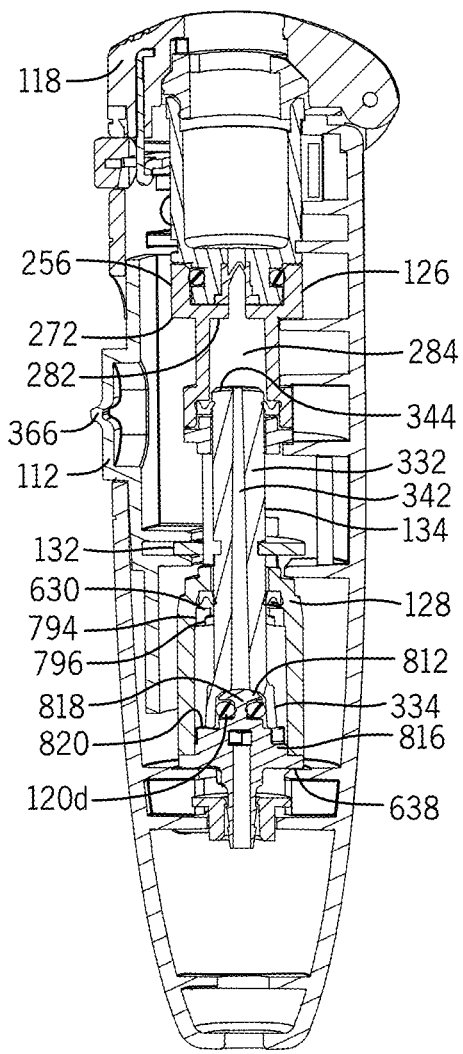
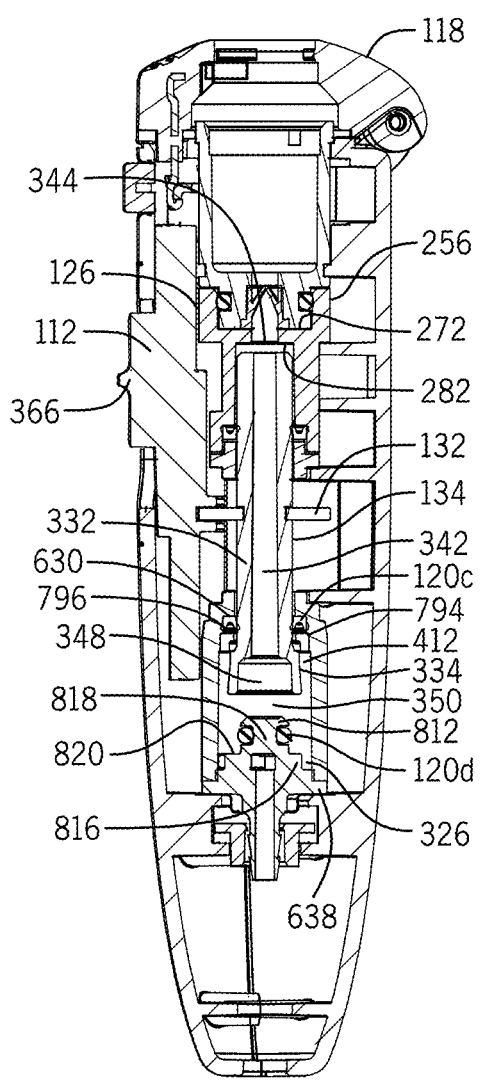
FIG. 5B
FIG. 5C

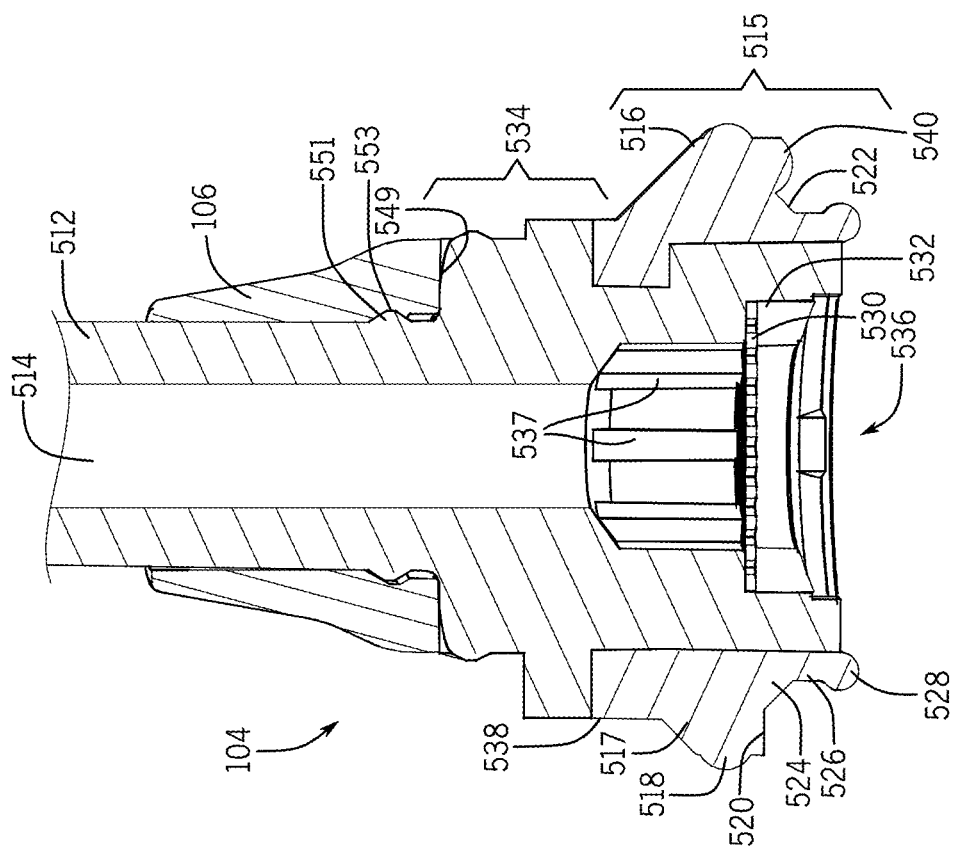
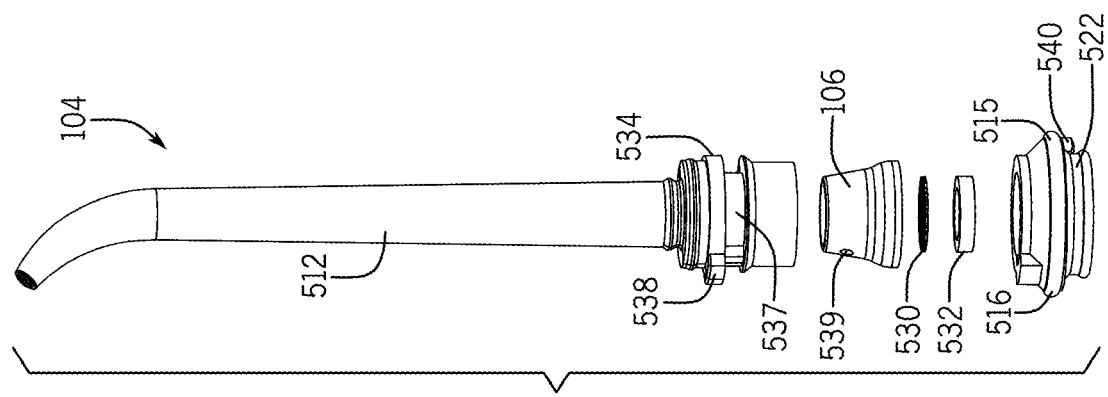
FIG. 7B
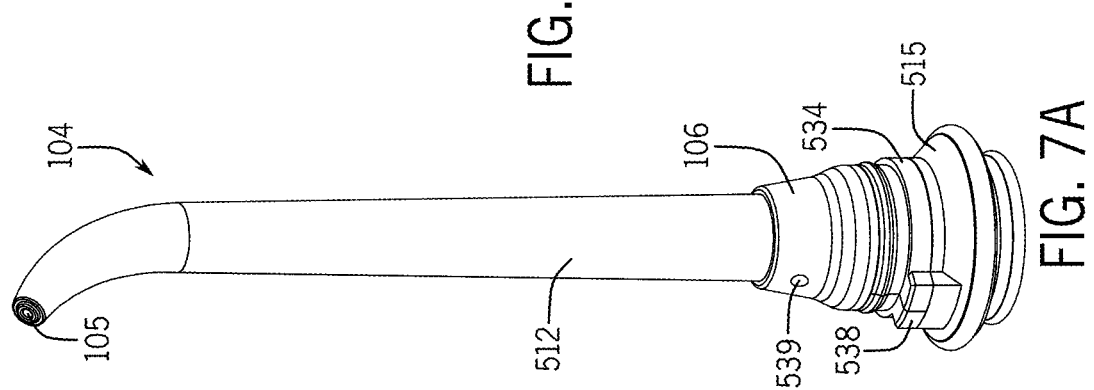
FIG. 7A
FIG. 7C

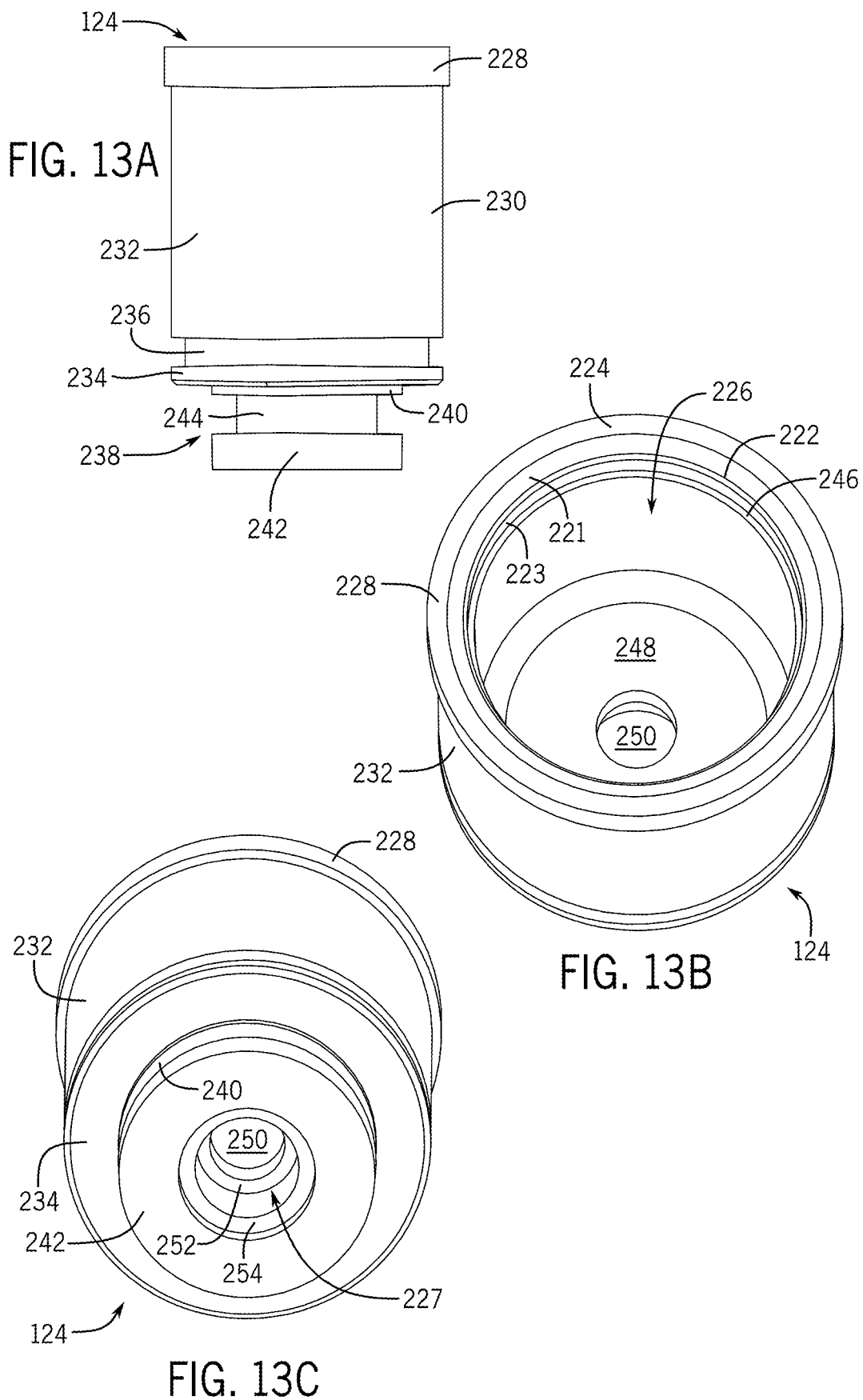

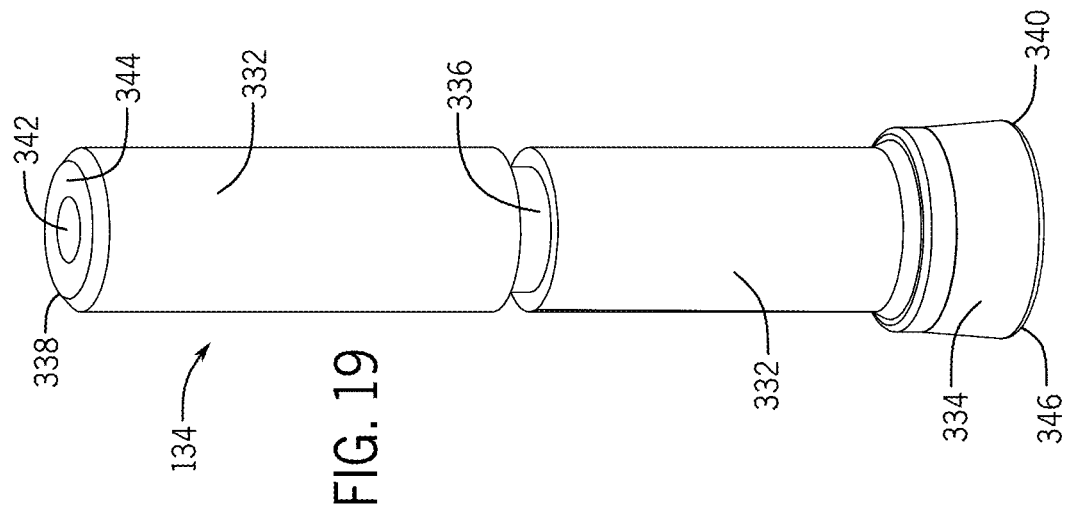
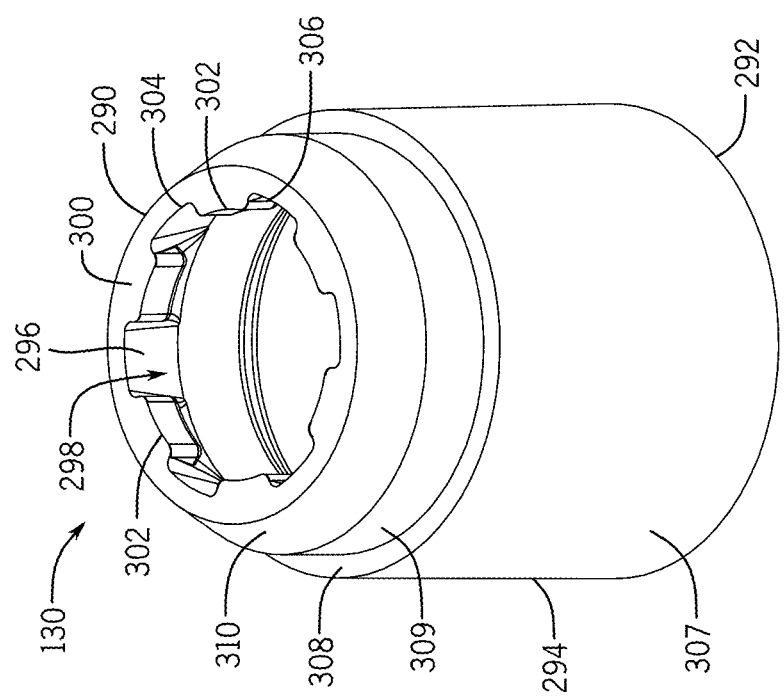

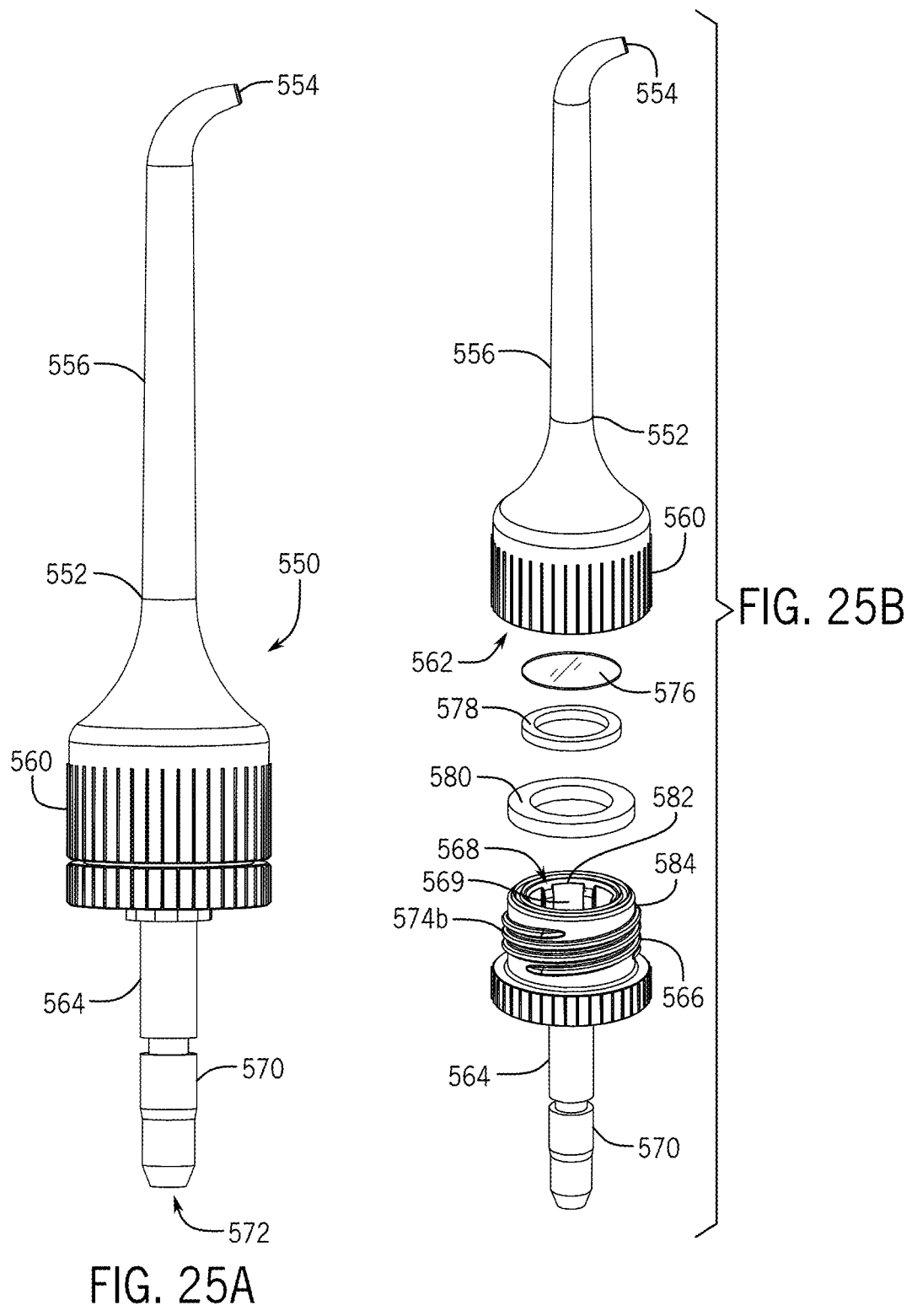

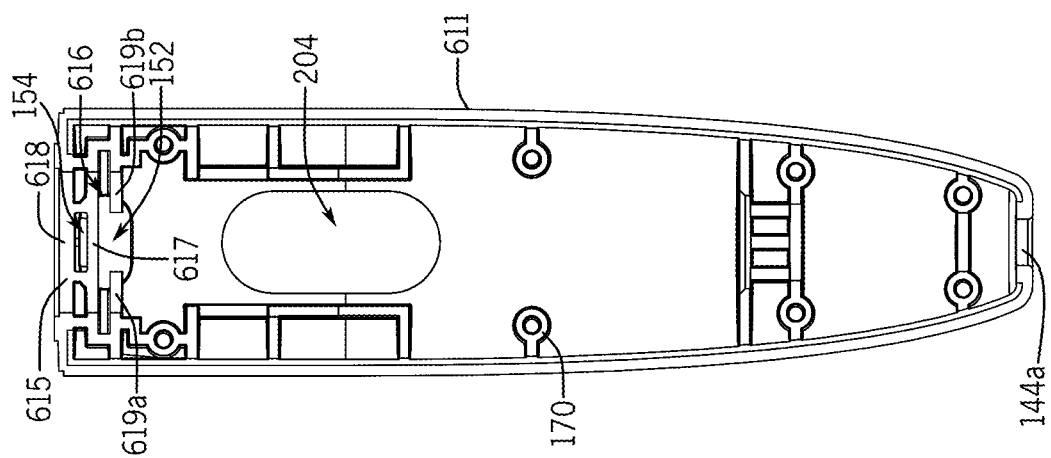
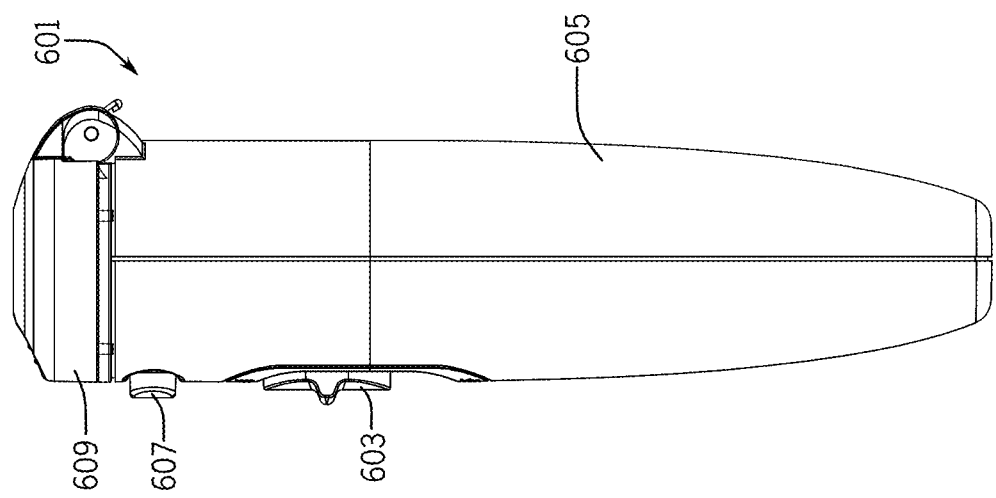
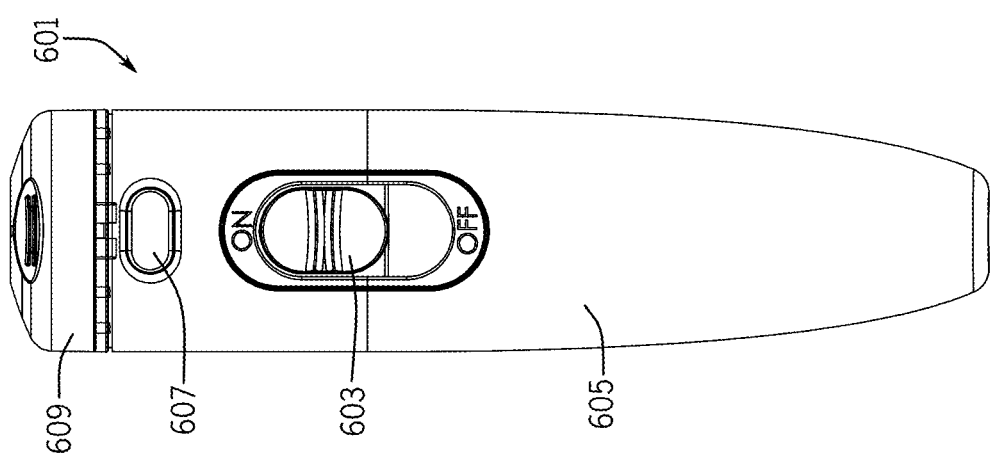

ORAL IRRIGATOR HANDLE FOR USE WITH ORAL AGENT

CROSS REFERENCE TO RELATED APPLICATIONS

The present application claims priority under 35 U.S.C. § 119 to U.S. Provisional Application No. 62/472,438 entitled "Oral Irrigator Handle for Use with Oral Agent," filed on Mar. 16, 2017 and U.S. Provisional Application No. 62/516,227 filed on Jun. 7, 2017 entitled "Oral Irrigator Handle for Use with Oral Agent," both of which are incorporated by reference, herein, in their entireties.

TECHNICAL FIELD

The present disclosure relates generally to health and personal hygiene equipment and more particularly, to oral irrigators.

BACKGROUND

Oral irrigators are used to clean a user's teeth and gums by discharging a pressurized fluid stream into a user's oral cavity. The fluid impacts the teeth and gums to remove debris. In some instances it may be desirable to add a supplemental agent to the fluid, in order to enhance the user experience and cleaning experience. However, many oral irrigators do not include features that easily integrate a supplemental agent into the fluid stream.

The information included in this Background section of the specification, including any references cited herein and any description or discussion thereof, is included for technical reference purposes only and is not to be regarded as subject matter by which the scope of the invention as defined in the claims is to be bound.

SUMMARY

An oral irrigator handle and tip for use with an oral hygiene agent are disclosed herein. The agent is received in a chamber positioned in the flow path such that fluid flowing through the handle impacts the agent and carries portions of the agent downstream towards a fluid outlet. A screen positioned between the chamber and the fluid outlet helps prevent larger portions or pieces of the agent from clogging the path to the outlet. An outlet valve upstream of the chamber helps prevent fluid that has contacted the agent from flowing towards the fluid source. In one exemplary embodiment, the chamber is positioned in the handle and a movable lid provides access to the chamber. In another exemplary embodiment, the chamber is positioned in a tip that is fluidly coupled to the handle.

In another embodiment, an oral irrigator is disclosed. The oral irrigator includes a housing having a fluid inlet and a fluid outlet and a chamber housing positioned within the housing between the fluid inlet and the fluid outlet, the chamber housing defines an agent chamber for receiving an oral agent therein. The oral irrigator also includes a lid pivotably coupled to the housing and in a closed position, the lid at least partially covers the agent chamber and in an open position, the lid uncovers the agent chamber.

In another embodiment, an oral irrigator device is disclosed. The oral irrigator device includes a pump in fluid communication with a reservoir, a handle in fluid communication with the pump, and a tip removably coupled to the handle. The handle also includes an agent housing defining an agent chamber, the agent housing including a chamber inlet and a chamber outlet in fluid communication with the agent chamber, a chamber valve positioned between the reservoir and the chamber inlet, and a cover coupled to the handle and positionable between an open position uncovering the chamber and a closed position at least partially covering the chamber. The tip, when coupled to the handle, is in fluid communication with the chamber outlet, such that fluid exiting the chamber, will flow into the tip.

In yet another embodiment, an oral hygiene system including the oral irrigator device and an oral agent tablet is disclosed. In this embodiment, the agent chamber has a chamber diameter that may be larger than the tablet diameter, such as by 20-30% larger. For example, in one embodiment, the table diameter is between 80 to 95% the length of the chamber diameter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 4A is a cross section view of the handle of FIG. 1B along line 4-4 in FIG. 2B.

FIG. 4B is a partial cross section view of the handle of FIG. 4A.

FIG. 5B is a cross section view of a handle according to another embodiment with a pause assembly activated.

FIG. 5C is a cross section view of the handle of FIG. 5B with a pause assembly deactivated.

FIG. 7A is a front isometric view of a tip for use with the oral irrigator handle.

FIG. 7B is an exploded view of the tip of FIG. 7A.

FIG. 7C is an enlarged cross-section view of the tip of FIG. 7A.

FIG. 13A is a front elevation view of a chamber body of the handle of FIG. 1B.

FIG. 13B is a top isometric view of the chamber body.

FIG. 13C is a bottom isometric view of the chamber body.

FIG. 18 is a top isometric view of a shuttle retainer of the pause valve assembly of FIG. 14A.

FIG. 19 is a front isometric view of a shuttle valve of the pause valve assembly of FIG. 14A.

FIG. 25A is an isometric view of a tip with an integrated oral hygiene agent chamber.

FIG. 25B is an exploded view of the tip of FIG. 25A.

FIG. 26A is a front elevation view of another embodiment of the oral irrigator handle.

FIG. 26 B is a side view of the oral irrigator handle of FIG. 26A.

FIG. 26C is a rear elevation view of a housing component of the oral irrigator of FIG. 26A.

DETAILED DESCRIPTION

Figure 1A:
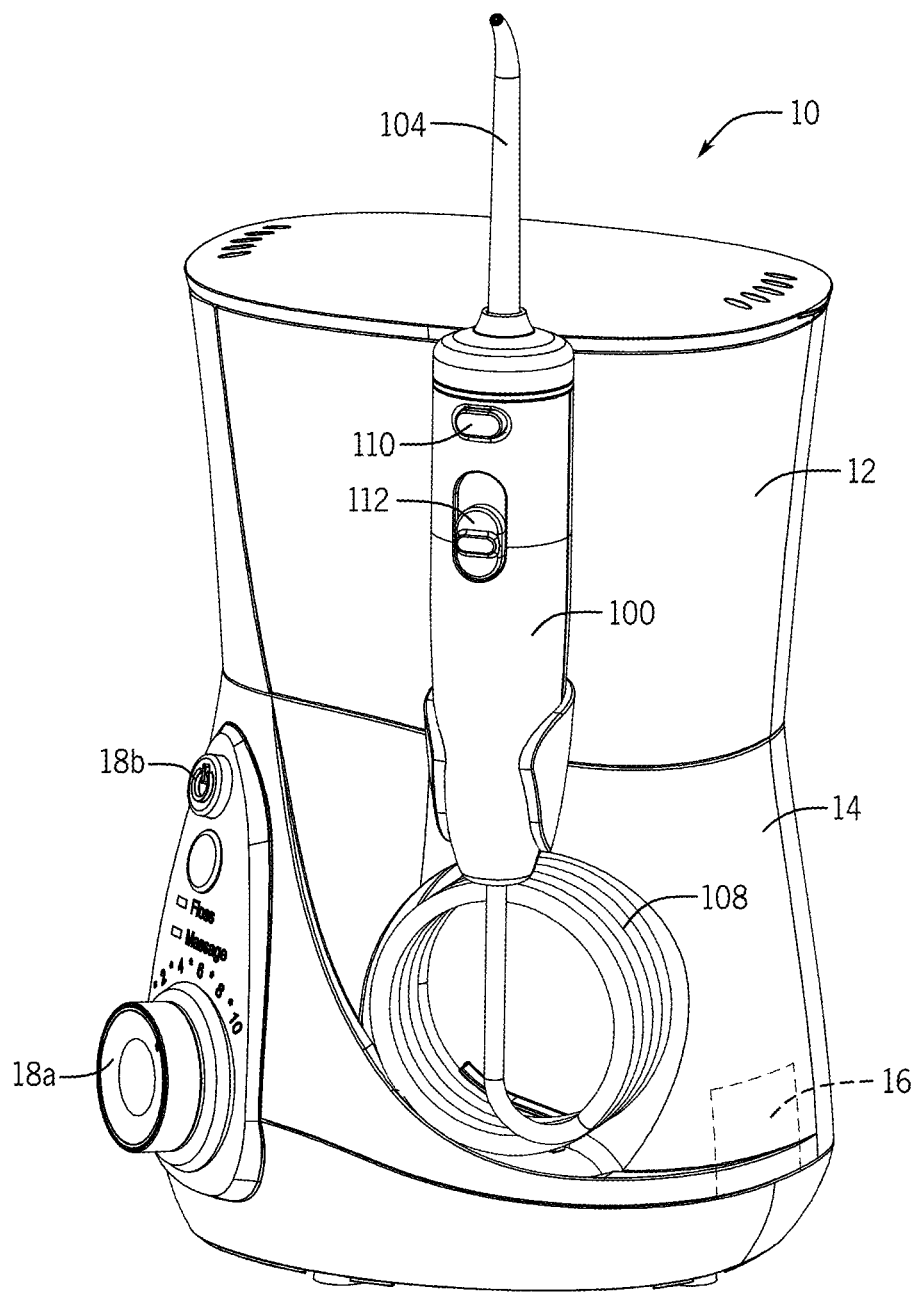
FIG. 1A is a front isometric view of an oral irrigator with integrated oral agent compartment.

The present application is generally directed towards an oral irrigator handle and system that can receive an agent, such as a tablet, pill, powder, gel, slurry, or the like, and dispense the agent into a user's oral cavity. The agent may be an oral hygiene agent or other type of additive that can be introduced into and travel with fluid. In one embodiment, fluid flows into the handle from a hose connected to a reservoir or base and into a chamber within the handle housing or within the tip and out the tip outlet. In another embodiment, the handle connects directly to the reservoir and forms a hand held oral irrigator. In either embodiment, when an agent is inserted into the chamber, the fluid flowing into the chamber acts to move the agent, particles of the agent, or otherwise mixes with the agent, to transport at least a portion of the agent along with the fluid through the tip and into a user's oral cavity. In some embodiments, the agent is a tablet, which is abraded by the fluid to loosen particles that travel within the fluid towards the user's gums and teeth. In these embodiments, the particles act as an abrasive or cleaning agent on the surfaces of the user's teeth and/or gums.

The agent chamber may be positioned at varying locations between the reservoir and the tip outlet, depending on the type of agent and/or tip being used. In some embodiments, the agent chamber is positioned within the handle, such as towards an upper end of the handle adjacent the tip insertion location. The agent chamber may include a lid or other member used to selectively access the chamber to allow a user to position the agent within the chamber and secure the agent within the chamber during use. The lid may include one or more sealing elements to ensure that the fluid and/or agent does not leak around the opening to the chamber. In some embodiments, the lid may include a latch that secures the lid to the chamber in the closed position and assists in sealing the perimeter of the opening to the chamber. The latch can be activated by a user to allow a user to place the oral agent into the chamber. In some embodiments, the enclosed chamber may be defined by an agent housing within the handle, as well as a lid for the handle, and a tip assembly connected to the lid. In this manner, the chamber will open to allow a user to insert the agent, by opening the lid.

In other embodiments, the agent chamber may be integrated into the tip itself and removable from the handle. In these embodiments, the agent chamber is positioned between a bottom end of the tip (which can be inserted into the handle) and a top end of the tip that provides an outlet into the user's oral cavity.

A screen or filter may be positioned over the outlet of the agent chamber. The screen helps to prevent the tip from clogging by ensuring that particles over a predetermined threshold size do not pass from the chamber to the tip. For example, in embodiments where the oral agent is a tablet, the screen may be sized to prevent large particles that break off from the tablet from passing through. Similarly, a check valve may be positioned between the inlet of the chamber and the hose to prevent the agent particles from traveling back into the handle, pump, or the like, that could cause damage to various components.

The oral irrigator may also include a pause valve for pausing fluid flow to the tip. In some embodiments, the pause valve may be positioned within the handle between the outlet valve of the agent chamber and the hose inlet to the handle. The pause valve is used to selectively stop fluid flow through the tip and allows a user to reposition the handle within his or her mouth without having to power off the oral irrigator.

In many instances, many of the components of the oral irrigator handle may be manufactured from plastic to reduce costs, increase manufacturability, reduce corrosion, and maintain an aesthetic appeal. However, in other embodiments, the components may be constructed out of other materials.

Components of the Oral Irrigator

Figure 1B:
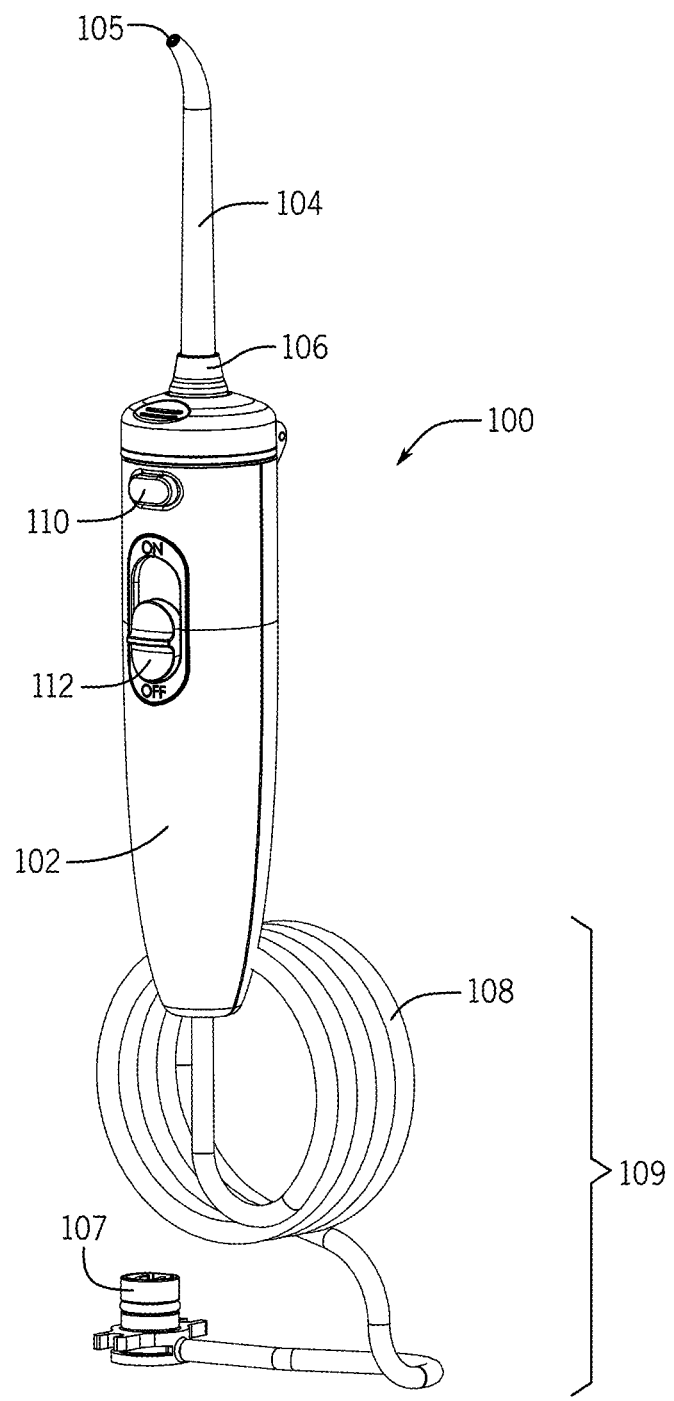
FIG. 1B is a front right isometric view of a handle of the oral irrigator of FIG. 1A.
Figures 2A, 2B:
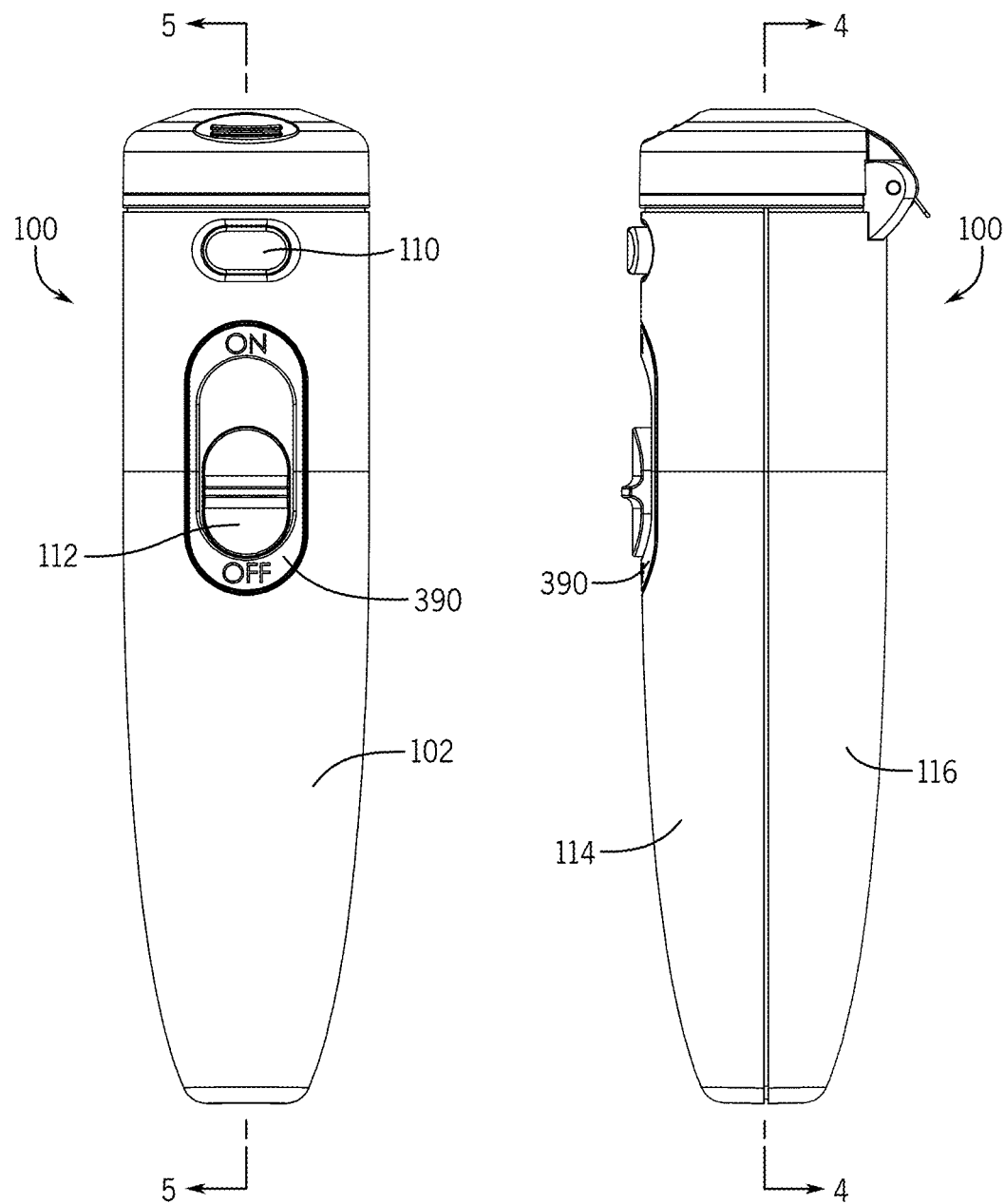
FIG. 2A is a front elevation view of the handle of FIG. 1B.
FIG. 2B is a right elevation view of the handle of FIG. 1B.

Turning to the figures, an oral irrigator including a chamber for an oral hygiene agent will now be discussed in more detail. FIG. 1A illustrates an isometric view of an oral irrigator including a handle with an agent chamber. FIG. 1B is an isometric view of the handle of FIG. 1A. It should be noted that in some embodiments, the chamber may be positioned upstream of the reservoir and downstream of the tip outlet.

With reference to FIGS. 1A and 1B, the oral irrigator 10 may include a handle 100, a reservoir 12, a base 14, and a hose 108, all of which may be interconnected together. The base 14 may include a pump 16 fluidly connected to the reservoir 12 that pumps fluid from the reservoir 12 to a tip 104. One or more controls 18a, 18b are coupled to the base and configured to vary a flow rate or a fluid pressure produced by the pump 16, and/or may activate a particular mode, e.g., cleaning mode, produced by the pump 16. The base 14 and pump 16 may be similar to the base and pump illustrated in U.S. Publication No. 2015/0004559 entitled "Oral Irrigator with Integrated Lid and Base," filed on Mar. 13, 2014, which is incorporated herein by reference in its entirety. In other embodiments, the handle may enclose the pump and other components and connect directly to the reservoir, in these embodiments, the handle main form a main housing for the device. The reservoir and pump in the handheld version may be similar to those shown in U.S. Pat. No. 7,147,468 entitled "Hand Held Oral Irrigator," granted on Dec. 12, 2006 and incorporated by reference herein in its entirety.

The Handle

The handle 100 is fluidly connected to the pump 16 and reservoir 12 and can be held by a user to direct fluid into the user's mouth. With reference to FIGS. 1B-3, the handle 100 may generally include a housing 102, a tip 104, a cover assembly 122, an agent assembly 123, a pause valve assembly 142, a swivel assembly 143, and fluid connectors 109, each of which are discussed in turn below.

The fluid connectors 109, such as the hose 108 and fluid fitting 107, fluidly connect the handle 100 to the reservoir 12. However, in instances where the irrigator is a handheld unit, the fluid fitting 107 and/or hose 108 may be omitted or may be varied as the reservoir 12 may be directly connected to the handles.

The tip 104 is connected to a top end of the handle 100 and may be removable from the handle 100 or integrated therewith. The tip 104 is configured to be inserted into a user's mouth and to expel fluid, as well as the agent, against a user's teeth, gums, tongue, etc. For example, the tip 104 may include a nozzle shaped outlet 105 at the end to expel a jet of liquid. It should be noted that the tip outlet 105 may be varied in shape depending on the desired fluid stream, as well as the type of agent that may be used with the oral irrigator unit 10 (e.g., the outlet 105 size may increase in instances where the agent includes solid particles as compared to instances where the agent is a liquid or gel). The tip is discussed in more detail below with respect to FIGS. 7A-7C.

With reference to FIGS. 2A-6B, the handle housing 102 will now be discussed in more detail. The handle housing 102 may be an integrated component or as shown in FIGS. 2A-6A, may include a first shell 114 and a second shell 116 coupled together (e.g., through ultrasonic welding, fasteners, adhesive, or the like). Each of the first and second shells 114, 116 may be constructed of a rigid material that resists deformation, such as a hard plastic, but it should be noted that various other materials may be used as well. Additionally, the handle housing 102 may include an aesthetically pleasing shape that may conform to a user's hand and may include one or more gripping elements.

Figure 6A:
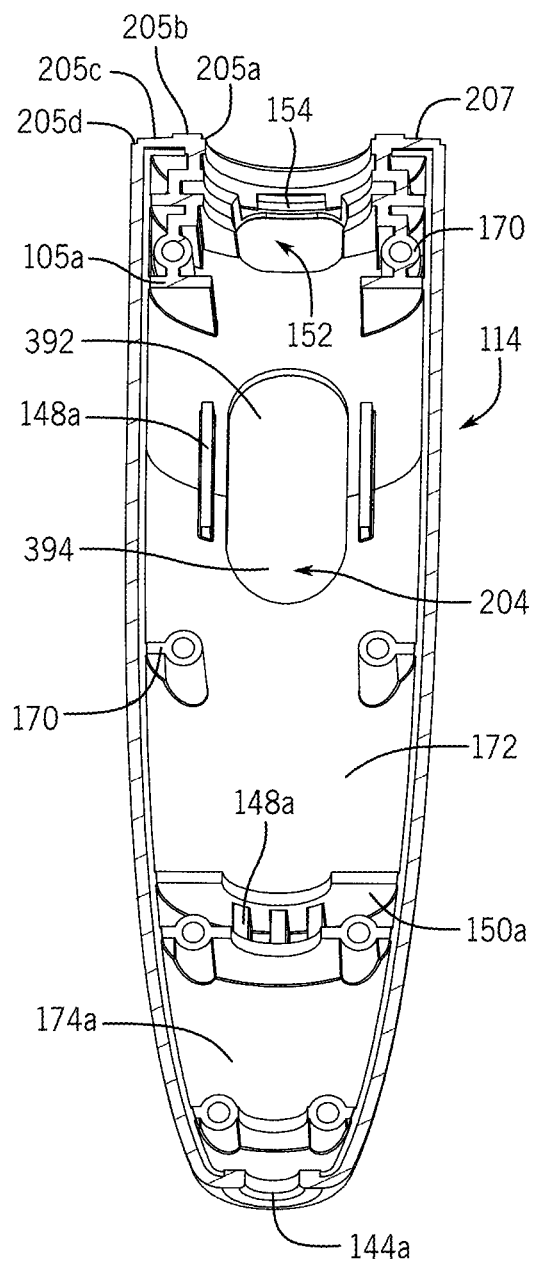
FIG. 6A is a rear isometric view of a first shell of the handle of FIG. 1B.
Figure 6B:
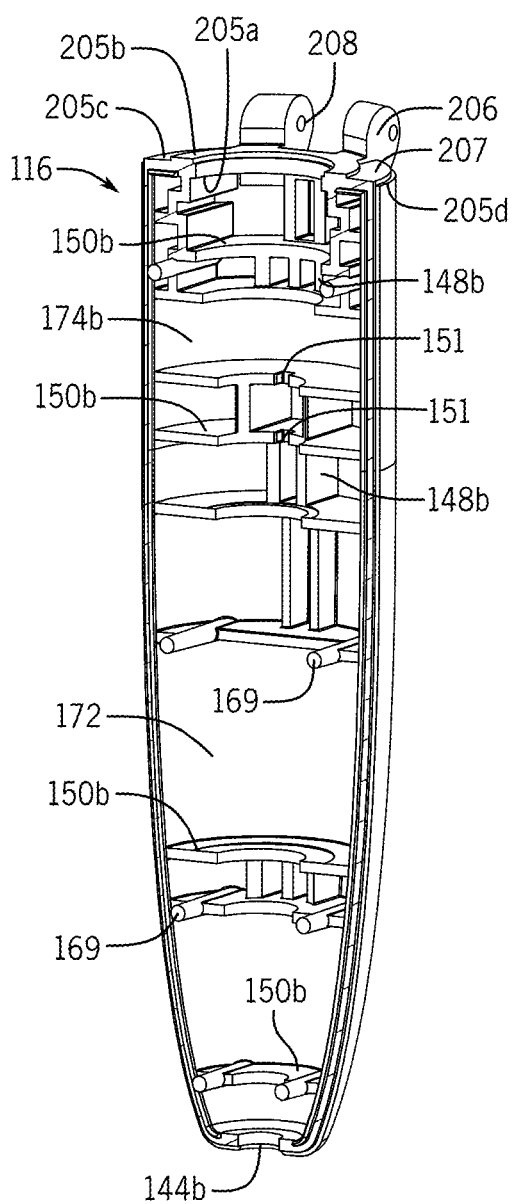
FIG. 6B is a front right isometric view of a second shell of the handle of FIG. 1B.

With reference to FIGS. 6A and 6B, when connected together, the first and second shells 114, 116 define a handle cavity 172 in which components of the handle 100, such as the cover assembly 122, pause valve assembly 142, swivel assembly 143, and a portion of the hose 108, reside. To this end, each of the first and second shells 114, 116 may include a plurality of structural features for aligning, receiving, retaining, and/or supporting components of the handle 100 within the handle cavity 172. The features may include ledges 150a, 150b, vertical support walls 148a, 148b, and pegs 169. The ledges 150a, 150b may generally extend outwardly from an interior wall 174a, 174b of the first or second shell 114, 116 so as to extend into the handle cavity 172. Pairs of ledges 150a, 150b in each shell 114, 116 are configured to align with one another to define the structural features when the handle 100 is assembled. For example, ledges 150a of the first shell 114 may align with a mating ledge 150b of the second shell 116 when the handle 100 is assembled.

With continued reference to FIGS. 6A and 6B, one or more pegs 169 may extend from the interior wall 174 of one of the shells 114, 116 (e.g., in the depicted embodiment, the second shell 116). Each peg 169 may extend beyond a plane defined by a circumferential edge of the first shell 114 and be adapted to mate with a corresponding boss defining an aperture 170 of the opposing shell 114, 116. The pegs 169 and the apertures 170 may be dimensioned such that each peg 169 will fit snugly within its corresponding hole 170. The friction resulting from this fit may resist decoupling of the shells 114, 116, as well as assisting in alignment of the shells 114, 116 during manufacture. Alternatively and/or additionally, the first and second shells 114, 116 may be joined using glue, epoxy, fasteners, ultrasonic welding, any other known method for joining two items, or by a combination of known methods.

Figure 24A:
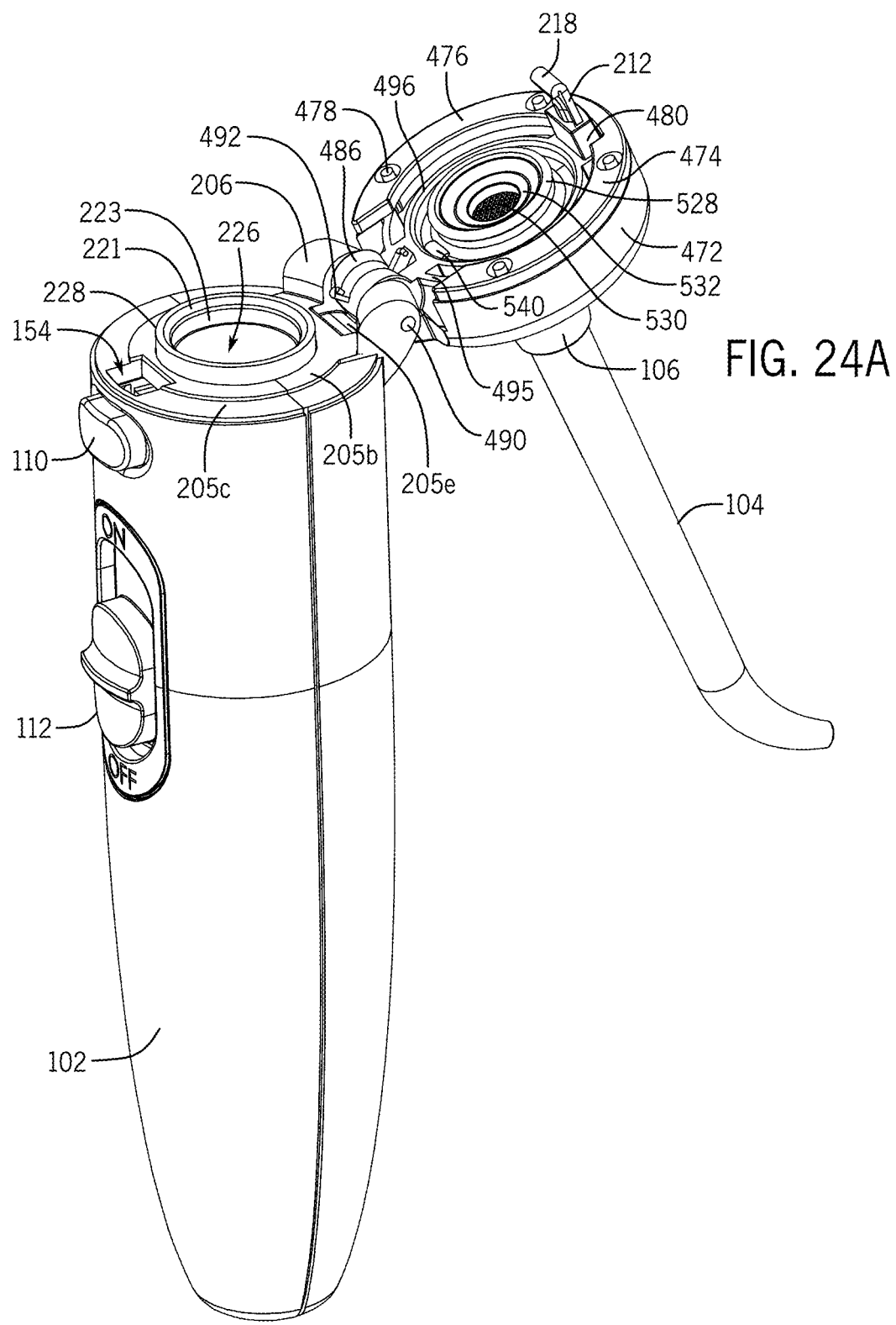
FIG. 24A is a front right isometric view of the handle of FIG. 1B with the lid in an open position.
Figure 24B:
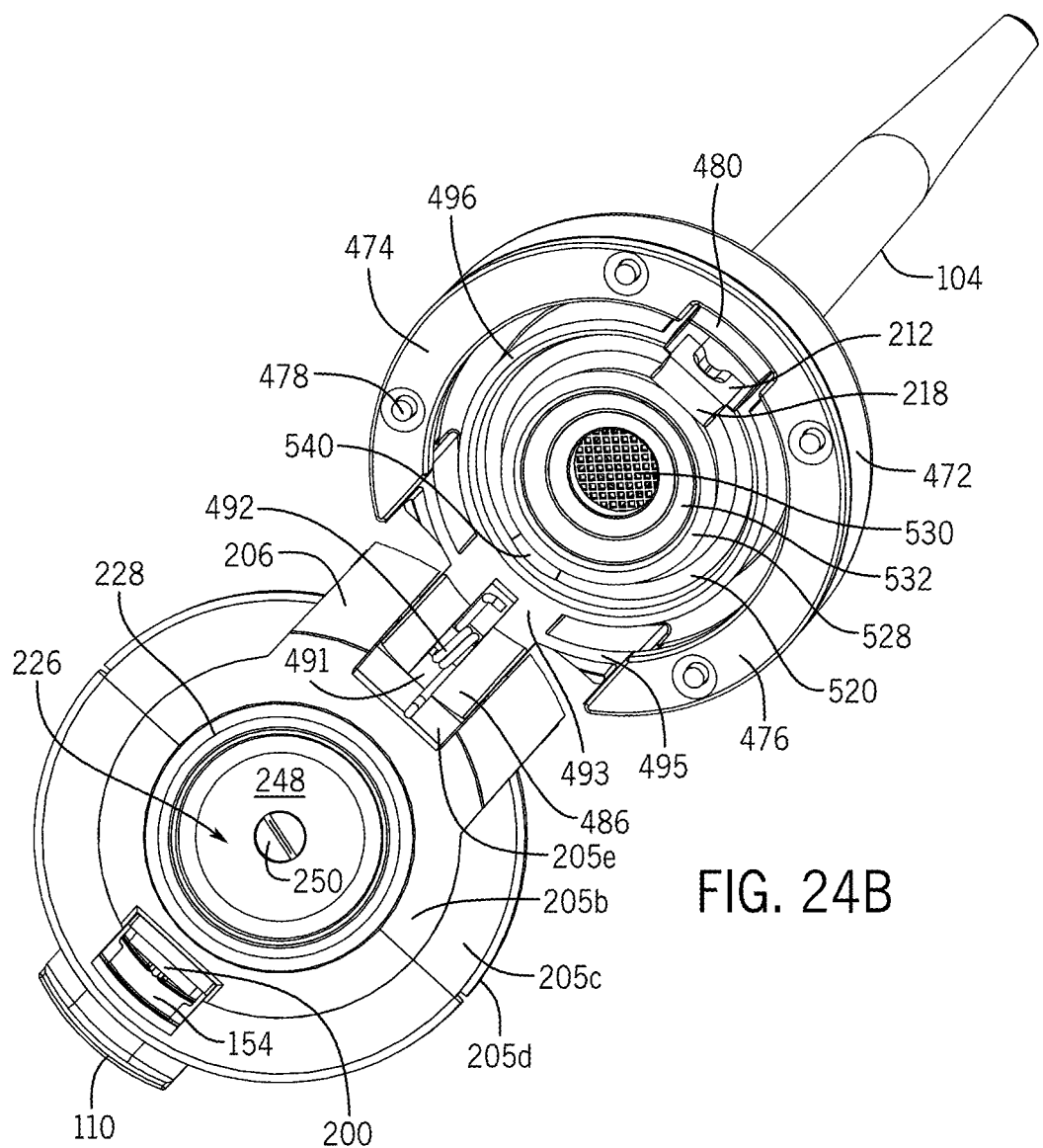
FIG. 24B is a top plan view of the handle of FIG. 24A.
Figure 25C:
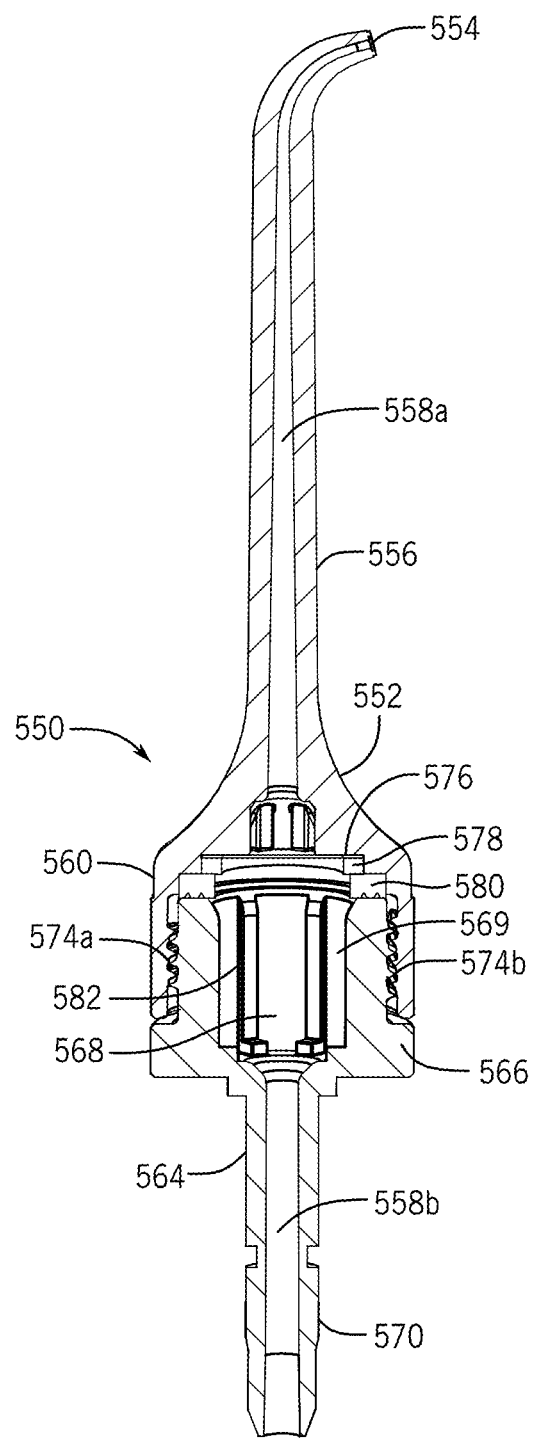
FIG. 25C is a cross-sectional view of the tip of FIG. 25A.

With reference to FIG. 6A, the first shell 114 may include various apertures and/or recesses for buttons and latches of the handle. For example, the first shell 114 may include a button aperture 152 for receiving a latch button 110. As shown in FIG. 6A, the button aperture 152 is oval-shaped, but may be any shape configured to correspond to the shape of the latch button 110. When the handle 100 is assembled, the latch button 110 is received within the button aperture 152. With reference again to FIGS. 2A and 6A, the first shell 114 may also include a pause actuator aperture 204 for receiving a pause actuator 112 and a recessed pause actuator frame 390. The pause actuator aperture 204 and actuator frame 390 generally corresponds to the shape of the pause actuator 112 and in some embodiments may be oblong or oval-shaped and elongated along the longitudinal axis of the handle, having an upper portion 392 and a lower portion 394. With reference to FIGS. 6A, 24A, and 24B, a catch aperture 154 for receiving a latch catch 212 may be defined in the first shell 114, in some embodiments, the catch aperture 154 may be positioned directly above the button aperture 152 or even formed within the button aperture (see FIG. 26C) and both may be positioned towards a top end of the handle shell 114. The positioning of the latch, button, and catch apertures may be varied as desired and to correspond with the latch and pause assemblies.

With reference to FIGS. 6A and 6B, an upper surface 207 of each of the first and second shells 114, 116 may include one or more ledges or steps 205a, 205b, 205c, 205d, 205e that receive and mate with various components of the agent assembly 123 and/or the cover assembly 122, such as a lid 118, a trim ring 474, or a spring 492. The steps 205a, 205b, 205c, 205d, 205e provide structural support to various components and may be shaped and dimensioned as desired.

With reference to FIG. 6B, the second shell 116 is generally substantially similar to the first shell 114, but may include one or more hinge features, such as posts or knuckles 206 that allow the cover assembly to connect and rotate relative thereto. In one embodiment, the knuckles 206 extend upwards and rearwards from an upper surface 207 of the second shell 116 and are spaced laterally apart from one another. The knuckles 206 may define a pin aperture 208, oriented approximately parallel to the plane of the upper surface 207, therethrough. As will be discussed in more detail below, the knuckles 206 interface with a hinge assembly 485 used to connect a lid 118 to the second shell 116. The knuckles 206 may be formed integrally with the shell or formed as separate components and connected to the shell.

With reference again to FIGS. 4-6B, the first and second shells 114, 116 may each terminate in a hose cut-out 144a, 144b, which in some embodiments may be semi-circular or otherwise configured to configure to the outer shape of the hose 108. When the first and second shells 114, 116 are assembled to form the housing 102, the cut-outs 144a, 144b together define a hose aperture 146 through which the hose 108 passes.

Lid and Cover Assembly

Figure 8A:
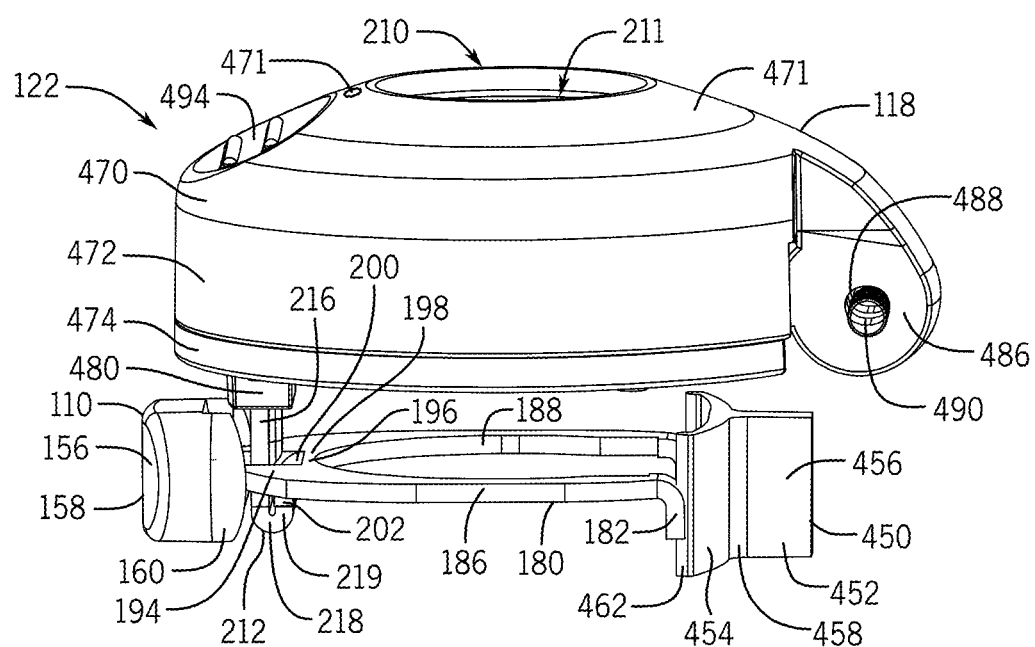
FIG. 8A is a right elevation view of a cover assembly of the handle of FIG. 1B.
Figure 8B:
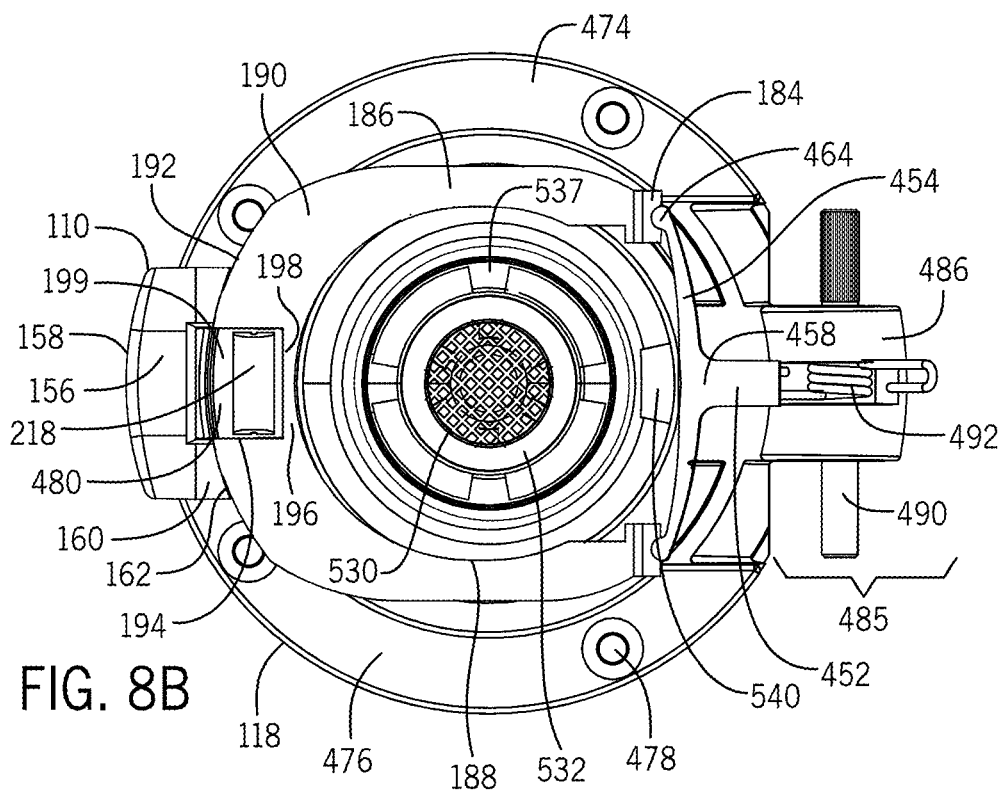
FIG. 8B is a plan view of the cover assembly of FIG. 8A with a tip inserted therein.

With reference to FIGS. 8A and 8B, a cap, lid, or cover assembly 122 will now be discussed in more detail. The cover assembly 122 provides access to at least a portion of the agent assembly 123 and also may secure the tip 104 to the handle 100. The cover assembly 122 may include a lid 118 or cover, an access or latch button 110, a latch catch 212, a latch 180, a latch spring 450, and a hinge assembly 485 each of which is discussed below.

Figure 9:
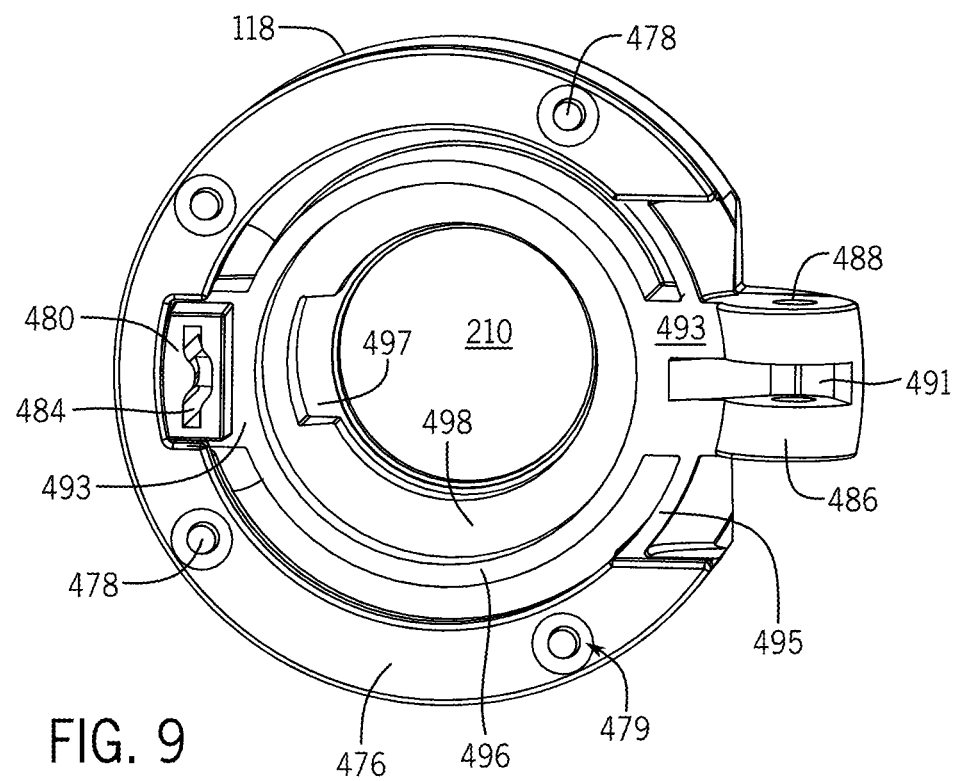
FIG. 9 is a bottom isometric view of a lid of the cover assembly of FIG. 8A.

With reference to FIGS. 8A and 9, the lid 118 covers the agent assembly 123 to help seal the assembly when closed and provide access when open. The lid 118 may include a body 472 positioned between a crown 470 and an optional trim ring 474. The crown 470 forms an upper portion of the lid 118 and may have a grip portion 494 that may include optional ribs, bumps, or the like, on its upper surface 471, to help a user more easily grip the lid 118 to open and close it. The grip portion 494 may be formed as a recess or depression on the top-front surface of the lid 118 to assist a user in locating, as well as pressing the lid. Alternatively or additionally, the grip portion 494 may include a rubberized or other increased friction material to further assist a user in gripping the lid 118.

A tip-receiving aperture 210 is defined through a top surface of the crown 470 and provides access to a tip cavity 211 formed through the crown 470 and the body 472. The tip receiving aperture 210 may be sized to receive a tip therethrough.

With reference to FIG. 9, the interior surface of the lid body 472 may include an outer rim 495 and an inner rim 496. Each rim 495, 496 may extend from at or near the upper surface 471 downwards towards the trim ring 474. The outer rim 495 and inner rim 496 may be joined at one or more bridges 493 or strengthening ribs. The various rims may be used to conform to various portions of the agent assembly 123, such as the chamber and/or sealing members. The rims act to provide structural support for the lid 118, as well as assist in mating with and sealing with various portions the agent assembly 123.

The interior surface of the lid body 472 may also define an annular ledge 498 near the upper surface 471 and internal to the inner rim 496. A tip alignment notch 497 may be defined in the ledge 498 and may be positioned approximately beneath the grip portion 494.

A clasp housing 480 may extend downwards from the bridge 493 past the trim ring 474. The clasp housing 480 receives a portion of the latch catch 212, to secure the catch 212 to the lid and allow it to move therewith as discussed in more detail below. In some embodiments, the clasp housing 480 is positioned on the same side of the lid 118 as the notch 497 and the grip portion 494. A clasp slot 484 may be defined in the clasp housing 480 and may be shaped and sized to correspond to the latch catch 212.

A hinge body 486 extends from a rear sidewall of the lid 119 and may be positioned generally opposite the grip portion 494. As discussed below, the hinge body 486 interfaces with the knuckles 206 to connect the lid 118 to the second shell 116. The hinge body 486 may have a channel 488 or pin aperture defined therethrough for receiving a pin 490. In some embodiments, a spring recess 491 may be defined in the hinge body 486 and bridge 493 and configured to receive one or more portions of the hinge assembly (see e.g., FIG. 8A).

The trim ring 474 enhances the aesthetic appearance of the handle 100 and can be used to correspond to different users (e.g., with different colors). The trim ring 474 may be positioned adjacent to the outer rim 495 and may be secured to the body 472 by pegs 478 extending from the outer rim 495 through holes 479 to a bottom surface 476 of the trim ring 474. In some embodiments, the trim ring 474 may be omitted.

The hinge assembly 485 couples the handle housing 102 to the lid 118 and allows the lid 118 to rotate relative the housing 102. The hinge assembly 485 may include a biasing element 492, such as a torsion spring, leaf spring, or the like, and a pin 490 or other securing element.

Figure 10:
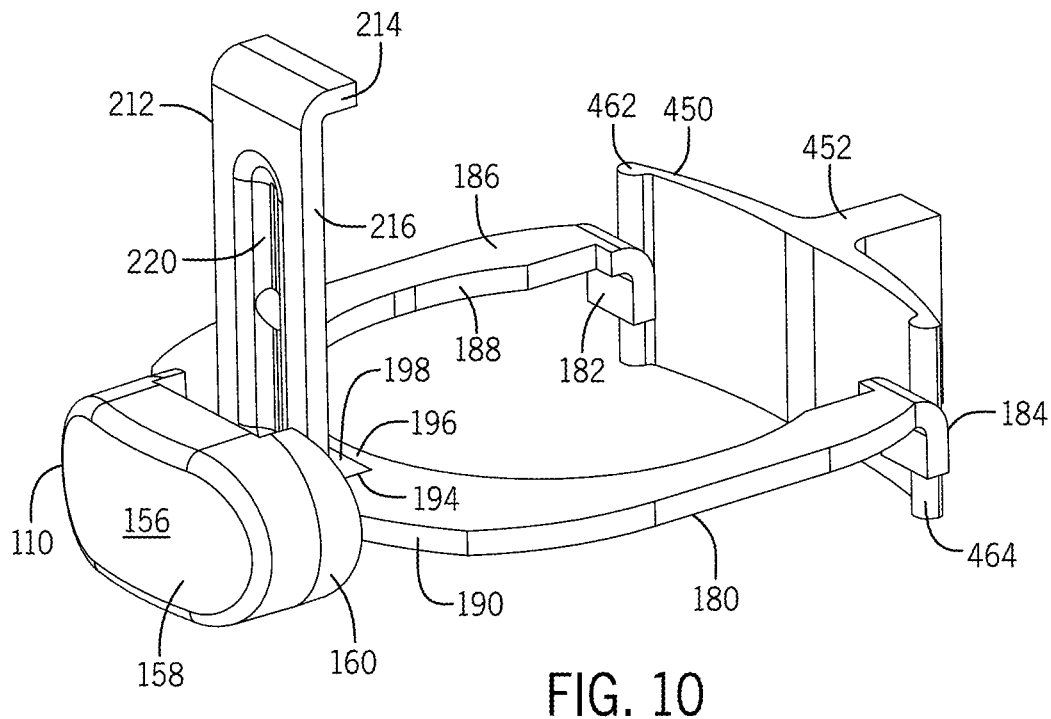
FIG. 10 is a front right isometric view of select components of the cover assembly of FIG. 8A.
Figure 11:
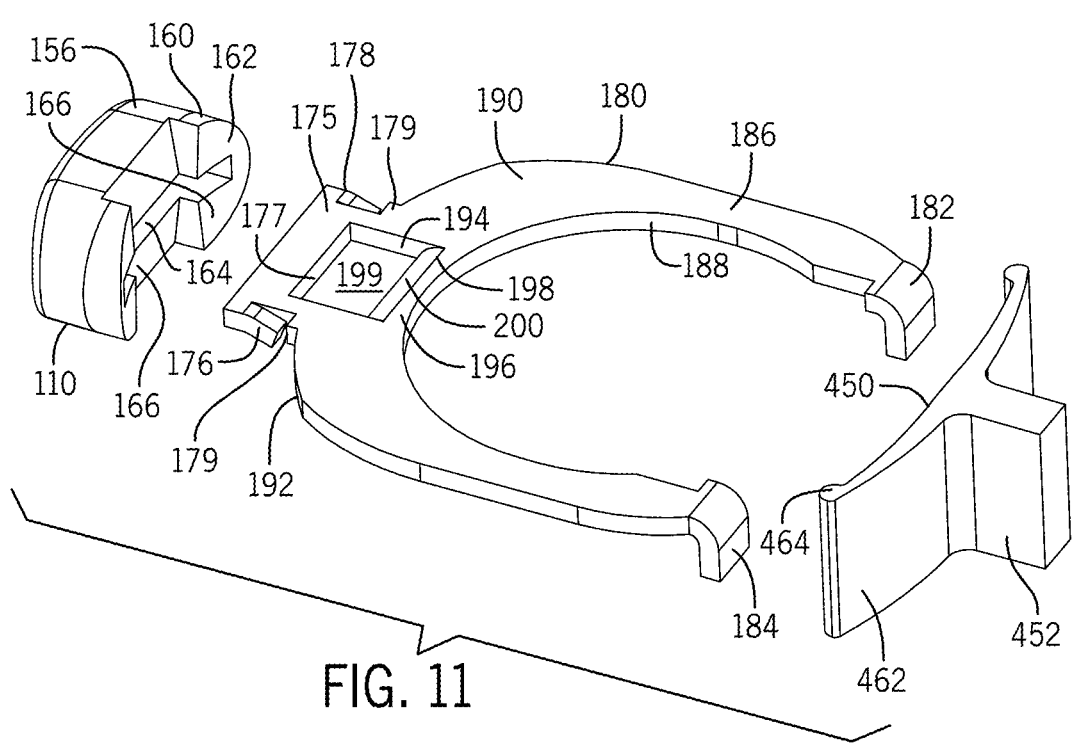
FIG. 11 is a rear right exploded view of select of the cover assembly of FIG. 8A.

With reference to FIGS. 8A, 10, and 11, the latch button 110 activates the cover assembly 122 to open or close the cover 118 of the agent chamber 124 and/or handle. The latch button 110 is shaped and sized to be activated by a user's finger and may include a generally oval-shaped body 156 having a convexly curved exterior surface 158 and an opposing interior face 166 having two arms 160 or protrusions extending therefrom. The arms 160 may be blunted angled surfaces and each arm 160 may end in an angled or curved terminus 162 that approximates the curvature of the exterior surface 158 of the body 156 of the latch button 110. A plate slot 164 is defined in the interior face 166 of the body 156 and arms 160, extending along a width of the button 110.

With reference to FIGS. 8A, 8B, 10, and 12, the latch catch 212 engages the handle 110, such as the handle housing, to secure the lid 118 to the housing 102. The latch catch 212 may include a catch body 216 that may be vertically elongated, an anchoring shelf 214 that may extend approximately perpendicularly from an upper end of the body 216, and a hook or catch seat positioned at the opposing end or lower end of the body 216. The hook 218 may curve 180 and terminate at an end 219. The top end face 219 of the hook 218 or engagement feature may be shaped to engage and selectively release from the respect element on the housing or latch. Similarly, the bottom face of the hook 218 may be formed to more easily engage and disengage from the securing element or the latch (see, e.g., FIG. 30).

A well 220 or depression may be formed in the catch body 216 and may extend a majority of the distance between the anchoring shelf 214 and the hook 218. In some embodiments, the well 220 may be substantially oval-shaped and extend a substantial length of the catch body 216. The well 220 may help to reduce the amount of material required for the catch, thus saving manufacturing costs. The latch catch 212 typically may be configured to withstand high stresses and repeated use and therefore may be formed of a strong material, such as metals, alloys, or the like. The latch catch 212 may be formed via metal injection, machining, stamping, or other suitable manufacturing processes.

With reference to FIGS. 8A, 10, and 11, latch 180 is connected to the housing 102 and engages the latch catch 212 to releasably secure the lid 118 to the housing 102. In some embodiments, the latch 180 may be a generally planar element having a U-shape with two arms 186 extending approximately parallel to each other from shoulders 190 joined by a neck 196. An inner wall 188 of the latch 180 forms the inner wall of each of the arms 186 and may define a concavely curved wall. The width between the arms 186 may be sufficient to accommodate the chamber 124 when the handle 100 is assembled.

The latch 180 may include a coupling head 175 extending from the neck 196 and the shoulders 192. The coupling head 175 or securing prong engages the latch button 110 to couple the button 110 and latch 180 together, such that movement of the button 110 moves the latch 180 correspondingly. The coupling head 175 may be varied as desired to secure to the button 110. In some embodiments, a tab clip 176 may be positioned at each lateral end 178 of the head. In some embodiments, the tab clips 176 may be angled downward below the plane of the arms 186 and may flex to allow the button 110 to be inserted onto the coupling head 175 and then secured thereto.

A clasp aperture 199 is defined through a top surface of the latch 180, such as by an inner wall 194 of each shoulder 190, an inner wall 198 of the neck 196, and an inner wall 177 of the coupling head 175. A clasp surface 200 is angled from the top surface of the latch 180 and extends downwards from the inner wall 198 of the neck 196 downward such that an end 202 of the clasp surface 200 is positioned below the plane of the arms 186. The clasp tab or surface 200 may be shaped and positioned to engage with the end 219 of the hook 218 of the latch catch 212. In other words, the clasp surface 200 may be formed as a securing feature to engage the clasp of the lid. The angle of the clasp surface 200 may be selected to retain the hook 218 while allowing the hook 218 to easily engage and disengage.

The latch 180 may also include one or more steps 179 positioned at the neck 196 between the coupling head 175 and each shoulder 190, and a top wall 192 of each shoulder 190 may curve from each step 179 to each arm 186. The steps 179 act as a stop or catch for the button 110 to ensure that the button 110 will actually translate the latch 180 and not just slide relative to the latch 180 when activated. The shape of the end walls 192 may complement the shape of the termini 162 of the arms 160 of the latch button 110.

Each latch arm 186 may extend in a similar direction to one another and may terminate in an actuator surface 182 that transitions to define an engagement surface 184 that maybe substantially perpendicularly relative to the plane of the arms 186. The latch arms 185 may be curved and having a curvature corresponding to the shape of the chamber, to allow the arms to move horizontally relative to the chamber unimpeded. In one example, the actuators 182 may include a curved surface as it transitions to define the engagement surface 184 perpendicular to the latch arms 186. The engagement surfaces 184 of each foot 182 transmits force to the latch spring 450 as discussed below.

In some embodiments, the latch 180 may be a metal or alloy material for increased strength and durability. In these embodiments, the lath may be created by metal injection molding, but may also be manufactured by stamping or machining.

With reference to FIGS. 8A, 8B, 10, and 11, the latch eject or latch spring 450 maintains and returns the latch 180 to an engagement position where the latch 180 engages the latch catch 212. The latch spring 450 may be a generally flexible component that deforms upon application of a force and springs back to its original shape when the force is removed. In some embodiments, the latch spring 450 may have a generally curved body and may include a spine 452 or securing protrusion extending outwards from a back surface. The spine 452 may extend along the entire height of the latch spring 450 and anchors the spring 450 to the housing 102. The two terminal ends 462 of the latch spring 450 include engagement nubs 464 that may extend along the height of the spring 450.

Agent Assembly

The handle 100 includes an agent assembly 123 that receives and stores one or more oral agents for dispensing with the fluid. The agent assembly 123 may include one more chambers or cavities, as well as optional filtering features that regulate the dispensing of the agent. With reference to FIGS. 3 and 12-13C, the agent assembly 123 will now be discussed in more detail. The agent assembly 123 receives and contains one or more oral agents to be delivered to a user's oral cavity and may include an agent chamber 124, one or more filters 530, and a chamber valve 500, each discussed in turn below.

With reference to FIGS. 13A-13C, the chamber 124 defines an agent compartment or cavity to receive and introduce the oral hygiene agent into the fluid stream. The chamber 124 may be generally cylindrically shaped and include a rim 228, a chamber body 230, and a connection base 238, each of which may be shaped to correspond to the handle shells 114, 116 and/or pause assembly. Additionally, the chamber 124 is shaped based on the desired oral agent for delivery by the handle 100 and in some instances may be configured to receive a round tablet.

The rim 228 defines and upper surface 224 of the chamber 124 and may define an angled interior wall 222 having a sloped portion 221 positioned between the upper surface 224 of the rim 228 and the shelf 246. The sloped portion 221 may assist in insertion of the tip assembly into the agent assembly 123. A shelf 246 may be formed on the interior of the chamber body 230 near the interface between the rim 228 and upper portion 232 of the body 230.

The chamber body 230 may include an upper body 232 joined to a lower body 234 by a recessed neck 236. The lower body 234 may include a beveled bottom edge that interfaces with portions of the pause assembly. An agent chamber 226 or cavity is defined within the chamber body 230 and is fluidly connected to the reservoir via a chamber aperture 250 defined in a bottom wall 248 of the chamber body 230.

In some embodiments, the agent chamber 226 has a diameter Dc, that approximately matches in an almost 1:1 ratio an oral agent diameter to be used with the device. For example, the oral agent may have a diameter Dt, that is between 80 to 98 percent of the length of Dc. In one embodiment, the tablet diameter Dt may be 93.6 percent of the chamber diameter Dc. This allows the tablet to be easily positioned within the chamber by a user, e.g., a user does not need to press fit the tablet into the chamber 226, but helps to prevent the tablet from flipping over itself within the chamber 226 such that an edge of the tablet 590 is ensured to be ablated by the fluid stream entering the chamber. In one embodiment, the chamber diameter is also selected to ensure that the fluid pressure within the chamber 226 does not exceed the latch strength for the lid. For example, as the diameter of the chamber Dc increases, the fluid pressure on the lid 118 and latch 180, will increase, which could cause the latch to fail or otherwise require increased strength. In one embodiment, the diameter of the chamber Dc is selected to range between 0.400 and 0.600 inches, 0.400 and 0.500 inches, and in a specific embodiment, between 0.470 inches. In this embodiment, the tablet 590 may be selected to have a corresponding diameter between 0.300 to 0.599 inches, and in a specific embodiment, 0.440 inches across a longest dimension.

The chamber 226 may also have a height selected to allow multiple tablets to be positioned within (e.g., stacked) the chamber and/or to allow taller tablets to be used. The height of the chamber may be varied, depending on a desired length of the handle, as well as the tablet or agent height.

The flow aperture 250 or chamber inlet 250 is defined through a bottom wall of the chamber 226 and may have a diameter less than the diameter of any of the rim 228, body 230, and base 238 to permit the agent chamber 226 to receive an oral hygiene agent while preventing the agent from moving out of the chamber 226 through the flow aperture 250. The chamber inlet 250 may be arranged in a center of the chamber to ensure that the incoming fluid stream will hit a central region of the tablet or other agent used within the chamber.

The connection base 238 of the chamber 124 extends from the bottom end of the chamber body 230 and defines an inlet to the chamber 123. The connection base 238 may define a fluid path therethrough that is fluidly connected to the flow aperture 250 in the chamber body 230. The connection base 238 is configured to house the chamber valve 500. The connection base 238 may include one or more sealing grooves 244 defined around an outer surface thereof for receiving one or more sealing members (e.g., sealing member 120*a*). The sealing groove 244 may define a first portion 240 and a second portion 244 in the connection base 238.

A valve cavity 227 is defined in the connection base 238 and is fluidly connected to the reservoir. With reference to FIG. 13C, the valve cavity 227 is configured to receive the chamber valve 500. The valve cavity 227 may include an upper lip 252 positioned below the floor 248 of the body 230 near the interface between the lower portion 234 of the body 230 and upper portion 240 of the base 238. The valve cavity 227 may also include a lower lip 254 positioned adjacent to the lower portion 242 of the base 238.

Figure 4C:
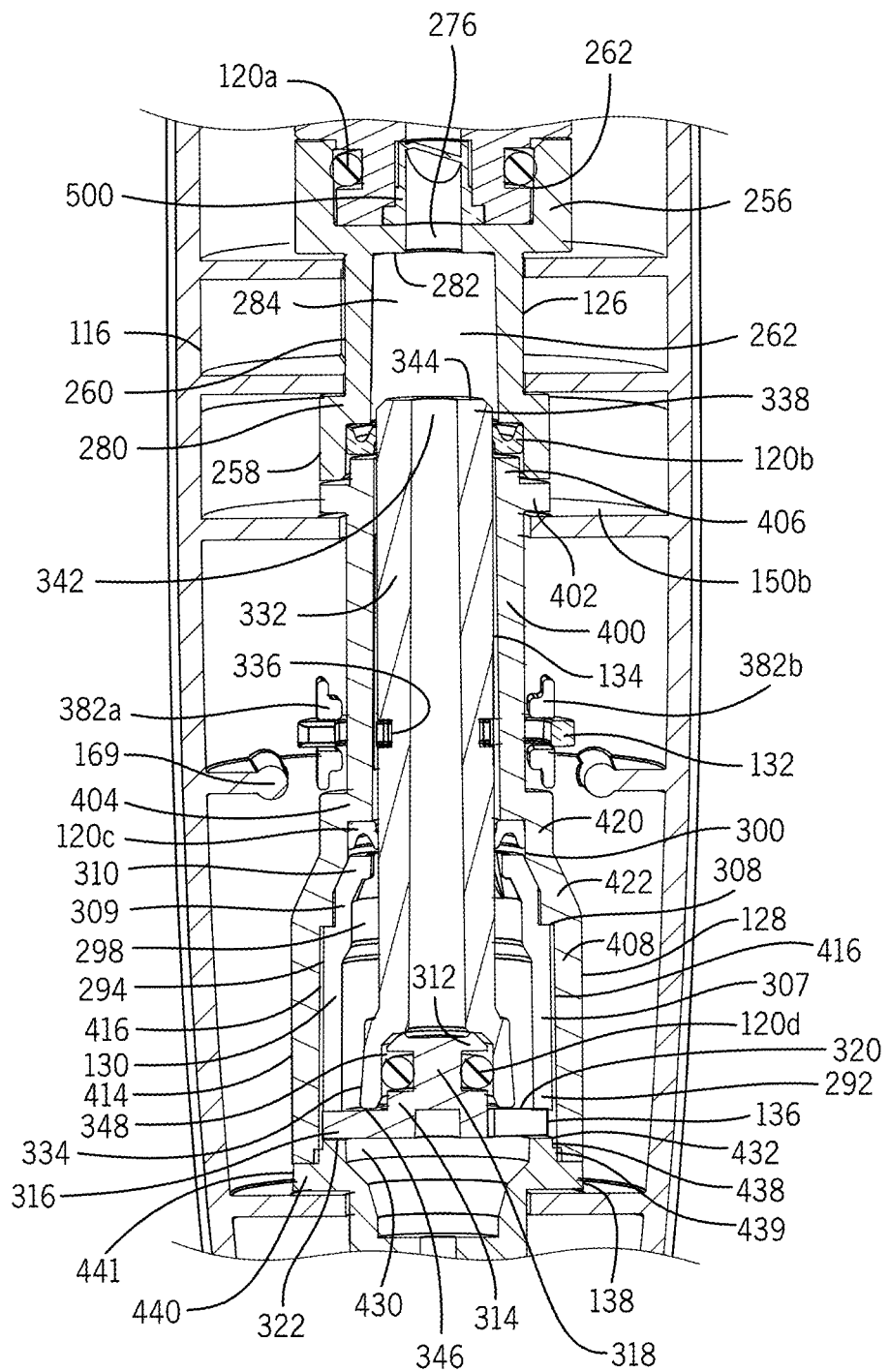
FIG. 4C is a partial cross section view of the handle of FIG. 4A.
Figure 5A:
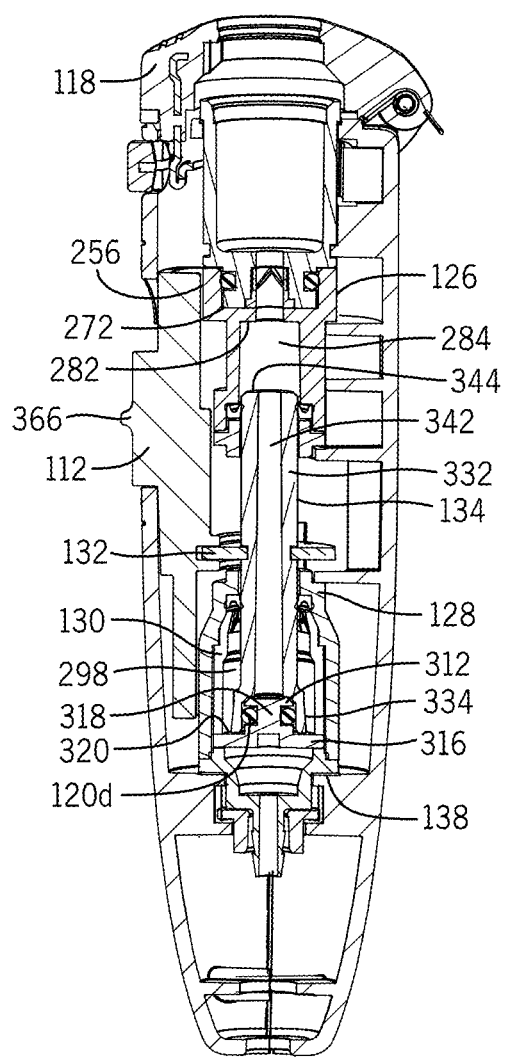
FIG. 5A is a cross section view of the handle of FIG. 1B along line 5-5 in FIG. 2A with a pause assembly activated.
Figure 12:
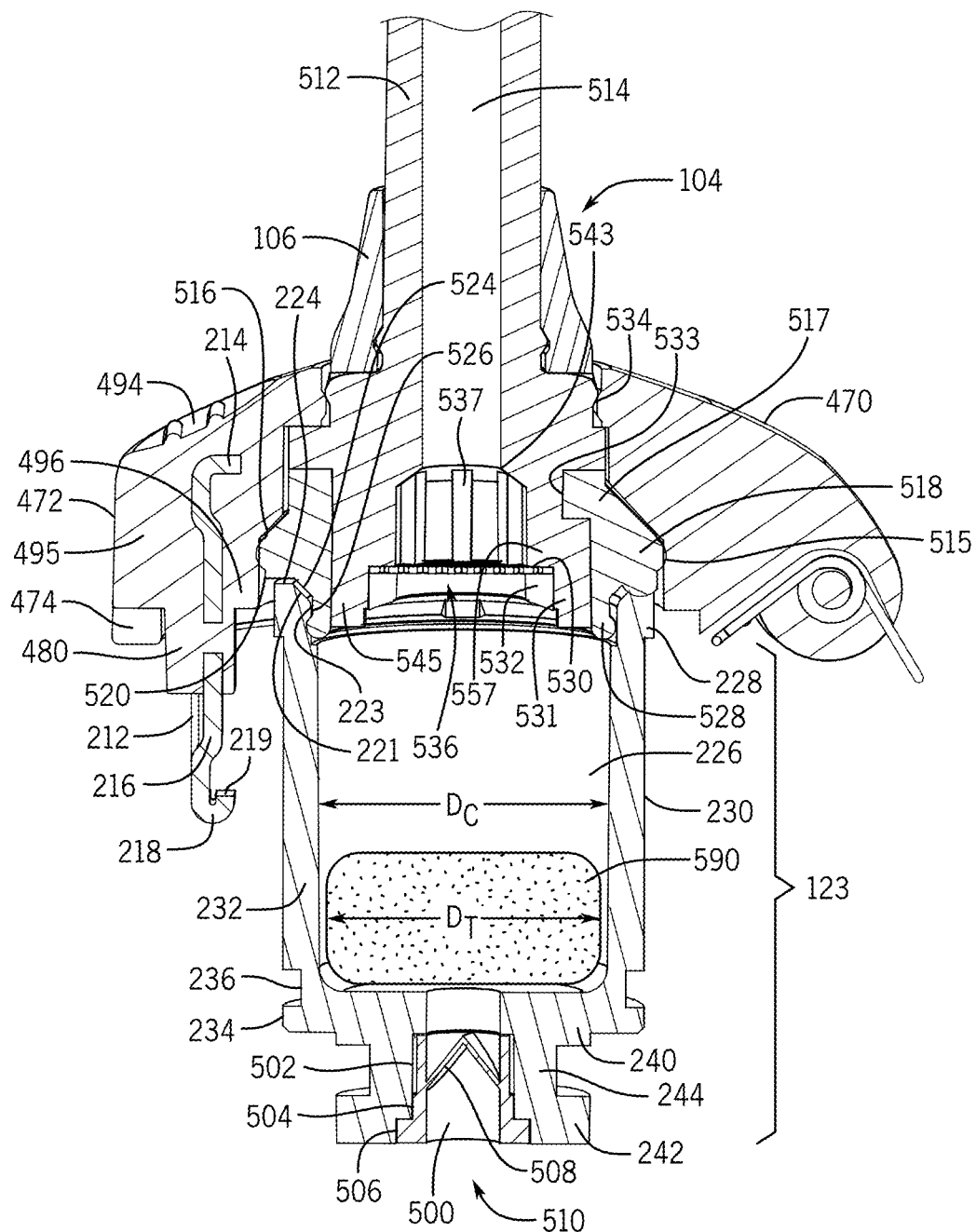
FIG. 12 is a partial enlarged cross section view of the lid and chamber body of the handle of FIG. 5A with a tip connected to the handle and an oral agent tablet positioned within the chamber.

The chamber valve 500 or check valve prevents backflow towards the reservoir 12. For example, the chamber valve 500 prevents fluid that has intermixed with the agent in the chamber 230 from traveling back into the reservoir or hose 108. In some embodiments, the chamber valve 500 may be a one-way fluid valve. In other embodiments, the valve 500 may be a filter or screen that prevents particles of a particular size from flowing back into the fluid path from the chamber 124. In one example the chamber valve 500 is a duckbill valve, but in other instances may be a reed valve or the like. With reference to FIGS. 4B and 12, in this embodiment, the chamber valve 500 is a duckbill valve and may include a rim 504 positioned below and adjacent to a body 502 and positioned above and adjacent to a plate 506. A cavity 510 may be defined continuously through each of the body 502, rim 504, and plate 506. One or more flaps 508 may be received in the cavity 510. When two flaps 508 are present, each may touch the other along at least a portion of its length to create a closed but unidirectional operable valve structure. For example, the flaps 508 may seal together upon application of a downward fluid force from the chamber, but may separate and open upon application of an upward fluid force from the reservoir.

Pause Assembly

Figure 14A:
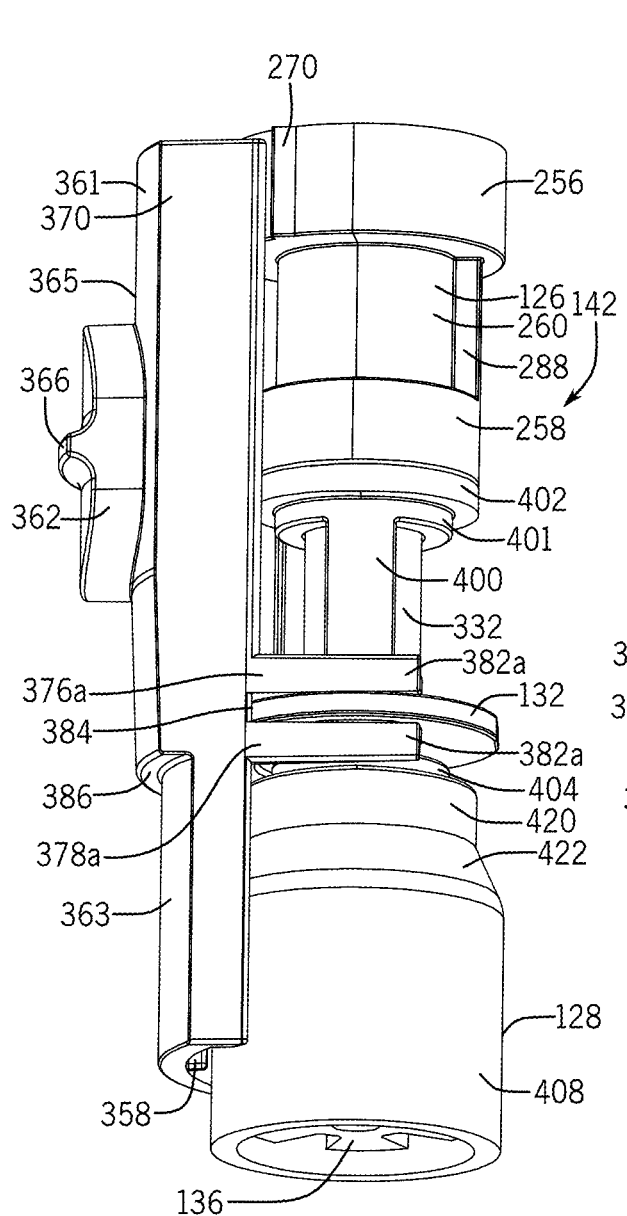
FIG. 14A is a right isometric view of a pause valve assembly of the handle of FIG. 1B.
Figure 14B:
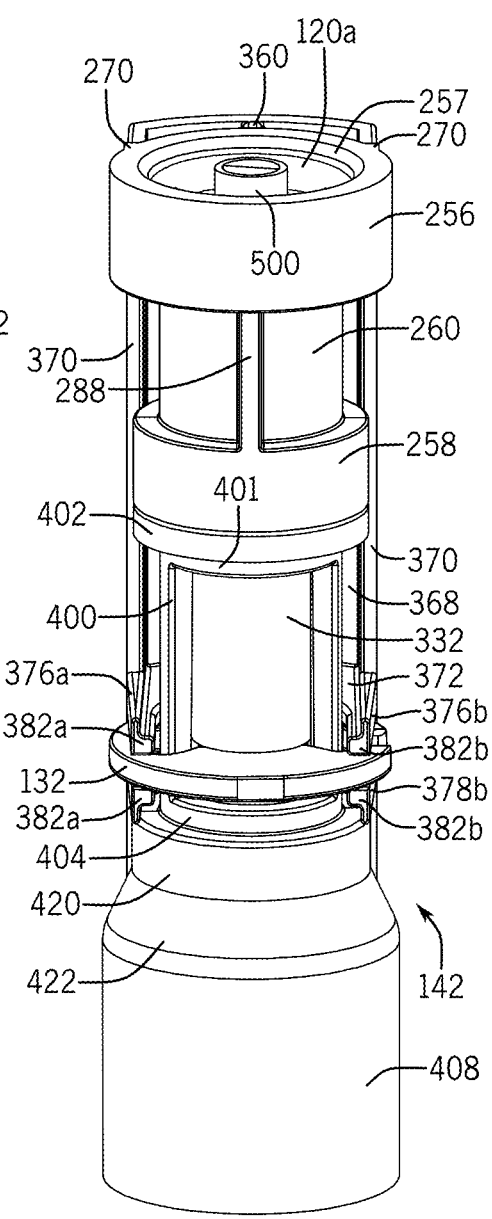
FIG. 14B is a rear isometric view of the pause valve assembly of FIG. 14A.
Figure 15:
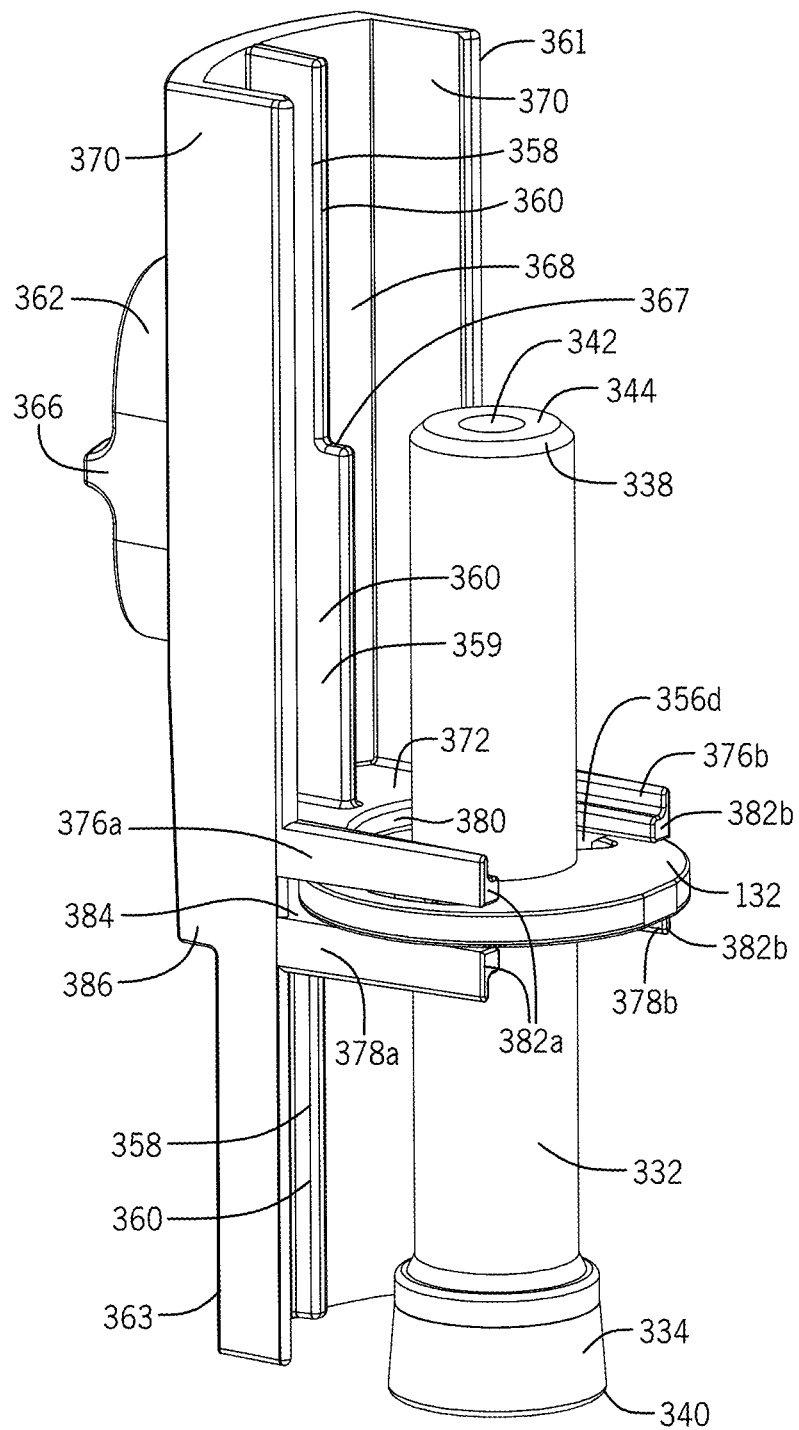
FIG. 15 is a right rear isometric view of select components of the pause valve assembly of FIG. 14A.

With reference to FIGS. 14A and 14B, the pause valve assembly 142 will now be discussed in more detail. The pause valve assembly 142 allows a user to interrupt fluid flow to the tip 104 without removing his or her hand from the handle 100 and without turning off power to the oral irrigator 10. The pause valve assembly 142 may include an upper valve body 126, a lower valve body 128, a shuttle valve 134, a shuttle retainer 130, a poppet assembly 136, a retaining ring 132, and a pause actuator 112. The various components of the pause valve assembly 142 will now be discussed in more detail.

With reference to FIGS. 14A, 14B, 16A, and 16B, the upper valve fitting or upper valve body 126 fluidly connects the chamber 124 and the lower valve body 128. The upper valve body 126 may include a head 256 and a base 258 connected by a neck 260. Each of the head 256, base 258, and neck 260 may be generally cylindrical and define a fluid passage 262 therethrough. The external diameter of the head 256 may be generally greater than the external diameter of the base 258, which in turn may be greater than the external diameter of the neck 260. The diameter of the head 256 is sufficiently wide to receive and secure the base 238 of the chamber 124.

The head 256 may include an interior beveled edge 57 angled inwards from a top surface 255 of the head 256 towards the fluid passage 262. The head 256 may include a bottom wall or floor 272 through which a valve flow aperture 276 is defined.

Figure 16C:
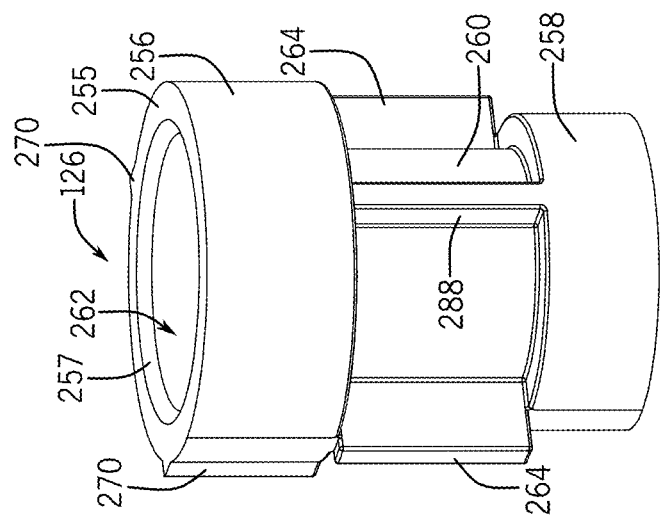
FIG. 16C is a front isometric view of an upper valve body according to another embodiment.
Figure 16B:
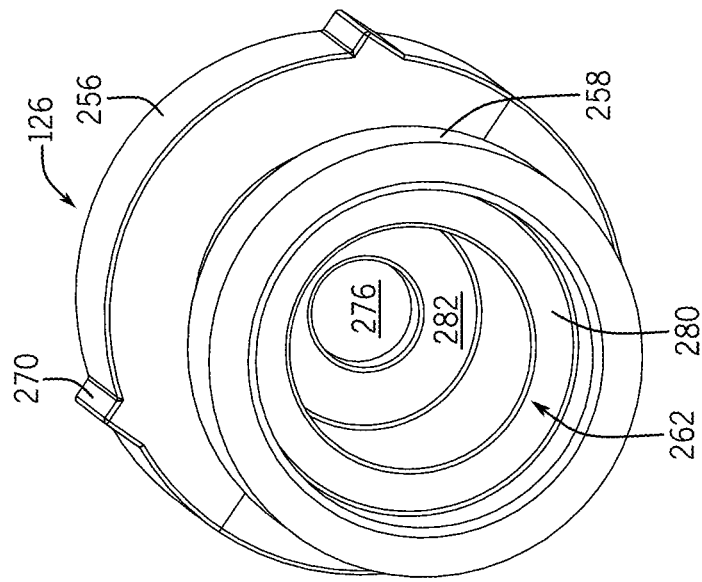
FIG. 16B is a bottom isometric view of the upper valve body of FIG. 16A.
Figure 16A:
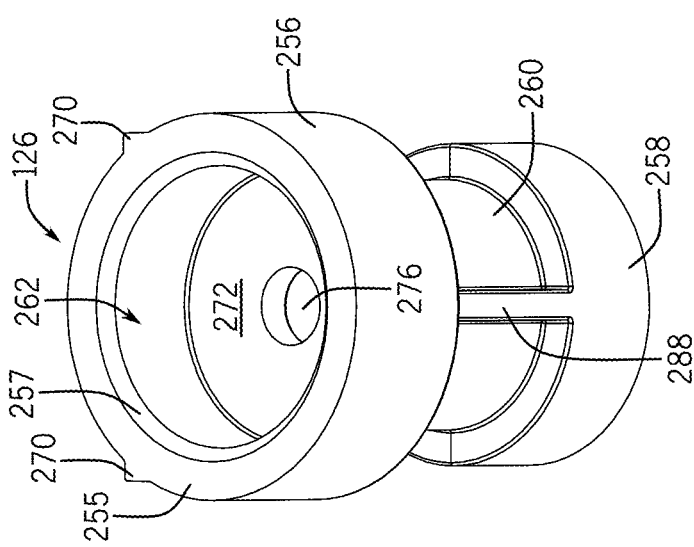
FIG. 16A is a front isometric view of an upper valve body of the pause valve assembly of FIG. 14A.
Figure 17B:
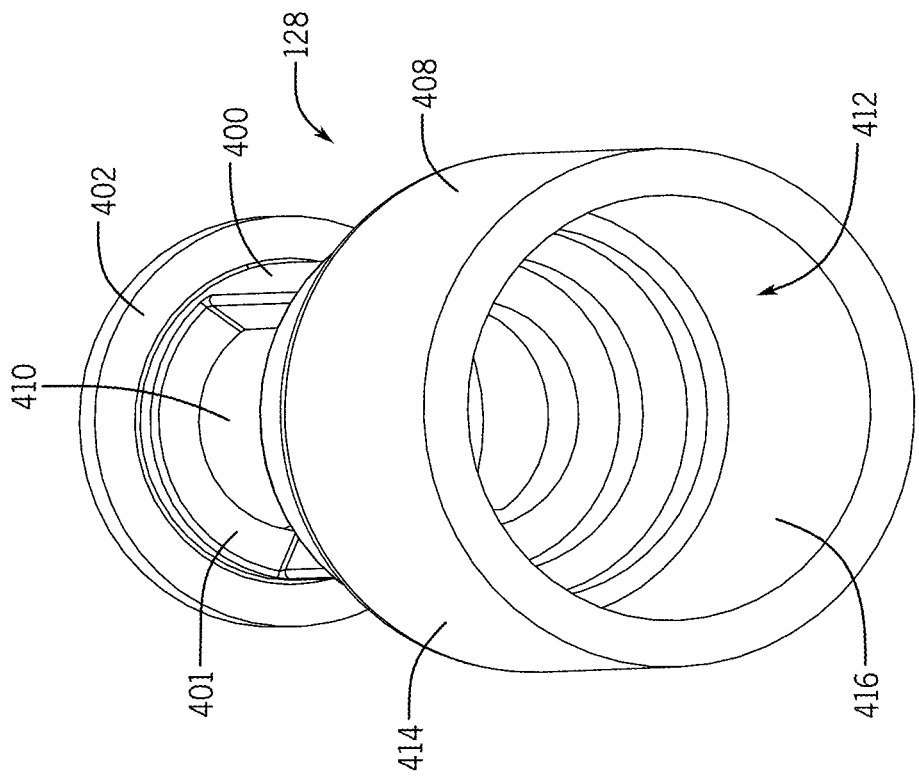
FIG. 17B is a front bottom isometric view of the lower valve body of FIG. 17A.
Figure 17A:
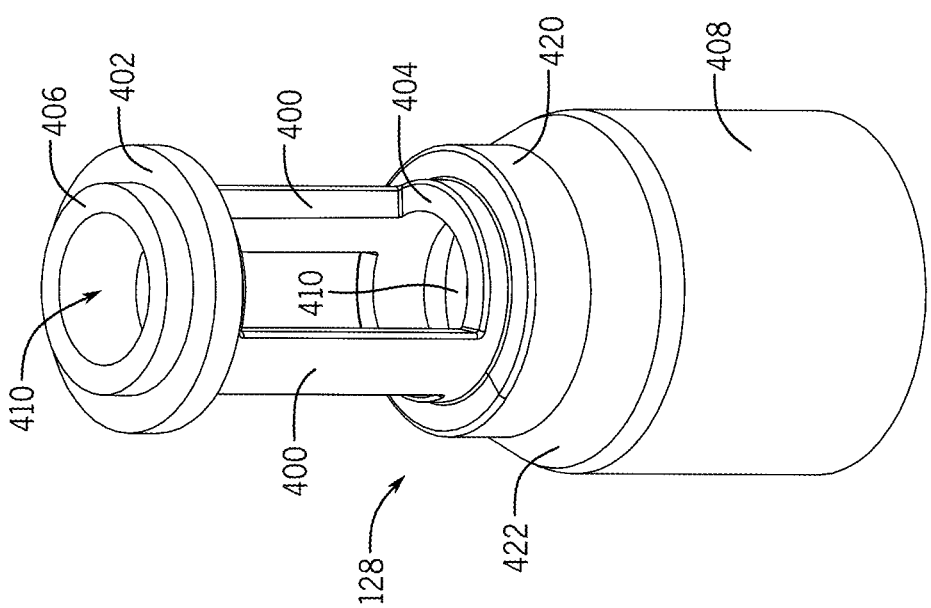
FIG. 17A is front top isometric view of a lower valve body of the pause valve assembly of FIG. 14A.

With reference to FIG. 16A, one or more alignment ribs 270 may extend longitudinally along from the outer surface the head 256. The alignment ribs 270 are positioned to engage and act as a track for the pause actuator 112 to move along. In one example, as shown in FIGS. 14A, 16A, and 16B, two alignment ribs 270 may be positioned approximately 90-180 degrees apart from each other on the head 256. The alignment ribs 270 may have the shape of shallow rectangular prisms with elongated bases as shown in FIG. 16B or may be other shapes.

A support rib 288 may extend from the neck 260 along the entire height of the neck 260 from the head 256 to the base 258. Additionally, in some embodiments as shown in FIG. 16C, two support wings 264 extend outwards and a long a portion of a length of the neck 260. The support wings 264 may act to retain the valve body 126 in a desired position within the handle 100.

As shown in FIG. 16B, the portion of the fluid passage 262 adjacent to the base 258 may include a lip 280 positioned below the floor 272 of the head 256 near the interface between the base 258 and neck 260. A sealing member 120b, such as U-cup, may be positioned under the lip 280.

With reference to FIGS. 14A, 14B, 17A, and 17B, a lower valve body 128 operably connects the upper valve body 126 and the valve base 138. The lower valve body 128 may include a plurality of support ribs 400, a shelf 404, a top end 402, a lip 406, an annular wall 420, and a skirt 408. In one embodiment, the support ribs 400 extend longitudinally between the shelf 404 and the top end 402 defining an open space therebetween. The lip 406 extends upwardly from the top end 402 and may encircle a valve body opening 410 defined through the top end 402. The annular wall 420 is connected to the bottom end of the shelf 404 and may include a larger diameter than the shelf 404. The skirt 408 extends downwards from the annular wall 420 and in some embodiments includes an upper portion 422 that is angled outward from the annular wall 420 such that the diameter of the skirt 408 may be larger than a diameter of the annular wall 420. The skirt 408 may include an outer skirt wall 414 and an inner skirt wall 416 and defines a skirt cavity 412.

With reference to FIGS. 14A, 14B, and 18, the shuttle retainer 130 receives fluid flowing past the poppet assembly 136 when the handle 100 is in pause mode. The shuttle retainer 130 may include a body 307 and a lip 309 that meet at a ledge 308. The shuttle retainer 130 may include an exterior wall 294 and a stepped interior wall 296 defining a cavity 298 that extends from an open first end 290 to an open second end 292. The open first end 290 may include a top surface 300 having a plurality of tabs 302 separated by notches around the perimeter 304 of the opening 306. The tabs 302 may define a broken circular edge with a circumference slightly larger than the circumference of the shuttle valve 134. The upper portion 310 of the lip may angle inwards towards the tabs 302 and opening 306.

With reference to FIGS. 14A, 14B, and 19, the shuttle valve 134 interrupts fluid flow through the handle 100 when pause mode is selected. The shuttle valve 134 may include a valve body 332 and a base 334. The body 332 may define a top surface 344 of the valve and the base 334 may define a bottom surface 346 and in some embodiments, the base 334 flares outwards from a bottom end of the valve body 332. The valve body 332 includes a connector groove 336 that may be positioned about midway along the length of the body 332. The connector groove 336 is configured to connect to a clamping feature that allows the shuttle valve 134 to move correspondingly with the pause actuator 112.

The shuttle valve 134 includes a flow lumen 342 defined through the valve body 332 and base 334. An open first end 338 of the shuttle valve 134 is fluidly connected to an open second end 340 by the flow lumen 342 and the base cavity 348.

Figure 20:
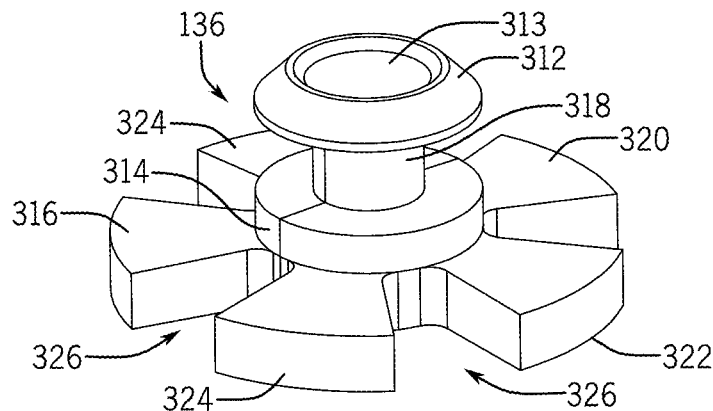
FIG. 20 is a front top isometric view of a poppet assembly of the pause valve assembly of FIG. 14A.

With reference to FIGS. 14A, 14B, and 20, a poppet assembly 136 is used to selectively disconnect fluid flow from the hose 108 to the chamber 124. The poppet assembly 136 may include a cap 312, including a recessed center portion 313, connected to a poppet support plate 316 by a poppet neck 318. An annular platform 314 may encircle the neck 318 above the poppet support plate 316. The diameter of the platform 314 may be approximately equal to the diameter of the cap 312 and less than the widest diameter of the poppet support plate 316. The cap 312 and annular platform 314 are generally sized and shaped to be received in the shuttle valve 134. The poppet support plate 316 includes a first surface 320, a second surface 322, and a plurality of spokes 324 extending outwardly from the platform 314. Two adjacent spokes 324 may be separated from each other to define a flow path 326 therebetween. A sealing member 120d may be seated around the poppet neck 318 between the cap 312 and platform 314.

Figure 21:
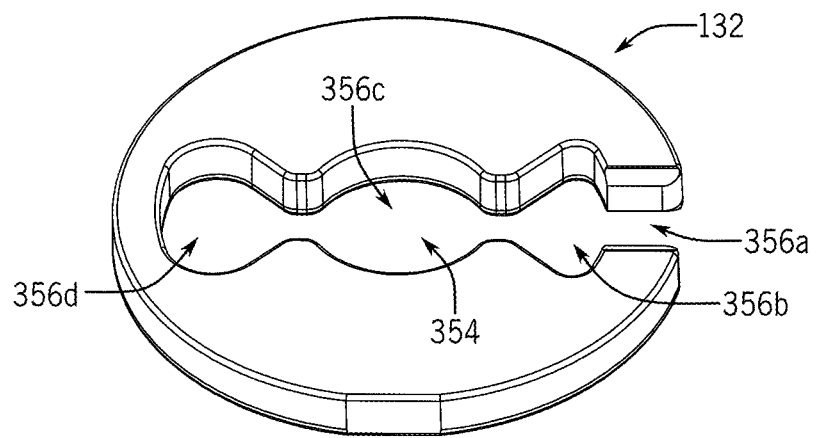
FIG. 21 is a front top isometric view of a retaining ring of the pause valve assembly of FIG. 14A.
Figure 22:
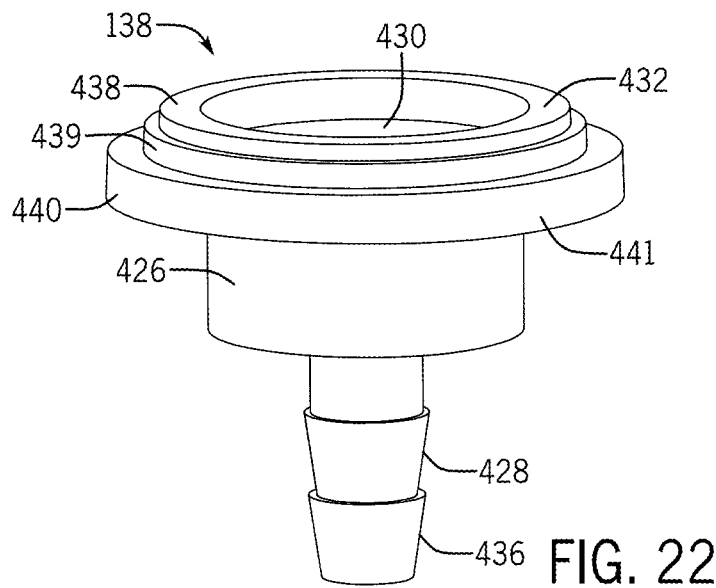
FIG. 22 is a front isometric view of a valve base of the handle of FIG. 1B.

With reference to FIGS. 14A, 14B, and 21, a retaining ring 132 operably connects the pause actuator 112 to the shuttle valve 134. The retaining ring 132 may be sized and shaped to engage components of the pause valve assembly 142. In one example, as shown in FIG. 21, the retaining ring 132 may be disc-shaped and include a keyhole cutout 354. The keyhole cutout 354 may include a first slot 356a, an arm aperture 356b, a center aperture 356c, and a hinge aperture 356d. The center aperture 356c may be sized to fit around the connector groove 336 of the shuttle valve 134, each of the arm aperture 356b and hinge aperture 356d may be sized to fit around a support rib 400 of the lower valve body 128. In some embodiments, the retaining ring 132 may be a snap ring and be sufficiently flexible to snap around the outer diameter of the shuttle valve 134.

With reference to FIGS. 2A, 2B, 3, 5A, 5B, 14A, and 15, the pause actuator 112 is moved by a user to place the handle in a pause or an irrigate mode. The pause actuator 112 may have a front face 365 defining an actuator lever 362 or button that a user can grip to move the pause actuator 112. The actuator lever 362 may be oval shaped and include a grip portion 366 extending outwards therefrom to allow a user to more easily grasp the lever 362.

In some embodiments, the front face 365 may be convexly curved to match the curvature of the handle housing, but in other embodiments may be differently configured. Additionally, the front face 365 may vary in depth as it transitions from an upper portion 361 to a lower portion 363. For example, as shown in FIG. 14A, an overhang 386 may be defined between the upper portion 361 and lower portion 363 of the front face 365 as the front face 365 transitions in depth.

The pause actuator 112 may also include sidewalls 370 that extend outwards from the rear of the front face 365 and extend along the longitudinal length of the actuator 112. A support rib 360 may be positioned between the two sidewalls 370 and extend the longitudinal length of the pause actuator 112. In some embodiments, the support rib 360 may include a stop 367 that has a longer width than the remaining portions of the support rib 360. The stop 367 may be used to limit the upward motion of the pause actuator 112 relative to the handle housing.

The pause actuator 112 may also include two pairs of clamping features 382a, 382b extending outwards from the sidewalls 370 and rear surface of the actuator 112. The clamping features 382a, 382b are configured to clamp around the retaining ring 132, such that movement of the pause actuator 112 will move the retaining ring 132 therewith. The clamping features 382a, 382b may include an upper shelf 372 and a lower shelf 374 for engaging the retaining ring 132 may extend parallel to each other from the rear face 368.

Each of the clamping features 382a, 382b may include a first upper prong 376a, 378a and a second upper prong 376b, 378b that extend parallel to one another. Each of the first prongs 376a, 378a may be laterally spaced from the second prongs 376b, 378b and are connected by a shelf wall 380 defined on an interior surface of the actuator face. Each upper prong 376a, 376b may be separated from its lower prong 378a, 378b by a retaining gap 384 between the upper and lower shelves 372, 374.

Swivel Assembly

With reference to FIGS. 3-5B and 22, the swivel assembly 143 will now be discussed in more detail. The swivel assembly 143 may help prevent translation of rotational movement of the handle 100 or the hose 108 relative to the other. The swivel assembly 143 may include a valve base 138 and a base collar 140. The valve base 138 is configured to be received within the stationary lower valve body 128. The valve base 138 may include a series of stacked concentric discs 438, 439, 440, a cylindrical body 426, and an elongated barbed tip 428. The top disc 438 may have the smallest diameter of the stack with the middle disc 439 having a diameter between the top disc 438 and the bottom disc 440. The thickness of each of the discs 438, 439, 440 may increase between each disc, with the top disc 438 having the smallest thickness, the middle disc 439 having a thickness between the two discs 438, 440, and the bottom disc 440 having the greatest thickness. The valve base 138 defines a flow cavity 430 from the barbed tip 428 through to the top surface 432 of the top disc 438. The barbed tip 428 may include one or more gripping components 436 that enhance the connection between the valve base 138 and the hose 108.

Figure 3:
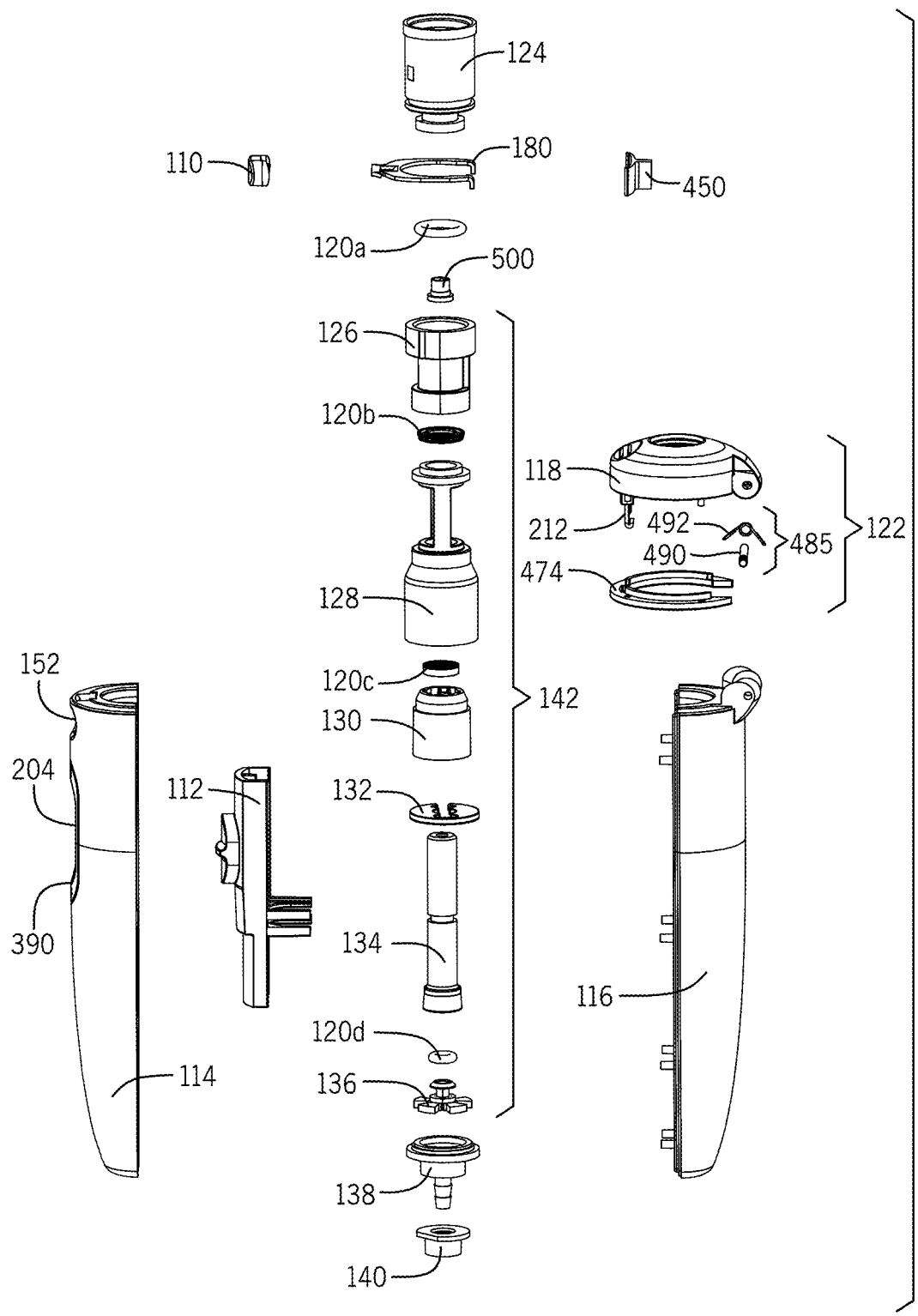
FIG. 3 is an exploded view of the handle of FIG. 1B.

The base collar 140 may define a barb aperture 442 configured to receive the barbed tip 428 of the valve base 138. In one example, as shown in FIGS. 3 and 4A, the base collar 140 may include a rim 444 and a body 446. The base collar 140 may be cylindrical in shape.

Assembly of the Oral Irrigator

An illustrative example of assembly of the handle will now be discussed. It should be noted that the below description is meant as exemplary only and the handle 100 may be assembled in any manner and in any order. In one embodiment, to assemble the pause valve assembly 142, the shuttle valve 134 is received in the upper and lower valve bodies 126, 128, the shuttle retainer 130 and poppet assembly 136 are both received in the lower valve body 128, and the pause actuator 112 is operably connected to the shuttle valve 134 by the retaining ring 132 such that selective movement of the actuator 112 also moves the shuttle valve 134 within the upper and lower valve bodies 126, 128.

The lip 406 of the lower valve body 128 may be received in the base 258 of the upper valve body 126 and may be positioned below and adjacent to the sealing member 120b positioned under the lip 280 of the fluid passage 262.

The shuttle retainer 130 may be received in the skirt cavity 412 of the lower valve body 128. The exterior wall 294 of the shuttle retainer 130 may be positioned adjacent to the inner skirt wall 416 of the lower valve body 128 such that the stepped profile of the exterior wall 294 follows the stepped profile of the inner skirt wall 416. The second end 292 of the shuttle retainer 130 may be positioned adjacent to the first surface 320 of the poppet support plate 316. The top surface 300 of the shuttle retainer 130 may be positioned below the sealing member 120c positioned under the shelf 404 of the lower valve body 128. The configuration of tabs 302 and notches in the top surface 300 may permit water to reach the sealing member 120c and press the sealing member 120c against the shelf 404, thereby creating a faster or stronger seal than in the absence of water.

The base 334 and a lower portion of the body 332 of the shuttle valve 134 may be received in the cavity 298 of the shuttle retainer 130. The first end 338 of the shuttle valve 134 may be received in the fluid passage 262 of the upper valve body 126. The support ribs 400 of the upper valve body 126 may flank a portion of the body 332 of the shuttle valve 134. A shuttle compartment 284 may be formed in the space between the bottom surface 282 of the floor 272 of the head 256 of the upper valve body 126 and the top surface 344 of the body 332 of the shuttle valve 134 when the handle 100 is in pause mode. The retaining ring 132 may be flexed at the hinge aperture 356d to widen the slot 356a and seat the center aperture 356c of the retaining ring 132 within the connector groove 336 of the shuttle valve 134.

The cap 312, and the sealing member 120d positioned around the poppet neck 318, of the poppet assembly 136 may be received in the base cavity 348 of the shuttle valve 134. The first surface 320 of the poppet support plate 316 may be positioned below and adjacent to the bottom surface 346 of the base 334 of the shuttle valve 134 and below and adjacent to the second end 292 of the shuttle retainer 130.

The pause actuator 112 may extend from approximately the head 256 of the upper valve body 126 to the skirt 408 of the valve lower housing. At the rear of the upper portion 361 of the pause actuator 112, each side wall 370 may be positioned adjacent an alignment rib 270 of the head 256 of the upper valve body 126. Also at the upper portion 361, the end portion 358 of the center wall 360 may be positioned adjacent to the head 256 and base 258 of the upper valve body 126, at least when the pause mode is selected. The middle portion 359 of the center wall 360 may be positioned adjacent to the base 258 of the upper valve body 126 and the upper plate 402 of the lower valve body 128. The middle portion 359 may also face the body 332 of the shuttle valve 134. The end portion 358, near the lower portion 363 of the pause actuator 112, of the center wall 360 may be positioned adjacent to the skirt of the lower valve body 128. The retaining ring 132 may be captured in the gap 384 formed between the upper prongs 376a, 376b, and lower prongs 378a, 378b. One pair of upper and lower prongs 376b, 378b may traverse some or all of the slot 356a of the keyhole 354 of the retaining ring 132. Another pair of upper and lower prongs 376a, 378a may traverse some or all of the hinge aperture 356d.

When the housing 102 is assembled, the actuator lever 362 of the pause actuator 112 may be positioned within the pause actuator aperture 204 in the first shell 114 and the front face 365 of the pause actuator 112 may be positioned against an interior wall 174a of the first shell 114 opposite at least a portion of the pause actuator frame 390. The upper and lower portions 392, 394 of the aperture 204 extend beyond the length of the actuator lever 362 such that the aperture 204 is longer than the actuator lever 362 and shorter than the remainder of the pause actuator 112. In this configuration, the pause actuator 112 is both retained within the aperture 204 and can slide longitudinally within the aperture 204 as the actuator lever 362 and pause actuator 112 travel on either side of the aperture 204 and frame 390. By placing the pause actuator 112 on the handle 100, the user may more easily change settings or pause the fluid flow while using an oral irrigator that is fluidly connected to the handle 100.

When the housing 102 is assembled, various portions of the pause valve assembly 142 may be supported or captured by ledges 150a, 150b or vertical support walls 148a, 148b. For example, a ledge 150b may be positioned beneath the head 256 and adjacent to the neck 260 of the upper valve body 126. Another ledge 150b may be positioned adjacent to the neck 260 and above the base 258 of the upper valve body 126. As another example, the upper plate 402 of the lower valve body 128 may rest on a ledge 150b. The retaining wall 288 of the lower valve body 128 may extend perpendicularly to the ledges 150b of the second shell 116 and be positioned in a slot 151 in one or more ledges 150b.

To assemble the swivel assembly 143, the barbed tip 428 of the valve base 138 is received in the barb aperture 442 of the base collar 140. Ledges 150a, 150b of the shells 114, 116 may be positioned beneath the bottom disc 440 and adjacent to the body 426 of the valve base 138. The rim 444 of the base collar 140 may rest on ledges 150a, 150b.

To join the cover assembly and the chamber assembly, the chamber 124 is positioned between the inner walls 188 of the arms 186 of the latch 180 and between the neck 196 of the latch 180 and the terminal ends 462 of the latch spring 450. The chamber 124 may not completely fill the space between the arms 186 such that lateral movement of the latch 180 towards or away from the latch button 110 is permitted.

The agent assembly 123 is assembled by inserting the chamber valve 500 in the valve cavity 227 of the base 238 of the chamber 124.

When the housing 102 is assembled, the rim 228 of the chamber 124 may sit on a step 205a on the upper surface 207 of the first and second shells 114, 116 such that the rim 228 extends above the plane of the upper surface 207. The neck 236 of the body 230 of the chamber 124 may receive a ledge 150a, 150b of the first and second shells 114, 116.

To connect the pause valve assembly 142 to the swivel assembly 143, the top surface 432 of the top disc 438 of the valve base 138 may be positioned below and adjacent to the second surface 322 of the poppet support plate 316 of the poppet assembly 136. The middle disc 439 may be positioned adjacent to the inner skirt wall 416 of the lower valve body 128. The outer diameter of the bottom disc 440 may be approximately the same as the outer diameter of the skirt 408 of the lower valve body 128 such that when the bottom disc 440 is positioned under the skirt 408, the outer skirt wall 414 may be flush with an outer surface 441 of the bottom disc 440. The barbed tip 428 of the valve base 138 may be received in the barb aperture 442 of the base collar 140.

An end of the hose 108 may fit over the barbed tip 428. The hose 108 may exit the cavity 172 of the assembled housing 102 at the aperture 146.

To connect the agent assembly 123 and pause valve assembly 142, the base 238 of the chamber 124, and the sealing member 120a adjacent the neck 244 of the base 238, may be received in the upper valve body 126 and the fluid passages aligned. For example, the top surface 255 of the head 256 of the upper valve body 126 may be positioned below and adjacent to the lower portion 234 of the body 230 of the chamber 124. The chamber valve 500 may be positioned such that the cavity 510 of the chamber valve 500 is below the flow aperture 250 in the floor 248 of the chamber 124 and over the flow aperture 276 in the floor 272 of the fluid passage 262 of the upper valve body 126.

The cover assembly 122 may be assembled by connecting the latch button 110 to the latch spring 450 via the latch 180. The coupling head 175 and tab clips 176 of the latch 180 are inserted into the plate slot 164 of the latch button 110. The tab clips 176 may be angled slightly away from the plane of the coupling head 175. As the tab clips 176 are inserted into the plate slot 164 of the latch button 110, the clips 176 may flex to align with the plane of the head 175. The clips 176 may then bend towards their original position, biasing them against the inside of the slot 164, thereby securing the latch button 110 to the latch plate 118. The engagement surface 184 of each foot 182 of the latch 180 may abut the corresponding engagement nub 464 of each terminal end 462 of the latch spring 450. The spine 452 of the latch spring 450 may be biased against the interior of the second shell 116.

Further assembly of the cover assembly 122 includes connecting the lid 118 to each of the trim ring 474, latch catch 212, and housing 102. The trim ring 474 is secured to the lid 118, such as against the outer rim 495 of the lid 118, by fitting the pins 478 of the lid 118 through corresponding holes 479 in the trim ring 474. The catch body 216 and anchoring shelf 214 of the latch catch 212 may be overmolded, insert molded, or otherwise embedded in the slot 484 of the lid 118 such that a portion of the lid 118 extends into the well 220 of the latch catch 212.

Before connecting the lid 118 to the housing 102, the pause valve assembly 142, swivel assembly 143, and agent assembly 123 are assembled and the first and second shells 112, 114 are secured to each other to enclose the pause valve, swivel, and chamber assemblies 142, 143, 123.

The lid 118 is connected to the housing 102 via the hinge assembly 485. For example, a knuckle 206 of the second shell 116 is positioned on either side of the hinge body 486 of the lid 118. The pin 490 is inserted through the pin aperture 208 of the knuckles 206 and through the channel 488 of the hinge body 486. The lid spring 492 may be seated in the recess 491 of the hinge body 486 and bridge 493 and may encircle the pin 490 at approximately the longitudinal center of the pin 490.

Once assembled, the lid 118 of the handle of FIGS. 1A-24B may be opened and closed to allow a user to insert and/or remove a dental agent. For example, a user may open the lid 118 by first pressing on the outer surface 158 of the body 156 of the latch button 110. As the latch button 110 is compressed, the button 110 exerts a force against the latch 180 via the terminus or engaging ends 162 of each arm 160 of the latch button 156. In particular, the arms 160 press against the top wall 192 of the shoulder 190 of the latch 180, causing the neck 196 and affixed clasp tab 200 of the latch 180 to move laterally inwards towards a center of the handle. As the latch button 110 is compressed, the rigid latch 190 moves, exerting a force against the engagement nubs 464 of the latch spring 450. This causes the latch arms 462 to flex, since the latch spring is secured in position relative to the housing. The flexibility of the arms 462 allows the latch 180 to be displaced relative to the latch catch 212. In particular, the as the latch 180 moves, the engaging face 202 of the tab 200 of the latch 180 disengages from the end 219 of the hook 218 of the latch catch 212, i.e., the engaging face 202 of the tab 200 moves horizontally to unseat the latch catch 212. Once the latch 180 unblocks the latch catch 212, the force of the lid spring 492 against the step 205e causes the lid 118, and the catch 212, to pivot, and move away from the handle. As this occurs, the catch 212 and hook 218, passes through the catch aperture 199 of the latch 180 and through the catch aperture 154 of the first shell 114, allowing the lid 118 to pivot on the pin 490. In this manner, a user is thus able to open the lid 118 with one hand as all that is needed to open the lid is to compress the button 110 with a finger.

When the horizontal force by the user on the button 110 is removed, the latch spring 450 may return to its original shape and/or position. In particular, the latch spring 452 arms will spring back or return to their original position, exerting a return force on the latch 180, causing the latch 180 to move horizontally in the opposite direction, returning to its first position.

To close the lid 118, the user exerts a downward force on the top of the lid 118, which overcomes the force of the lid spring 492, and the lid 118 pivots about the pin 490 towards the handle. As this occurs, the latch catch 212 passes through catch apertures 154, 199 of the housing and latch 180, respectively. The sloped surface of the tab 200 allows the hook to easily slide through the catch aperture on the latch 180, until the catch is positioned in the latching position to engage with the bottom surface of the latch. Further, as the hook moves through the catch aperture, the hook 218 portion engages tab 200 of the latch 180, causing the latch 180 to move laterally, allowing the hook 218 to extend through the opening 199. As soon as the hook 218 is through the catch aperture 199, the tab 200 is no longer forced towards the spring 452, and the latch 180 is forced by the spring 452 back towards its original position, engaging the end face of the hook 218 against the bottom surface of the latch 180.

Components and Assembly of the Tip

In some embodiments, the tip may be operably and releasably coupled to the handle 100. In some instances, the tip or tip assembly may include features of the agent assembly, such as one or more filters, which allow the filters to be more easily replaced. FIGS. 7A and 7B illustrate various views of a tip assembly 104 for use with the handle. With reference to FIGS. 7A, 7B, and 12, the tip assembly 104 includes a tip collar 106, a tip body 512, a tip seal cap 515, and a filter 530, each discussed below. It should be noted that the configuration of the tip is meant to be aesthetically pleasing, as well as functional. Since the various portions of the tip may be exposed to a user before and after coupling to the handle, the features may be designed in a manner to enhance the aesthetic appearance, as well as the functionality.

The tip ring 106 or collar may encircle or surround a portion of the tip body 512 at a position immediately above and adjacent to the tip collar 534. The tip ring or collar 106 may be formed of various colors to identify different tips for different users. Additionally, the tip collar 106 may include an alignment icon 539, such as a colored, printed, embossed, engraved, indented, or otherwise formed, feature on a front surface thereof. The alignment icon 539 in one embodiment is a printed dot indicating a front center portion of the tip to allow a user to more easily align the tip in the handle as discussed below. In some embodiments, the lid 118 may include a corresponding alignment icon 471 that a user can reference when inserting the tip.

The tip body 512 forms a jet tip for the handle and terminates with a tip outlet 105 formed a terminal end thereof through which fluid can be expelled. A channel 514 for the passage of fluid may be defined through the length of the tip body 512. The opposite end of the tip body 512 defines a filter housing 534 and engages with the tip seal cap 515 and receives the filter 530. The filter housing 534 may be defined at a bottom end of the tip body 512 and extends radially outwards and downwards from the bottom of the tip body 512. For example, the filter housing 534 may be defined as an expanded cylindrical end for the tip.

The filter housing 534 may include various features for engaging the tip seal cap 515, as well as the filter 530, as well as define an internal cavity 536 for receiving the filter assembly. In some embodiments, the filter housing 534 may include one more connection grooves 541, which may be defined on an exterior surface as annular grooves, to receive portions of the seal cap 515. The filter housing 534 may have stepped perimeter, which may help the tip 104 engage and/or form a seal against the portion of the tip cavity 211 adjacent the crown 470 of the lid 118 when the tip 104 is inserted in the handle 100. The bottom end of the tip or the filter housing 534 may also include an alignment tab 538. The alignment tab 538 may be extend outwards from a front sidewall of the filter housing 534. The size and shape of the alignment tab 538 may be complimentary to the tip alignment notch 497 defined in the ledge 498 of the lid body 472 of the lid 118.

Additionally, the filter housing 534 defines a filtering chamber 536 in a bottom end thereof. The filtering chamber 536 may be defined as a stepped chamber having an internal shelf 557 defined above a bottom end 531 of the tip body 512. A top end of the chamber 536 includes tapered walls 543 that direct the flow into the tip fluid passage 514. Sidewalls of the chamber 536 include vertical ribs 537 that extend parallel to the longitudinal axis of the filter housing 534 to provide additional strength, as well as define brackets for securing the filter 530 in position, without significantly decreasing the diameter of the fluid passage of the chamber 536. The bottom portion of the filtering chamber 536 also include a screen support 532 that may be defined as an annular rim that extends into the filtering chamber 536. The bottom wall 531 defining the opening of the filtering chamber 536 may include one or more nubs 545 spaced around the chamber opening.

With reference to FIGS. 7A-7C, the tip seal cap 515 is configured to seal the bottom end of the tip when the tip 104 is positioned in the handle and is configured to engage with a portion of the outer surface of the filter housing 534. The tip seal cap 515 may include a skirt 516, an exterior wall 522, and an annular lip 528. This skirt 516 is spaced apart from a top end of the tip seal cap 515 and defines an angled surface 517 as it extends downwards and radially away from a central axis of the seal cap 515. The skirt 516 may include a rim 518 is formed as annular bead extending around the outer perimeter, which in some embodiments, may act as a compressible seal to ensure a tight seal with the handle. In other embodiments, the rim 518 may be formed by an O-ring formed integrally with or secured to the tip seal cap 515.

A portion of the front face of the skirt 516 may transition to form an alignment tab 540. The tab 540 assists a user in visually aligning the tip 104 in the tip cavity 211. Additionally or alternatively, the tab 540 may provide reinforcement to the seal cap 515 against the rim 228 of the chamber 124 where the base 515 first contacts the rim 228 as the lid 118 is being closed. In some examples, the tab 540 is formed to be aligned with the alignment tab 538 of the filter housing 534 when secured together. In some examples, the tab 540 is semicircular in shape but may be any shape.

With continued reference to FIG. 7C, from the bottom of the skirt 516, the seal cap 515 transitions to define an exterior wall 522 may include an angled portion 524 that transitions to vertical wall 526. The seal cap 515 terminates with an end bead 528 that extends radially outwards from the vertical wall 526 and may act as an O-ring or other compressible feature to ensure the tip seal 515 is sealed against the various surfaces within the handle when the tip 104 is inserted therein.

The seal cap 515 may have a stepped perimeter for engaging the lid 118 and chamber 124. The perimeter may be complementary to portions of the lid 118 and chamber 124. In one example, as shown in FIG. 12, the perimeter may increase along the angled portion 517 of the hip 516 to the annular rim 518, which may be the widest portion of the base 515. The perimeter of the base 515 may step inwards from the annular rim 518 to the exterior wall 522 such that a portion of a bottom surface 520 of the hip is exposed. The diameter of the annular lip 528 may be greater than the diameter of the vertical portion 526 of the exterior wall 522 but less than the greatest diameter of the sloped portion 524 of the vertical wall 522.

To assemble the tip 104, the tip collar 106 is positioned over the tip body 512 and rests on a top surface 549 of the filter housing 534. In some embodiments, a body nub 551 seats within a corresponding recess 553 in the tip collar 506 to secure the collar 106 in position and prevent rotation relative to the tip body 512. The alignment icon 539 is oriented to be facing forward in the same direction as the outlet 105 of the tip body 512. With reference to FIGS. 7B and 7C, the filter assembly 530, 532 is positioned within the filter housing 534. For example, the filter screen 530 is received within the filter chamber 536 and pressed against the bottom surface of the ledge 557 with the filter housing 534. The ledge 557 operates to prevent the filter screen 530 from being dislodged or otherwise moving in position when fluid flows from the filter chamber 536 to the fluid pathway 514 within the tip body 512. The screen support 532, which may be inserted simultaneously with or after the filter 530, is then positioned beneath the filter 530 and against an interior wall of the filter housing 534. The nubs 545 may prevent downward movement of the filter assembly during use.

The tip seal cap 515 is received around the outer surface of the filter housing 534. For example, the tab 540 may be aligned with the tap 538 of the filter housing 534 and the tip seal cap 515 press fit onto the filter housing. The top end of the seal cap 515 fits into sealing groove 537 of the filter housing 534 to securing the cap 515 in position. When positioned on the tip, the seal cap 515 extends past the bottom end 531 with the lower bead 528 forming the terminal end of the tip assembly.

Inserting and Removing a Tip

A user may insert a tip 104 into, and remove a tip 104 from, the handle 100 of FIGS. 1A-24B. In many embodiments, the tip 104 is secured to the lid 118 of the handle 104 and pivots away from and towards the handle 100 with the lid 118. To insert a tip, the user may open the lid 118 and the tip 104, starting with the tip outlet 105, may be passed through the tip cavity 211 and the tip-receiving aperture 210 of the lid 118 until the tip collar 106 is positioned above and adjacent to the crown 470 of the lid 118. The filter housing 534 of the tip 104 is seated against the inside of the tip cavity 211 adjacent the crown 470 of the lid 118. The alignment tab 538 on the filter housing 534 is positioned within the tip alignment notch 497 in the ledge 498 of the body 472 of the lid 118, securing the tip 104 within the lid 118, as well as ensuring that the tip 104 is properly aligned relative to the lid 118.

Further, the seal cap 515 is pressed against the internal surface ledge 498 of the lid 118, with the angled surface 517 of the skirt 516 having a slope corresponding to and complementary to the slope of the internal wall of the lid 118, e.g., the surface ledge 498. The outer bead 518 engages and is compressed by the ledge 496 to ensure a sealed connection between the tip 104 and the lid 118. The tab 540 of the seal cap 515 is also positioned within the notch 497, but below the tab 538 of the filter housing 534.

The secured engagement of the seal cap 515 and the filter housing 534, ensures that the tip 104 will remain secured to the lid 118 even under water pressure with fluid flowing through the chamber 536 and out the tip outlet 105. Further, as the lid 118 pivots relative to the handle, the tip 104 will move therewith, to allow a user to more easily insert the oral hygiene tablet, without having to remove the tip 104.

When the lid 118 is closed and the latch catch 212 of the lid 118 is captured by the clasp tab 200 of the latch 180, as described above, the tip 104 is maintained in position against the housing 102 along with the lid 118. Additionally, when the lid 118 is closed, the seal cap 515 of the tip 104 is brought over and is partially seated into the opening to the agent chamber 226 of the chamber 124. The annular lip 528 of the tip seal cap 515 is seated against the rim 228 to form a fluid-tight compression seal. In some embodiments, the annular lip 528 and rim 228 fit irregularly together, which may provide a fluid-tight seal while preventing the premature degradation of the interface between the tip 104 and the chamber 124.

The bottom surface 520 of the skirt 516 of the base 515 of the tip 104 is positioned above and adjacent to the upper surface 224 of the rim 228 of the chamber 124. The interface between the bottom surface 520 of the skirt 516 and the upper surface 224 of the rim 228 may form a seal secondary to the interface between the annular lip 528 and the rim 228.

The sloped portion 524 of the exterior wall 522 of the seal cap 515 is positioned adjacent to the sloped portion 221 of the interior wall 222 of the rim 228. The compressibility of the seal cap 515 and bead 528, may define a sealed engagement with the chamber, while allowing the seal cap to move relative thereto when the lid 118 is opened, moving the tip 104 therewith. The vertical portion 526 of the exterior wall 522 may positioned adjacent to, the vertical portion 223 of the interior wall 222 of the rim 228.

To remove the tip 104 from the handle 100, the latch button 110 is depressed, releasing the lid latch as described above. As the lid 118 pivots away from the handle, the annular lip 528 of the tip seal cap 515 disengages from the rim 228 of the chamber 124, aided by the force of the spring 492 in the recess 491 of the hinge body 486 of the lid 118. The, the user can pull the tip 104 out through the tip cavity 210 of the lid 118, such as by grasping the tip body 512 or tip collar 106.

Using the Handle

A user may use the handle 100 of FIGS. 1B-24B and the oral irrigator 10 to which it is fluidly connected (see FIG. 1A) for oral irrigation and/or cleaning of the teeth, gums, and tongue. For example, once a tip 104 is connected to the handle 100 and with the lid 118 in the open position (see FIGS. 24A and 24B), the agent chamber 226 of the chamber body 230 is exposed. A user can then place the dental agent for use in the chamber 226. One example of a suitable dental agent is described in U.S. Provisional Patent Application No. 62/453,949, which is incorporated herein by reference in its entirety.

As shown in FIG. 12, once an oral agent, which may be tablet 590 is received within the chamber 226, the tablet 590 spans across a majority of the diameter of the chamber 226. In some embodiments, the chamber is sized such that the longest dimension of the tablet 590 is close to the length of the chamber diameter. This helps ensure that the water jet, entering through chamber valve 500 into the chamber 226, will impinge on its round or longest dimensional face, rather than on its side. For example, in some embodiments, the tablet chamber diameter is between 0.5 to 1.0 inches, in some embodiments 0.470 inches and the tablet diameter may range from 0.4 to 0.90 inches, and in some embodiments be 0.440 inches. In these embodiments, a ratio of approximately 1:1 chamber diameter to tablet diameter was found to allow the tablet to be impinged on its largest face, ensuring even ablating, as well as ensure that the cross-section is not overly larger that the fluid pressure within the chamber 226 overstresses the latch mechanism for the lid 118. This is because in some instances the tablet 590 may be formed by particles or powder that is compressed in the axial dimension and disintegrate more predictably when the water jet impinges the tablet 590 axially, such as perpendicularly as it enters the chamber 226 through the valve 508.

With continued reference to FIGS. 24A and 24B, the upstream screen 530 may be connected to the lid 118 and pivot therewith, uncovering the chamber 226, which allows a user to more easily access the agent chamber 226. However, in other embodiments, the screen 530 may remain stationary and a user may need to maneuver the agent around the screen 530 or otherwise remove the screen 530 before placing the agent into the chamber 226.

In the embodiment shown in FIGS. 24A and 24B, the opened lid 118 remains connected to the housing 102 via the hinge assembly 485. This helps to prevent the user from misplacing the lid 118 when inserting the oral hygiene agent, as well as enables a user to keep one hand free to insert the agent.

Once the dental agent is inserted, or in instances when a user may wish to omit the dental agent, the user closes the lid 118 by pivoting the lid 118 about the pin 490 to flip the lid 118 downwards towards the upper surface 207 of the first and second shells 114, 116. Pressing on the grip portion 494 on the upper surface 471 of the crown 470 of the lid 118 overcomes the bias of the spring 492 to be able to pass the hook 218 of the latch catch 212 through the catch aperture 154 of the first shell and through the clasp aperture 199 of the latch 180. As the catch is inserted, the catch tip engages the latch 180 to force it to compress against the latch spring 450, which flexes to allow the latch 180 to move laterally to allow the catch to be received into the clasp aperture 199. Then, the end 202 of the clasp tab 200 of the latch 180 captures the end 219 of the hook 218 of the latch catch 212, thereby securing the lid 118 to the housing 102.

When the lid 118 is in the closed position (see FIG. 1B), the bottom surface 476 of the trim ring 474 may contact the upper surface 207, such as the step 205c, of the first and second shells 114, 116.

The, the user can turn on the irrigator. In particular, the handle 100 is fluidly connected to a fluid source, such as a reservoir 12 of an oral irrigator 10, and power is supplied to the oral irrigator 10, the handle 100 is ready to use. When activated, the pump 16 pulls fluid from the reservoir 12 through the hose 108 into the flow cavity 430 in the valve base 138 and into the cavity 298 of the shuttle retainer 130. In other embodiments, such as when the reservoir 12 and the pump 16 are connected to the handle (e.g., a handheld oral irrigator), an internal fluid passageway instead of a hose 108 may be used.

During irrigate mode (see FIG. 5B), the pause valve assembly 142 is placed in an on or open position by positioning the pause actuator 112 toward the lid 118. The shuttle valve 134, which is operably connected to the pause actuator 112 via the retaining ring 132, is moved into the shuttle compartment 284 of the upper valve body 126. The top surface 344 of the body 332 of the shuttle valve 134 approaches or contacts the bottom surface 282 of the floor 272 of the head 256 of the upper valve body 126.

A flow gap 350 is simultaneously created between the bottom surface 346 of the base 334 of the shuttle valve 134 and the first surface 320 of the poppet support plate 316 of the poppet assembly 136. In this position of the shuttle valve 134, the cap 312, poppet neck 318, and sealing member 120d of the poppet assembly 136 are positioned below, not seated inside, the base cavity 348 of the shuttle valve 134. Fluid can flow from the hose 108 through the flow cavity 430 in the valve base 138, through the flow path 326 between the spokes 324 of the poppet support plate 316, into the cavity 298 of the shuttle retainer 130, into the base cavity 348 of the shuttle valve 134, and into the flow lumen 342 of the shuttle valve 134. Fluid passes through the flow aperture 276 in the upper valve body 126 and through the chamber valve 500 in the valve cavity 227 of the base 238 of the chamber 124.

Fluid then enters the agent chamber 226 of the chamber 124 and, if present, interacts with an oral hygiene agent in the chamber 226. In embodiments where the agent is a tablet, the fluid ablates the tablet and particles are deposited into the fluid stream, which then carries the particles through the channel 514 in the tip 104, out the tip outlet 105, and into a user's mouth. Specifically, the particles flowing within the fluid stream move from the chamber 226 to the filter housing 534, entering into the filter chamber 536. Before the fluid can enter into the tip fluid passage 514, the fluid passes through the filter assembly. The filter screen 530 acts to filter the stream delivered to the tip outlet 105, ensuring the particles above a predetermined size, determined by the size of the openings within the screen 530, are prevented from escaping into the tip. In other words, large particles are blocked and remain in the filter chamber 536 and/or chamber 226 until eroded or ablated to the predetermined size. This filtering helps to prevent the tip from becoming clogged with particles during use, as well as prevent the user from feeling larger particles, which may be undesirable. The filter brackets 557 within the filter housing 534 ensure that the filter 530 remains secured in place, even under the significant fluid pressure exerted by the fluid traveling through the chamber 536. As the fluid exits the filter housing 534, such as through the outlet at the top of the filter chamber 536, the tapered walls 543 reduce the fluid passageway and force the fluid into the tip flow passageway 514. From the tip flow passageway 514, the fluid and particles exit the tip outlet 105 and are deposited into a user's oral cavity and often are directed towards outer surfaces of a user's teeth to remove stains.

During operation, the user may activate pause mode to temporarily stop fluid flow to the tip 104. To initiate pause mode without turning off power to the oral irrigator to which the handle 100 is connected, the pause valve assembly 142 must be moved to a closed position as follows (see FIG. 5A). A user manually slides the pause actuator 112 downward relative to the housing 102, such as by grasping the grip portion 366 and moving it away from the lid 118 (i.e., in the down or off position) and substantially along a longitudinal axis of the housing 102. This translational movement of the pause actuator 112 also slides the coupled retaining ring 132 downward, which in turn slides the operably connected shuttle valve 134 downward. The flow gap 350 between the base 334 of the shuttle valve 134 and the poppet support plate 316, created during irrigate mode, is closed. The base 334 of the shuttle valve 134 contacts the first surface 320 of the poppet support plate 316 such that the cap 312, poppet neck 318, and sealing member 120d are received inside the base cavity 348 of the shuttle valve 134. The sealing member 120d helps provide a seal with the base cavity 348 and fluid is partially or completely prevented from entering the base cavity 348. Fluid can flow from the hose 108 through the valve base 138 through the flow path 326 of the poppet support plate 316 and into the cavity 298 of the shuttle retainer 130. But fluid cannot pass into the flow lumen 342 of the shuttle valve 134. Fluid flow is thereby paused or stopped through the shuttle valve 134 to the tip 104. The chamber valve 500 helps prevent fluid that has engaged with the oral hygiene agent from flowing back into the reservoir 12.

The pause mode is implemented by mechanical, not electrical, operation of the pause actuator 112. A mechanically actuated pause mode avoids the need for electrical circuitry in the handle 100, which thereby helps improve the safety of the handle 100 and the oral irrigator to which the handle is fluidly connected because electrical circuits are not in close physical proximity to fluid conduits. A mechanically-controlled instead of an electrically-controlled pause mode also decreases the manufacturing cost of the handle 100 and the oral irrigator. No separate battery is required in the handle 100 to power such circuits. Alternatively, the handle 100 need not be electrically wired to the oral irrigator. Thus, an easily accessible and selectable pause mode is provided to the user with significantly less manufacturing cost and greater safety.

Alternative Embodiments

In some embodiments, and with reference to FIGS. 5B and 5C, the pause valve assembly 142 includes a retaining clip 630 and does not include a shuttle retainer 130. Compared to a shuttle retainer 130, the retaining clip 630 may permit a reduction in the size, including the diameter, of the lower valve body 128 in which the clip 630 is received. The retaining clip 630 provides a barrier to most fluid flowing past the poppet assembly 136 when the handle 100 is in pause mode. When the handle 100 is in irrigate mode, the retaining clip 630 prevents water from contacting the sealing member 120c positioned under the shelf 404 of the lower valve body 128 by forming a seal with the base 334 of the shuttle valve 134. The retaining clip 630 also prevents the shuttle valve 134 from being pulled too far towards the lid 118 of the handle 100. Oral irrigator handles 100 or pause valve assemblies 142 that include a retaining clip 630 have a similar design, construction, function, assembly, and operation as those described above with the following exceptions.

With continued reference to FIGS. 5B and 5C, the retaining clip 630 may have an exterior wall 794 and a stepped interior wall 796.

When the pause valve assembly 142 is assembled, the retaining clip 630 may be received in the skirt cavity 412 of the lower valve body 128 such that the exterior wall 794 of the clip 630 is adjacent the inner skirt wall 416. The retaining clip 630 may be positioned below the sealing member 120c positioned under the shelf 404 of the lower valve body 128. The inner diameter of the retaining clip 630 may be slightly larger than the outer diameter of the shuttle valve 134 to permit water to reach the sealing member 120c and press the sealing member 120c against the shelf 404, thereby creating a faster or stronger seal than in the absence of water.

Compared to embodiments that include a shuttle retainer 130, when the pause valve assembly 142 includes a retaining clip 630, the base 334 and a lower portion of the body 332 of the shuttle valve 134 may be received in the skirt cavity 412 of the lower valve body 128 instead of in the cavity 298 of the shuttle retainer 130. When fluid is flowing into the handle 100 during either irrigate mode or pause mode, it flows into the skirt cavity 412 of the lower valve body 128 instead of the cavity 298 of the shuttle retainer 130.

During irrigate mode, when the pause valve assembly 142 is placed in an on or open position and the shuttle valve 134 is positioned towards the lid 118, the base 334 of the shuttle valve 134 may be blocked from advancing too far by contact with the interior wall 796 of the retaining clip 630.

Figure 32:
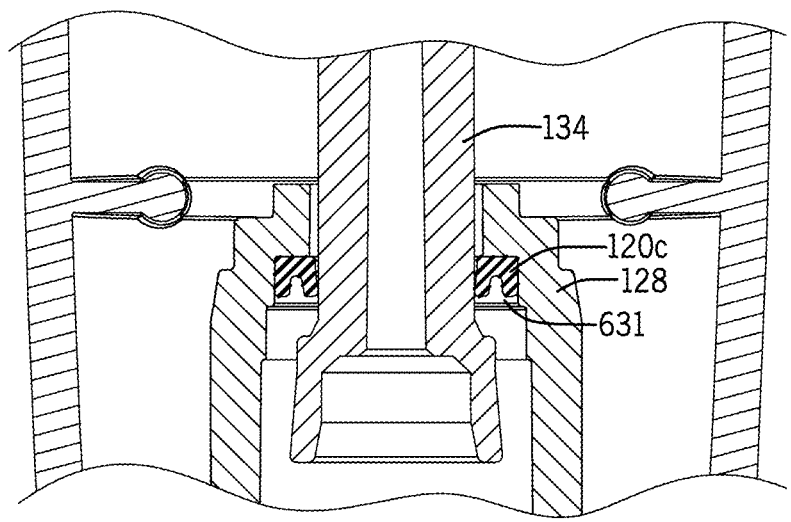
FIG. 32 is an enlarged view of the cross section of FIG. 27.
Figure 33:
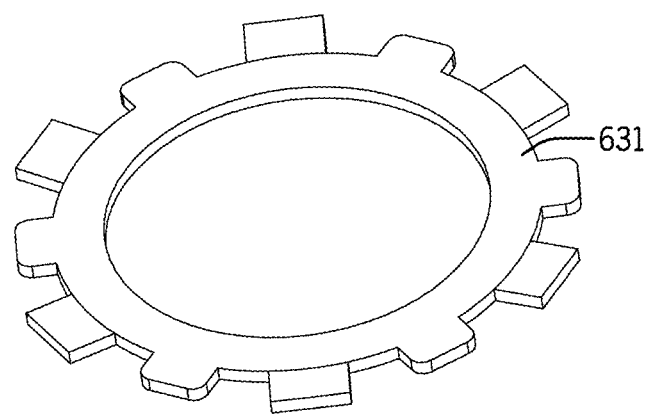
FIG. 33 is an isometric view of a seal retainer for the oral irrigator of FIG. 26A.

With reference to FIGS. 32 and 33, in some embodiments, the pause valve assembly may also include a securing clip 631 to secure the sealing member 120c, e.g., U-cup, in position. For example, the securing clip 631 may be formed of a high strength and/or rigid material, such as metal, and include a support prongs. In one example, the securing clip 631 is a metal star washer. The increased rigidity and strength of the metal provides additional support for the sealing member 120c to help ensure it remains in position, as the valve 134 moves relative thereto.

Figure 23B:
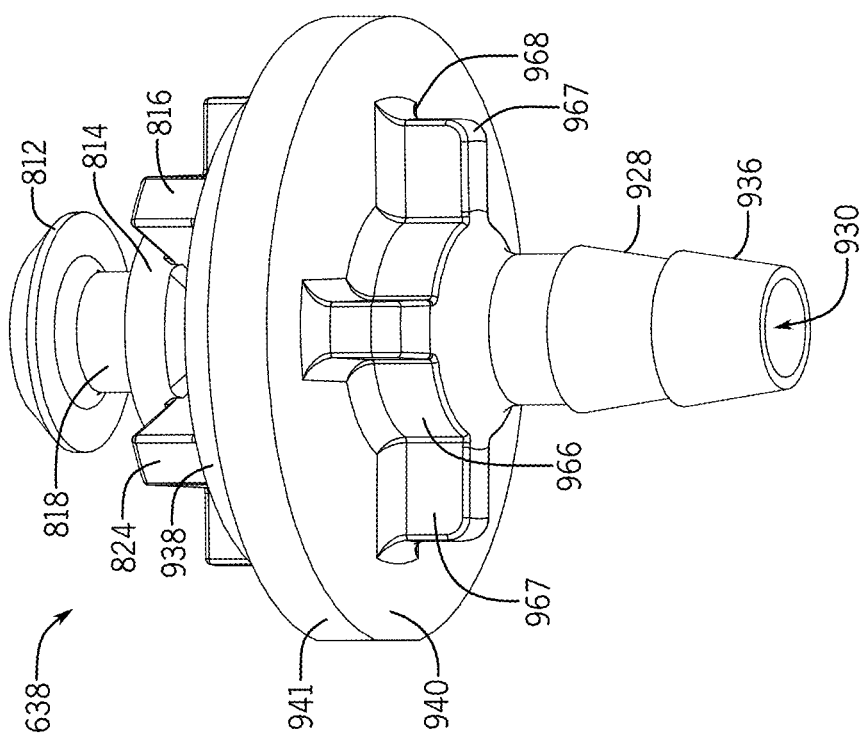
FIG. 23B is front bottom isometric view of the integrated valve base of FIG. 23A.
Figure 23A:
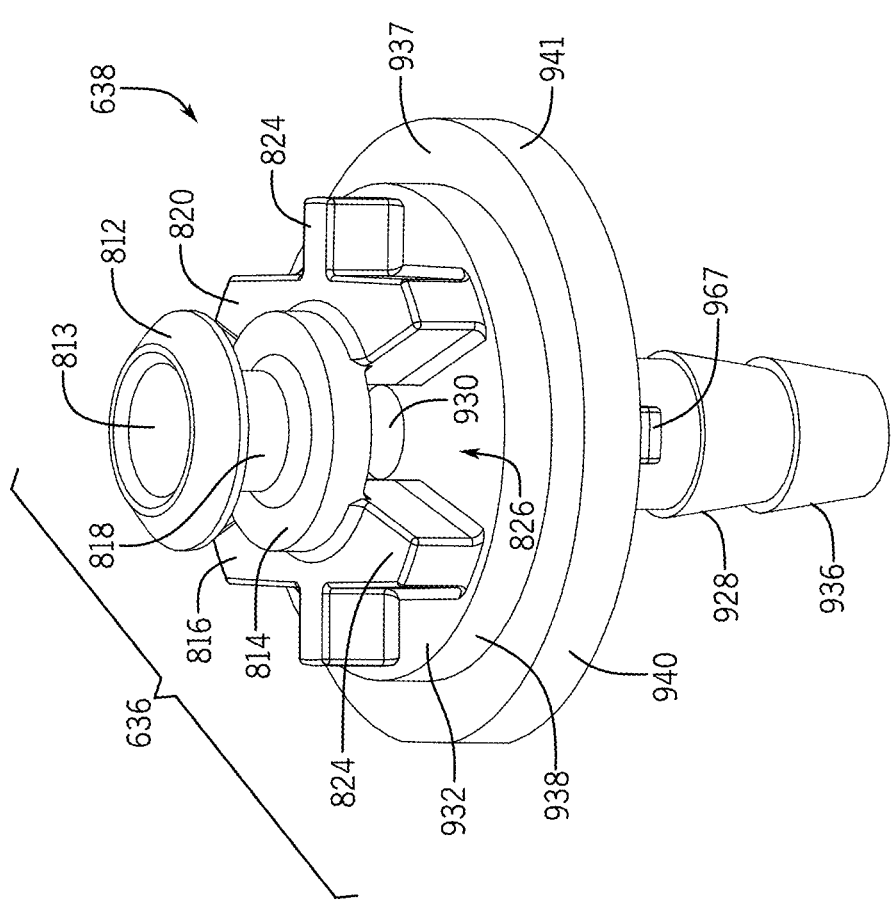
FIG. 23A is front top isometric view of an integrated valve base of the handle of FIG. 5B.

In some embodiments, and with reference to FIGS. 23A and 23B, the poppet assembly is incorporated into the valve base to form an integrated valve base 638, which may help decrease handle 100 manufacturing costs and/or time by reducing the number of component parts. Oral irrigator handles 100 that include an integrated valve base 638 have a similar design, construction, function, assembly, and operation as those described above with the following exceptions.

The integrated valve base 638 is configured to selectively disconnect fluid flow from the hose 108 to the chamber 124. The integrated valve base 638 may include a poppet assembly connected to an elongated barbed tip 928 by stacked concentric discs 938, 940. The poppet assembly 636 may include a cap 612, including a recessed center portion 813, connected to a poppet support plate 816 by a poppet neck 818. An annular platform 814 may encircle the neck 818 above the poppet support plate 816. The cap 812 and annular platform 814 are generally sized and shaped to be received in the shuttle valve 134. The poppet support plate 816 includes an upper surface 820 and a plurality of support features 824 extending outwardly from the platform 814. A flow path 826 may be defined between two adjacent but spatially separated support features 824. A sealing member 120d may be seated around the poppet neck 818 between the cap 812 and platform 814.

The upper disc 938 may have a smaller diameter than the bottom disc 940 such that a first surface 937 of the bottom disc 940 is exposed and is available to interface with the skirt 408 of the lower valve body 128.

An extension ledge 966 positioned between the bottom disc 940 and the barbed tip 928 may help maintain the integrated valve base 638 in a desired location in the handle 100. The extension ledge 966 may include a plurality of radially extending arms 967, each of which may have a lip 968 that is shaped to interface with a ledge 150a, 150b of the first and/or second shell 114, 116.

The integrated valve base 638 defines a flow cavity 930 from the barbed tip 928 through to the top surface 932 of the upper disc 938. The barbed tip 928 may include one or more gripping components 936 that enhance the connection between the integrated valve base 638 and the hose 108.

When the handle 100 is assembled, the cap 812, and the sealing member 120d positioned around the poppet neck 818, of the poppet assembly 636 may be received in the base cavity 348 of the shuttle valve 134. The first surface 820 of the poppet support plate 816 may be positioned below and adjacent to the bottom surface 346 of the base 334 of the shuttle valve 134 and, if present, below and adjacent to the second end 292 of the shuttle retainer 130.

The poppet support plate 816 and upper disc 938 of the integrated valve base 638 are received in the skirt cavity 412 of the lower valve body 128. The outer diameter of the bottom disc 940 of the integrated valve base 638 may be approximately the same as the outer diameter of the skirt 408 of the lower valve body 128 such that when the top surface 937 of the bottom disc 940 is positioned under the skirt 408, the outer skirt wall 414 may be flush with an outer surface 941 of the bottom disc 940. The barbed tip 928 of the integrated valve base 638 may be received in the barb aperture 442 of the base collar 140.

To assemble the swivel assembly 143, the barbed tip 428 of the integrated valve base 638 is received in the barb aperture 442 of the base collar 140. Ledges 150a, 150b of the shells 114, 116 may be positioned beneath the bottom disc 840 such that the lips 968 of the arms 967 rest on the ledges 150a, 150b.

During irrigate mode, fluid can flow from the hose 108 through the flow cavity 930 in the integrated valve base 638, through the flow path 826 between support features 824 of the poppet support plate 816, into the cavity 298 of the shuttle retainer 130 (or the skirt cavity 412 of the lower valve body 128 in embodiments having a retaining clip 630), into the base cavity 348 of the shuttle valve 134, and into the flow lumen 342 of the shuttle valve 134.

In some embodiments, the oral agent chamber may be connected to the tip, rather than the handle. FIGS. 24A-24C illustrate an example of a tip 550 including an integrated chamber 568. These embodiments allow a user to use oral hygiene agent with substantially any oral irrigator.

In one example, the tip 550 may include an upper portion 552 and a lower portion 564 that connect together, e.g., via threading, snap fit, or the like. The upper portion 552 may include a body 556 positioned between a tip outlet 554 and a skirt 560. A tip channel 558a may be defined through the upper portion 552 and may permit the passage of fluid. A cavity 562 for receiving the lower portion 564 may be defined in the skirt 560 and may include engagement features 574a, such as threads, for securing the lower portion 564.

The lower portion 564 may include a chamber body 566 connected to a stem 570, which terminates in a tip inlet 572. Positioning the chamber body 566 above the stem 570 helps permit the stem 570 to be configured to easily engage with the top end of many different designs or styles of oral irrigator handles.

As in the upper portion 552, a tip channel 558b may be defined through the stem 570 from the tip inlet 572 to the chamber body 566.

The chamber body 566 may define a chamber 568. The chamber 568 may be sized and shaped to receive an oral hygiene agent. For example, the diameter of the chamber 568 may be greater than the diameter of the channels 558a, 558b. One or more ribs 569 may be formed on an inner wall 582 of the chamber 568 to help prevent an oral hygiene agent from adhering to the wall 582 and to help permit fluid to flow around the agent.

Engagement features 574b, such as threads, may be formed on an outer wall 584 of the chamber body 566. The engagement features 574b may be complementary to the engagement features 574a of the upper portion 552 such that the features 574a, 574b can connect and help secure the upper portion 552 to the lower portion 564.

One or more of a screen 576, screen support 578, and sealing member 580 may be seated in the upper portion 552 above the chamber 568 when the upper portion 552 is connected to the lower portion 564. The screen 576 may help prevent large particles from an agent in the chamber 568 from clogging the tip channel 558a or tip outlet 554.

The sealing member 580 may be, for example, an O-ring or U-cup and may help provide a fluid-tight seal between the upper and lower portions 552, 564.

In other embodiments, the chamber 568 may be defined in both the upper and lower portions 552, 564.

FIGS. 26A-32 illustrate various views of another embodiment of the oral cleansing handle 601. The handle 601 may be substantially the same to handle 100 and any elements not specifically discussed with reference to handle 601 may be incorporated into or the same as handle 100. The handle 601 may include a housing 605, a pause assembly 603, a latch assembly 607, and a lid 609, each of which may be similar to the like features of the embodiments shown in FIGS. 1A-5C.

With respect the housing 605, the housing 605 may include a different front or first shell 611. With reference to FIG. 26C, the front shell 611 may include a latch support cavity 616 that receives and houses portions of the latch assembly 607 and a latch guide 615 that guides the catch 212 as it moves relative to the handle housing. Specifically, the front shell 611 may include an upper rib 618 defined towards the top end of the shell 611 and extending outwards from the interior surface of the shell. A latch rib 617 extends parallel to the upper rib 618 and may be connected to the upper rib 618 by one or more connection regions, which help to increase the rigidity of the ribs 617, 618. The latch rib 617 and upper rib 618 may extend across a substantial portion of the width of the front shell 611. Additionally, a bottom rib 619a, 619b may be positioned below the latch rib 617 and extend along a portion for the shell width. In one embodiment, the bottom rib 619a, 619b may be broken into two ribs 619a, 619b formed on adjacent sides of the button aperture 152. The latch rib 617 extends across the width of the button aperture 152, whereas the bottom rib 619a, 619b extends only partially into the width of the button aperture 152. In this manner, the button aperture 152 may have a full opening on the outer side of the front shell 611, but be partially obstructed by the ribs formed from the interior surface. When assembled, the latch cavity 616 receives the latch 180, 625, such that the latch body sits on the bottom rib 619a, 619b and the latch rib 617 extends over the top surface of the latch 180, 625.

With continued reference to FIG. 26C, the latch guide 615 is formed by the latch rib 617 and optionally the upper rib 618. The latch guide 615 acts to direct the catch 212 of the latch assembly during opening and closing of the lid 609. The latch guide 615 allows the catch 212 to move more smoothly as the user opens and closes the lid, as it acts to define a track or guide for the latch movement.

Figure 27:
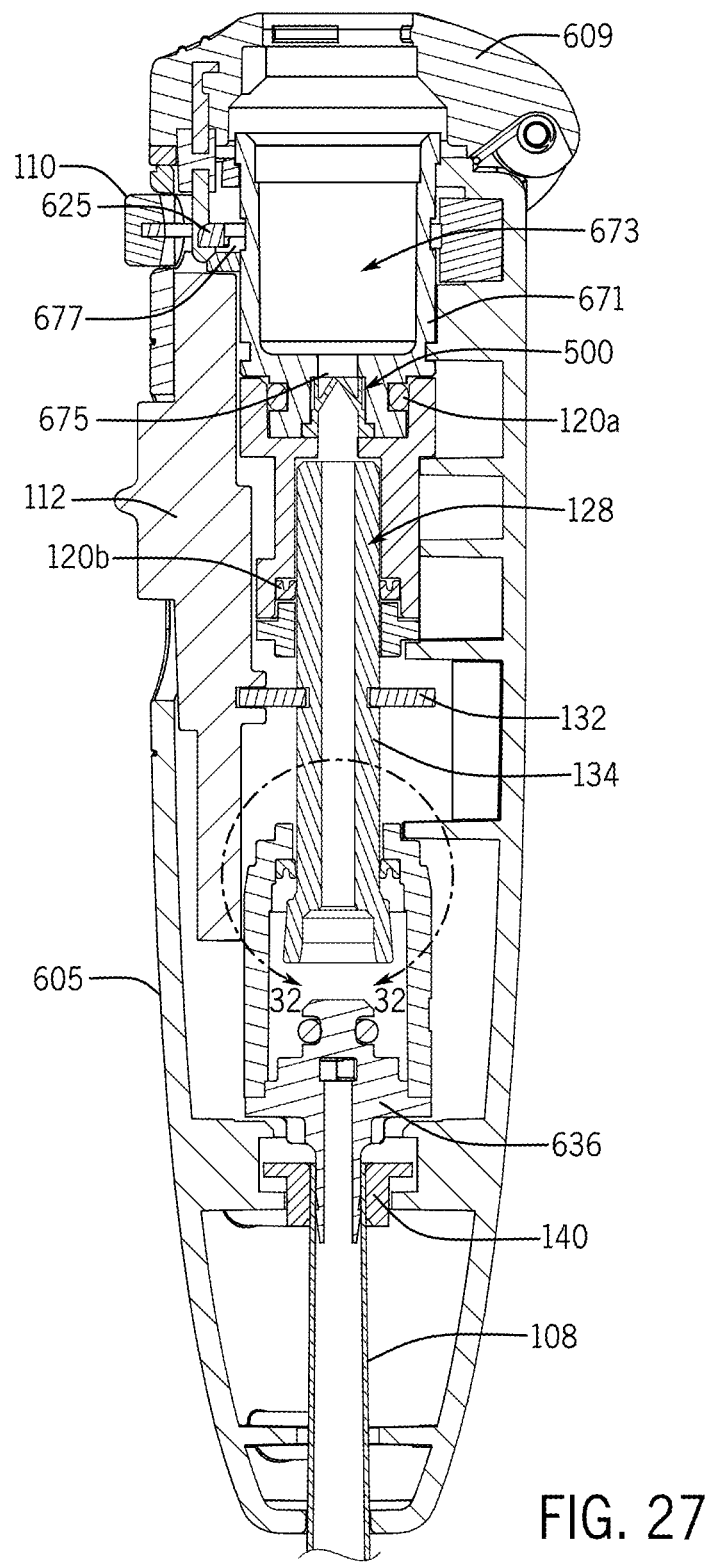
FIG. 27 is a cross-section view of the oral irrigator handle of FIG. 26A taken along line 27-27 in FIG. 26A.

With reference to FIG. 27, the handle 601 may also include a different agent housing as compared to the one shown in FIGS. 13A-13B. In the FIG. 27 embodiment, the agent housing 617 defines an agent chamber 673 which is configured similar to chamber 226 to receive tablet 590. The agent chamber 673 receives fluid via the chamber inlet 675 defined through a bottom wall thereof. Additionally, the agent housing 671 may include a spacing groove 677 defined on an outer surface thereof. The spacing groove 677 may be an annular groove that is aligned with the location of the latch, and provides additional lateral movement space for the latch assembly as a user opens and closes the lid. The spacing groove 677 allows the chamber 673 to have a sufficiently large diameter to accommodate the tablet 590, while allowing for adequate movement of the latch assembly, without increasing the overall diameter of the handle 601.

The latch assembly 621 and lid 619 of the handle 601 may include varied feature as compared to the latch assembly and lid of FIGS. 1A-24B, each are discussed in turn.

Figure 28:
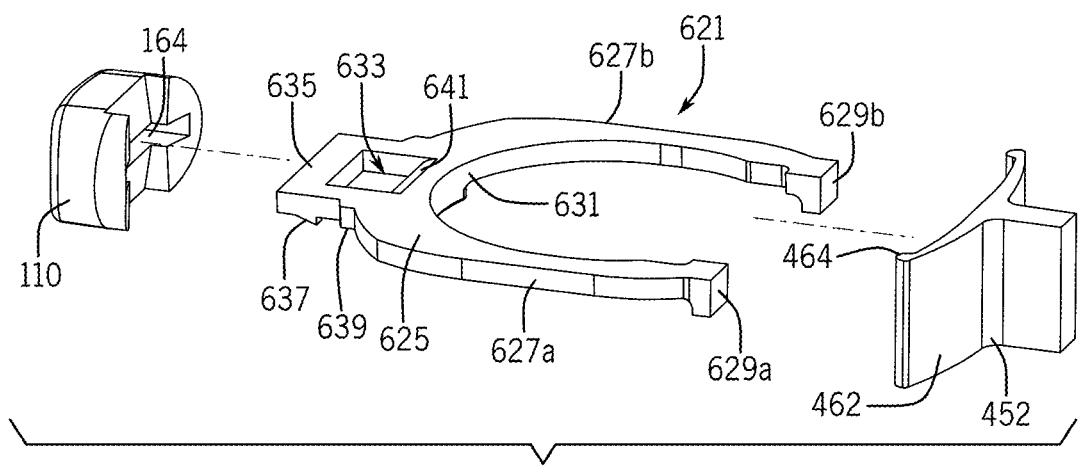
FIG. 28 is an exploded view of a latch assembly for the irrigator handle of FIG. 26A.
Figure 29A:
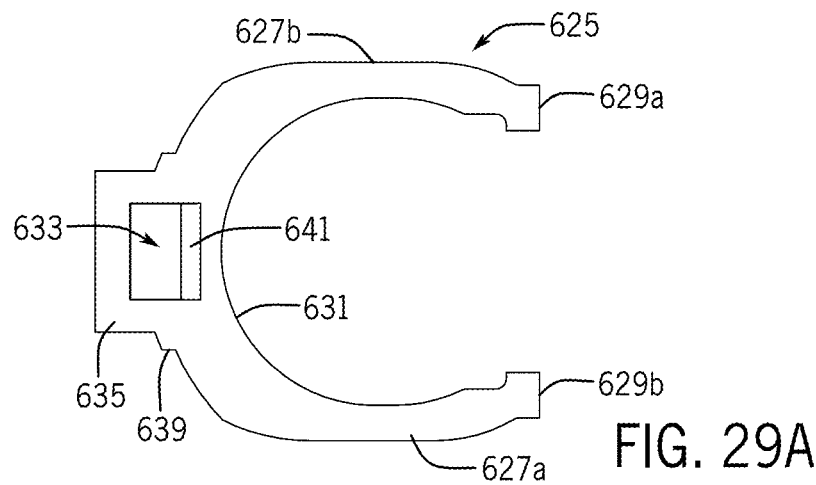
FIG. 29A is a top plan view of a latch for the cover assembly of FIG. 28.
Figure 29B:
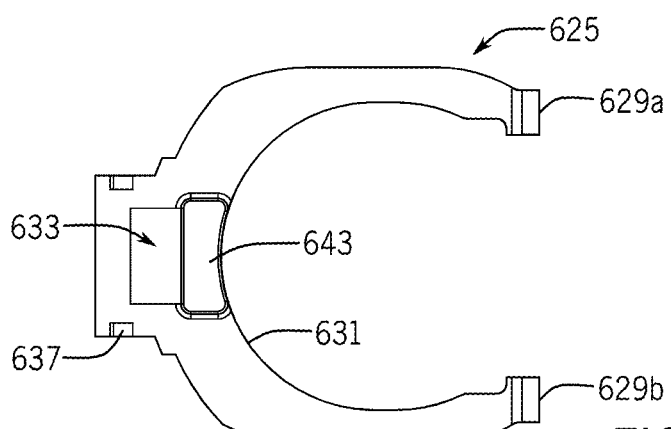
FIG. 29B is a bottom plan view of the latch of FIG. 29A.

With reference to FIGS. 28-29B, the latch assembly 621 includes a button 110, a latch 625, and a biasing element or spring 452. In some embodiments, the button 110 and the spring 452 may be the same as those in FIGS. 8A and 8B. However, the latch 625 may be varied. For example, the latch 625 may include a securing head 635 extending outwards from a first end of the latch 625 and arms 627a, 627b extending from the opposite side. The securing head 635 is configured to secure the button 110 and may include securing elements, such as securing prongs 637 that act to help retain the latch 625 within the button aperture 164. Button stops 639 may be formed on each sidewall of the securing head 635 to limit motion of the button 110 relative to the securing head 635, ensuring that the user force is fully transmitted to the latch 625. A catch aperture 633 may be defined through the top surface of the securing head 635 of the latch 625 with a catch slide 641 surface being angled or sloped from the top surface towards the bottom surface of the latch 625 at a first end of the latch walls defining the catch aperture 633. The slope of the catch slide 641 is meant to assist the latch catch as it extends through the latch 625 and prevent the latch catch from catching too soon.

With reference to FIG. 29B, a catch seat 643 is defined on a bottom surface of the latch 625 and extends downwards from the bottom surface. The catch seat 643 may be formed as a protrusion and configured to engage the catch. In one embodiment, the catch slide 641 slopes down and integrally forms the catch seat 641. The latch 625 may be formed in a variety of manners, but in one example, the latch 625 may be formed via a metal injection molding process.

With reference to FIGS. 29A and 29b, the latch arms 627a, 627b may be mirror images of one another and may include engagement ends 629a, 629b, which may be defined as engagement faces, that engage with the spring 452 to causes the spring to flex and deform when the latch is activated by a user, similar to as described above with respect to latch 180.

Figure 30:
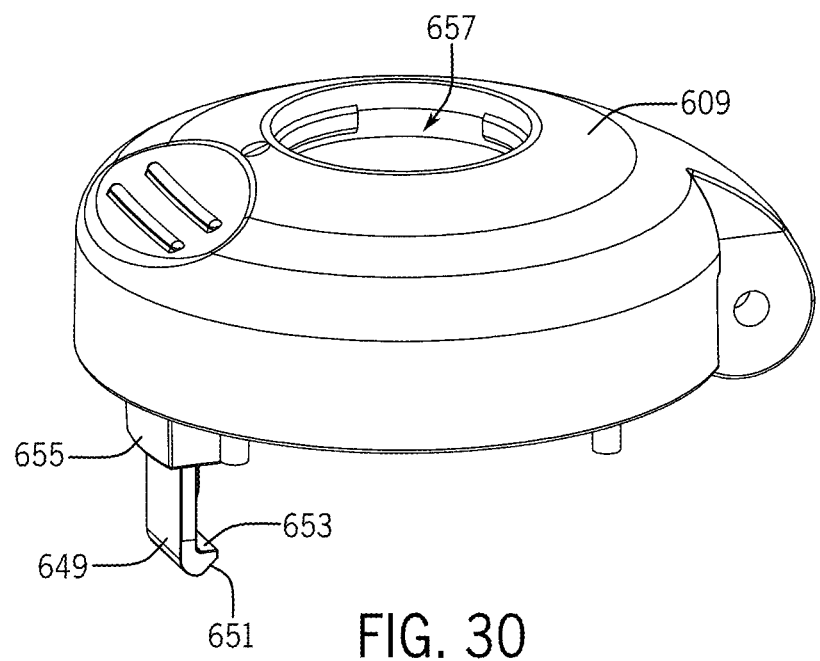
FIG. 30 is a side isometric view of a cap for the oral irrigator of FIG. 26A.
Figure 31:
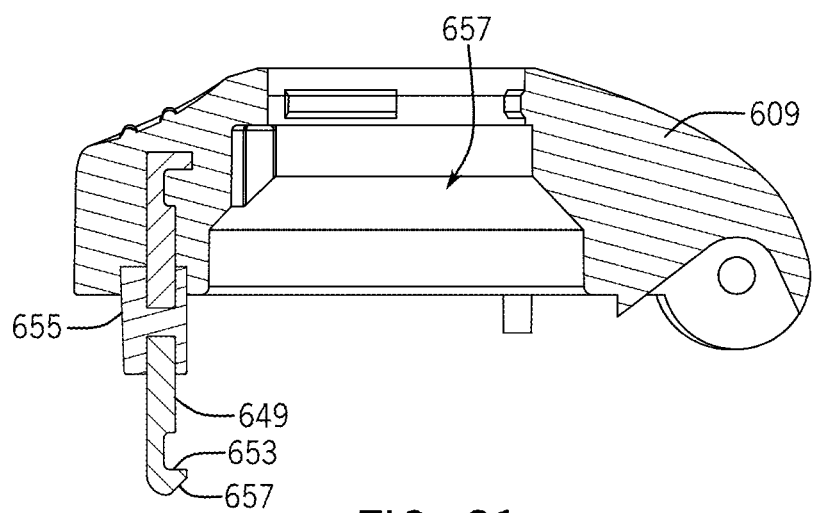
FIG. 31 is a cross-section view of the cap of FIG. 30 taken along line 31-31 in FIG. 30.

With reference to FIGS. 30 and 31, the lid 609 may be substantially similar to lid 118. However, in this example, the catch 649, which engages the latch 625, may include a different shape and optionally may be formed via metal injection molding as compared to a stamped metal process. The catch 649 may be secured or integrally formed with the lid 609. In one embodiment, the catch 649 is secured to the lid 609 via a catch housing 655 that extends downwards from the lid 609 and the catch is received therein. Extending downwards from the catch housing 655, the catch 649 may have a generally "hook" shape with a bottom end 651 of the catch 649 turning upwards and defining a catch seat 653. The catch seat 653 may be substantially planar and be defined on a surface perpendicular to the length of extension of the catch 649.

Hose Swivel

During use, as the user moves the handle 100 into different angles and positions to access different areas of the mouth, the hose 108 can rotate freely relative to the handle 100 to remain free from tangles, bends, or kinks while maintaining a desired handle 100 orientation. In particular, as the user moves the handle 100 to different orientations, the hose 108 can rotate at its connection to the handle 100 as components of the handle 100 rotate within and relative to the housing 102. For example, the valve base 138 may be ultrasonically welded to the skirt 408 of the lower valve body 128 such that rotation of the hose 108 attached to the barbed tip 428 of the valve base 138 rotates the valve base 138, poppet assembly 136 if present, shuttle valve 134, retaining ring 132, and lower valve body 128 within and relative to the housing 102. In some embodiments, the materials of some or all of the base collar 140, valve base 138, shuttle valve 134, retaining ring 132, and lower valve body 128 are selected to be low-friction so as to introduce minimal to no drag.

CONCLUSION

All directional references (e.g., upper, lower, upward, downward, left, right, leftward, rightward, top, bottom, above, below, vertical, horizontal, clockwise, and counter-clockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An oral irrigator comprising
a housing including a fluid inlet and a fluid outlet;
a chamber housing positioned within the housing between the fluid inlet and the fluid outlet, wherein the chamber housing comprises:
an agent chamber for receiving an oral hygiene agent therein, the agent chamber having a bottom surface, a chamber inlet defined through the bottom surface, and a chamber outlet positioned opposite of the bottom surface, wherein the chamber inlet is configured to direct fluid from the fluid inlet to impinge against a surface of the oral hygiene agent facing towards the bottom surface of the agent chamber; and
a lid pivotably coupled to the housing, wherein in a closed position, the lid at least partially covers the agent chamber and in an open position, the lid uncovers the agent chamber, the lid defining a tip aperture on a top surface thereof, wherein the tip aperture is in fluid communication with the agent chamber; and
a tip removably coupled to the lid, the tip comprising:
a filter screen; and
a tip outlet; wherein the tip is received through the tip aperture of the lid such that in the closed position of the lid the filter screen is positioned below a top surface of the lid and between the agent chamber and the tip outlet so as to filter fluid exiting the agent chamber.

2. The oral irrigator of claim 1, wherein the filter screen prevents particles larger than predetermined size from traveling to the tip outlet.

3. The oral irrigator of claim 1, wherein the tip and the filter screen move with the lid between the open position and the closed position.

4. The oral irrigator of claim 1, wherein the housing comprises a handle housing and the handle housing is fluidly coupled to a reservoir.

5. The oral irrigator of claim 1, further comprising a latch assembly coupled to the housing, wherein the latch assembly selectively secures the lid to the housing when the lid is in the closed position.

6. The oral irrigator of claim 5, wherein the latch assembly comprises:
   a latch coupled to the housing and movable between a first position and a second position;
   a spring coupled to the housing and engaging a portion of the latch, wherein the spring biases the latch towards the first position; and
   a button coupled to the latch, wherein a force exerted on the button, causes the latch to overcome the spring bias and move from the first position to the second position.

7. The oral irrigator of claim 6, wherein the lid further comprises a catch, wherein
   in the open position of the lid, the catch is disengaged from the latch; and
   in the closed position of the lid, the catch is engaged with the latch.

8. The oral irrigator of claim 1, wherein the tip further comprises:
   a tip seal cap positioned around a bottom end of the tip, wherein the tip seal cap seals against an interior surface of the lid when the tip is coupled to the lid.

9. The oral irrigator of claim 8, wherein the tip seal cap comprises:
   a skirt defining an angled surface; and
   a rim formed at a bottom end of the skirt.

10. The oral irrigator of claim 1, wherein the fluid flows from the fluid inlet to the fluid outlet is in a single direction.

11. The oral irrigator of claim 1, wherein the tip further comprises a first end and a second end, wherein the first end extends above the top surface of the lid and the second end extends below the top surface of the lid and the filter screen is positioned between the first end and the second end.

12. The oral irrigator of claim 1, wherein the filter screen is spaced apart from a terminal end of the tip.

13. The oral irrigator of claim 1, wherein tip further comprises:
   a filtering chamber; and
   a screen support extending from an interior wall of the tip, wherein the filter screen is positioned within the filtering chamber and adjacent to the screen support.

14. An oral irrigator device comprising:
   a pump in fluid communication with a reservoir; and
   a handle in fluid communication with the pump, the handle comprising:
      an agent housing defining an agent chamber, the agent housing having a chamber inlet and a chamber outlet in fluid communication with the agent chamber; and
      a chamber valve positioned between the reservoir and the chamber inlet, wherein a fluid flows from the reservoir into the agent chamber from the chamber inlet in a first direction and exits the agent chamber from the chamber outlet in the first direction; and
      a cover coupled to the handle, wherein the cover with the housing defines an interior cavity and the cover is positionable between an open position uncovering the agent chamber and a closed position at least partially covering the agent chamber, the cover comprising a tip aperture on a top surface thereof, wherein the tip aperture is in fluid communication with the chamber outlet; and
   a tip removably coupled to the handle, the tip comprising:
      a filter screen; and
      a tip outlet, wherein the tip is received through the tip aperture of the cover such that in the closed position of the cover, the filter screen is positioned within the interior cavity and the tip is in fluid communication with the chamber outlet.

15. The oral irrigator device of claim 14, wherein the tip is movable with the cover such that as the cover transitions between the open position and the closed position, the tip and the filter screen move with the cover.

16. The oral irrigator device of claim 15, wherein the tip further comprises:
   a tip seal cap coupled to the tip to seal a connection between the tip and the cover.

17. The oral irrigator device of claim 16, wherein the tip further comprises an alignment indicator.

18. The oral irrigator device of claim 16, wherein the tip seal cap comprises:
   a skirt configured to seal against a portion of the cover; and
   an alignment tab.

19. The oral irrigator device of claim 14, further comprising a latch to secure the cover to the handle in the closed position.

20. The oral irrigator device of claim 19, wherein the latch engages with a corresponding catch on the cover to secure the cover in the closed position.

21. The oral irrigator device of claim 20, wherein the latch moves across a width of the handle to engage and disengage with the catch.

22. An oral hygiene system, comprising:
   an oral agent tablet; and
   the oral irrigator device of claim 14.

23. The oral hygiene system of claim 22, wherein:
   the agent chamber has a chamber diameter; and
   the tablet comprises a tablet diameter, wherein the tablet diameter is between 80 to 95 percent of the chamber diameter.

24. The oral irrigator device of claim 14, wherein the agent housing further comprises a connection base extending from a bottom surface of the agent housing, wherein the chamber valve is positioned within the connection base and is in fluid connection with the chamber inlet and the chamber valve prevents the fluid from flowing into the connection base from the chamber inlet in a second direction.

* * * * *